US 8,093,044 B2

(12) United States Patent
Kincaid et al.

(10) Patent No.: US 8,093,044 B2
(45) Date of Patent: Jan. 10, 2012

(54) METHODS FOR IDENTIFYING INHIBITORS OF BOTULINUM NEUROTOXINS

(76) Inventors: Randall Kincaid, Rockville, MD (US); George Oyler, Baltimore, MD (US); Yien Che Tsai, Frederick, MD (US); Paul S. Fishman, Baltimore, MD (US)

(*) Notice: Subject to any disclaimer, the term of this patent is extended or adjusted under 35 U.S.C. 154(b) by 0 days.

(21) Appl. No.: 12/630,336

(22) Filed: Dec. 3, 2009

(65) Prior Publication Data

US 2010/0204054 A1 Aug. 12, 2010

Related U.S. Application Data

(60) Division of application No. 11/095,055, filed on Mar. 31, 2005, now Pat. No. 7,632,917, which is a continuation of application No. PCT/US2003/030899, filed on Oct. 3, 2003.

(60) Provisional application No. 60/415,177, filed on Oct. 1, 2002.

(51) Int. Cl.
C07K 14/00 (2006.01)
A61K 39/08 (2006.01)
C12N 5/10 (2006.01)

(52) U.S. Cl. ........ 435/325; 530/324; 530/333; 530/350; 530/300; 424/239.1; 435/4; 435/7.71

(58) Field of Classification Search .................. 530/300, 530/324, 333, 350; 424/239.1; 435/4, 7.71, 435/325
See application file for complete search history.

(56) References Cited

U.S. PATENT DOCUMENTS

| | | | |
|---|---|---|---|
| 5,965,699 | A | 10/1999 | Schmidt et al. |
| 6,203,794 | B1 | 3/2001 | Dolly et al. |
| 6,504,006 | B1 | 1/2003 | Shine et al. |
| 6,762,280 | B2 | 7/2004 | Schmidt et al. |
| 2001/0012833 | A1 | 8/2001 | Aoki et al. |
| 2002/0127247 | A1 | 9/2002 | Steward et al. |
| 2003/0077685 | A1 | 4/2003 | Schmidt et al. |
| 2003/0143650 | A1 | 7/2003 | Steward et al. |
| 2003/0143651 | A1 | 7/2003 | Steward et al. |
| 2004/0072270 | A1 | 4/2004 | Fernandez-Salas et al. |
| 2004/0115727 | A1 | 6/2004 | Steward et al. |
| 2004/0146963 | A1 | 7/2004 | Schmidt et al. |
| 2005/0100973 | A1 | 5/2005 | Steward et al. |
| 2005/0136394 | A1 | 6/2005 | Fang et al. |
| 2005/0153945 | A1 | 7/2005 | Bavari et al. |

OTHER PUBLICATIONS

Fasshauer, Dirk et al., Conserved Structural Features of the Synaptic Fusion Complex: SNARE Proteins Reclassified as Q- and R-SNAREs, Proc. Natl. Acad. Sci. USA, 1998, 15781-15786, vol. 95.

Steegmaier, Martin et al., Three Novel Proteins of the Syntaxin/SNAP-25 Family, J. Biol. Chem., 1998, 34171-34179, vol. 273, No. 51, The American Society for Biochemistry and Molecular Biology, Inc.

Vaidyanathan, Vadakkanchery V. et al., Proteolysis of SNAP-25 Isoforms by Botulinum Neurotoxin Types A, C, and E: Domains and Amino Acid Residues Controlling the Formation of Enzyme-Substrate Complexes and Cleavage, J. Neurochem., 1999, 327-337, vol. 72, No. 1, Lippincott Williams & Wilkins, Philadelphia.

Hearn, Milton T. W., et al., Applications of Novel Affinity Cassette Methods: Use of Peptide Fusion Handles for the Purification of Recombinant Proteins, J. Mol. Recognit., 2001, 323-369, vol. 14.

Hallis B., et al., Development of Novel Assays of Botulinum Type A and B Neurotoxins Based on Their Endopeptidase Activities, Journal of Clinical Microbiology, 34(8):1934-1938, (Aug. 1996).

Witcome M., et al., Dev. Biol Stand, Novel Assays for the Detection of Botulinum Toxins in Foods, 101:141-5 (1999).

Szilagyi M., et al., Toxicon, Development of Sensitive Colorimietric Capture Elisas for *Clostridium botulinum* Neurotoxins Serotypes A and B, 38(3):381-89 (Mar. 2000).

Shone CC., et al., Protelolytic Cleavage of Synthetic Fragments of Vesicle-Associated Membrane Protein, Isoform-2 by Botulinum Type B Neurotoxin, Eur J. Biochem, 217(3):965-71 (Nov. 1, 1993).

Ekong TA, et al., Recombinant SNAP-25 is an Effective Substrate for *Clostridium botulinum* Type A Toxin Endopeptidase Activity in Vitro, Microbiology, 143(PT 10):3337-47 (Oct. 1997).

Wictome M., et al., Development of an In Vitro Bioassay for *Clostridium botulinum* Type B Neurotoxin in Foods that is More Sensitive than the Mouse Bioassays, Applied and Environmental Microbiology, 65(9):3787-3792 (Sep. 1999).

Sharma SK, et al., Methods for Detection of *Clostridium botulinum* Toxin in Foods, J. Food Prot., (6):1256-63 (Jun. 2005).

*Primary Examiner* — Chih-Min Kam
(74) *Attorney, Agent, or Firm* — Whiteford, Taylor & Preston, LLP; Joseph L. Morales

(57) ABSTRACT

A system and method for identifying a botulinum neurotoxin inhibitor employing a botulinum neurotoxin substrate complex having a peptide substrate, preferably SNAP-25, a reporter domain on one side of said peptide substrate and an immobilization domain on the opposite side of said peptide substrate. The botulinum neurotoxin inhibitor is identified by its ability to decrease the relative amount of cleaved complex, detected through measuring a decrease in complex bound to a solid support. The method of the present invention also utilizes novel cells that express a botulinum neurotoxin substrate complex. The methods of the present invention are adapted for cell based screening to monitor the catalytic activity of a BoNT in living cells and to identify molecules that inhibit the catalytic activity of a BoNT in living cells. Also provided are novel stable cell lines that express the botulinum toxin substrate complex and viral vectors capable of efficiently expressing an active light chain of the BoNT within mammalian cells.

26 Claims, 11 Drawing Sheets

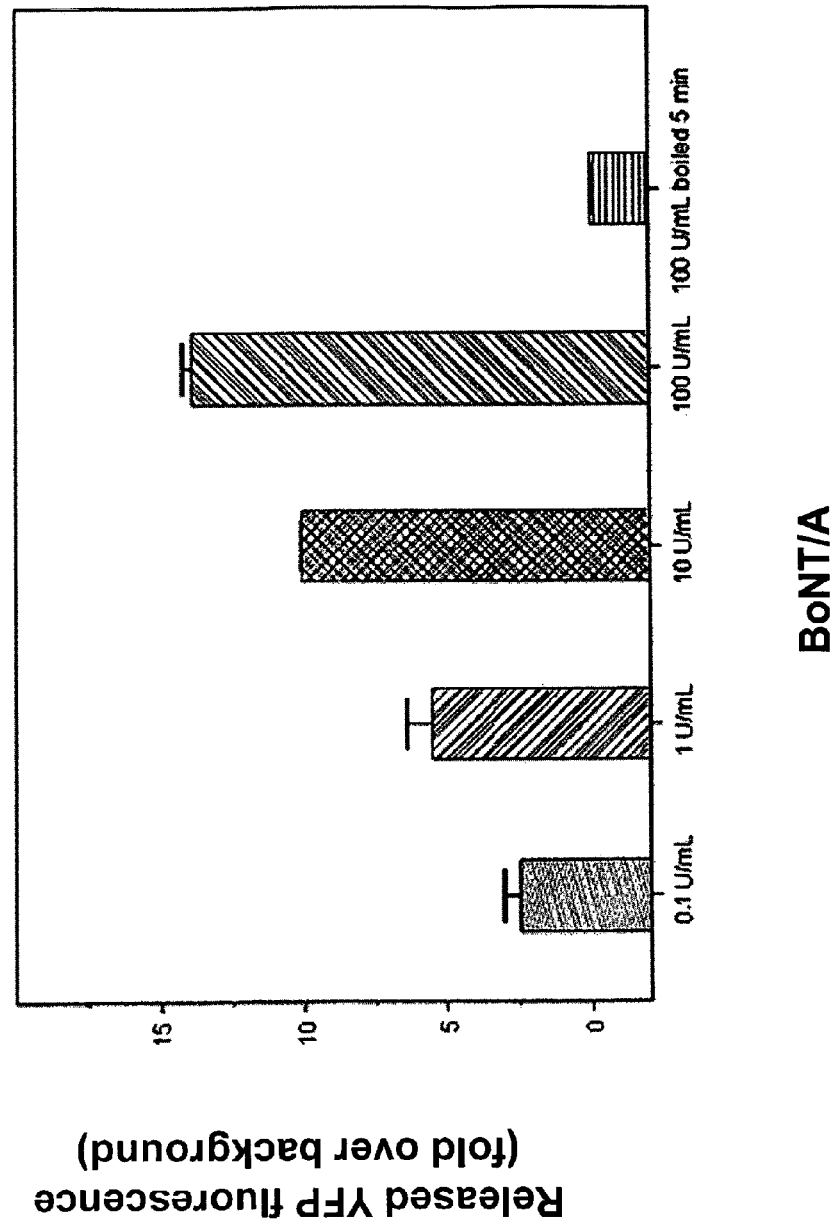

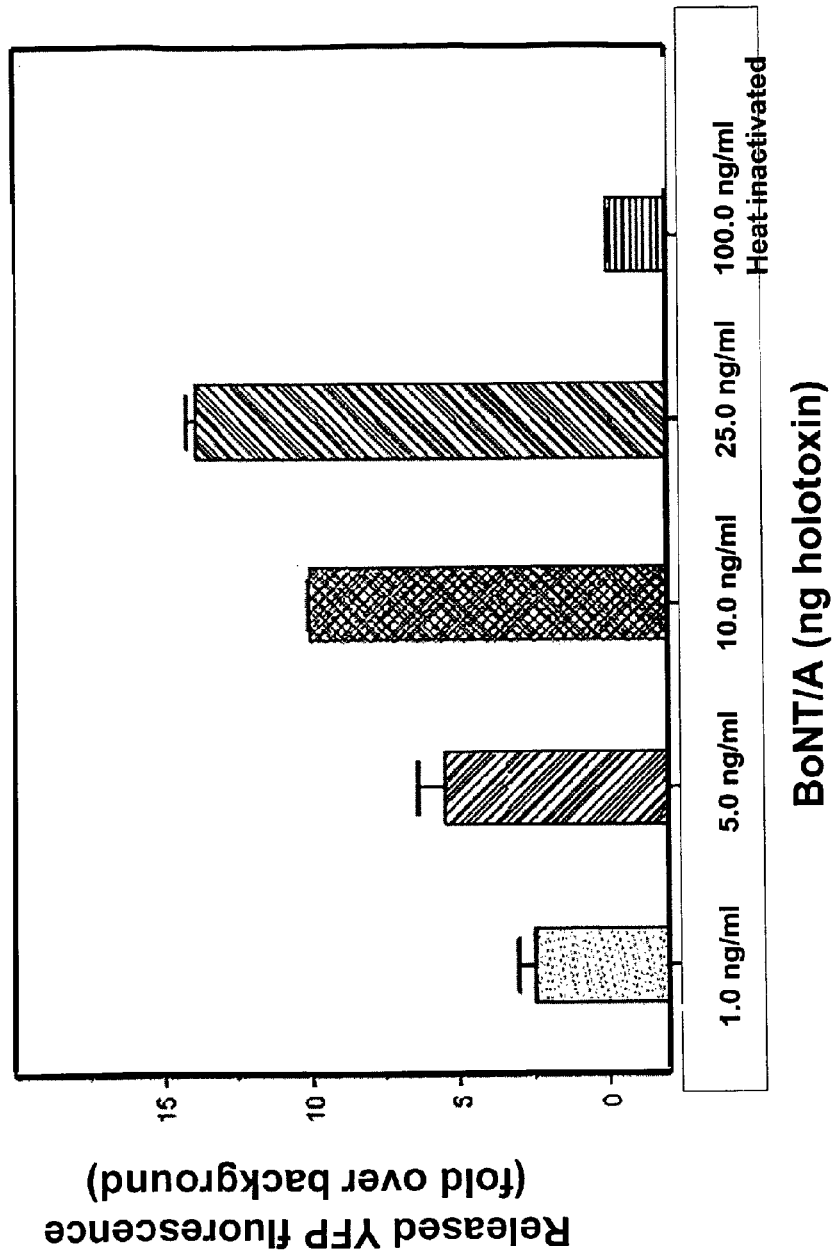

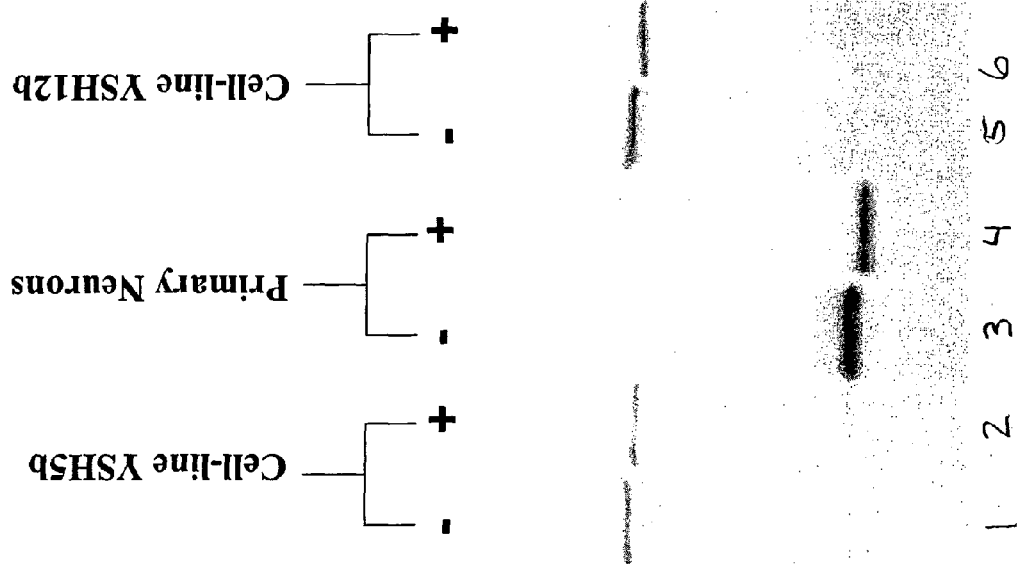

FIGURE 6
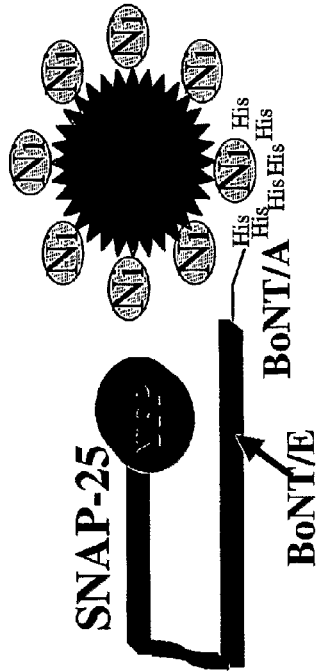
Fluorescence is bound to beads
When SNAP-25 is intact, YFP fluorescence is bound to the nickel (Ni) beads and is removed from solution.
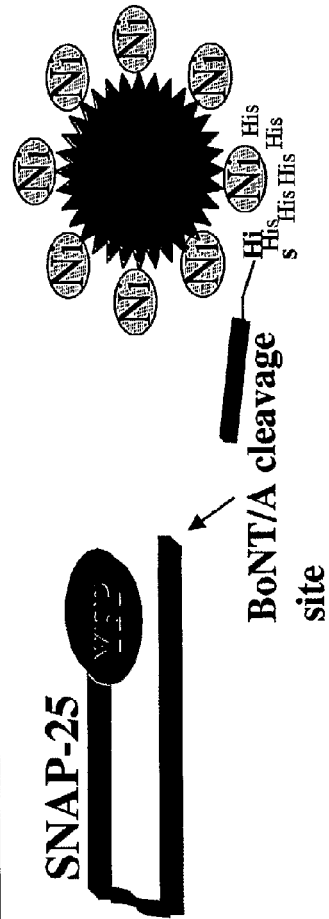
Fluorescence is in solution
When SNAP-25 has been cleaved by BoNT/A, C, or E protease activity, YFP fluorescence will be released into solution, and detection of fluorescence in solution will indicate the presence of active toxin.

FIGURE 8A    BoNT/A LC (SEQ ID NO: 1)

ATCTCGAGTCGCTAGCATGCCCTTCGTGAACAAGCAGTTCAACTACAAGGACCCC
GTGAACGGCGTGGACATCGCCTACATCAAGATCCCCAACGCCGGCCAGATGCAG
CCCGTGAAGGCCTTCAAGATCCACAACAAGATCTGGGTGATCCCCGAGCGCGAC
ACCTTCACCAACCCCGAGGAGGGCGACCTGAACCCCCCCCCGAGGCCAAGCAG
GTGCCCGTGTCCTACTACGACTCCACCTACCTGTCCACCGACAACGAGAAGGACA
ACTACCTGAAGGGCGTGACCAAGCTGTTCGAGCGCATCTACTCCACCGACCTGGG
CCGCATGCTGCTGACCTCCATCGTGCGCGGCATCCCCTTCTGGGGCGGCTCCACC
ATCGACACCGAGCTGAAGGTGATCGACACCAACTGCATCAACGTGATCCAGCCC
GAC<u>GGATCC</u>TACCGCTCCGAGGAGCTGAACCTGGTGATCATCGGCCCCTCCGCC
GACATCATCCAGTTCGAGTGCAAGTCCTTCGGCCACGACGTGCTGAACCTGACCC
GCAACGGCTACGGCTCCACCCAGTACATCCGCTTCTCCCCCGACTTCACCTTCGG
CTTCGAGGAGTCCCTGGAGGTGGACACCAACCCCCTGCTGGGCGCCGGCAAGTT
CGCCACCGACCCCGCCGTGACCCTGGCCCACGAGCTGATCCACGCCGAGCACCG
CCTGTACGGCATCGCCATCAACCCCAACCGCGTGTTCAAGGTGAACACCAACGCC
TACTACGAGATGTCCGGCCTGGAGGTGTCCTTCGAGGAGCTGCGCACCTTCGGCG
GCCACGACGCCAAGTTCATCGACTCCCTGCAGGAGAACGAGTTCCGCCTGTACTA
CTACAACAAGTTCAAGGACGTGGCCTCCACCCTGAACAAGGCCAAGTCCATCAT
CGGCACCACCGCCTCCCTGCAGTACATGAAGAACGTGTTCAAGGAGAAGTACCT
GCTGTCCGAGGACACC<u>*TCCGGA*</u>AAGTTCTCCGTGGACAAGCTGAAGTTCGACAAG
CTGTACAAGATGCTGACCGAGATCTACACCGAGGACAACTTCGTGAACTTCTTCA
AGGTGATCAACCGCAAGACCTACCTGAACTTCGACAAGGCCGTGTTCCGCATCA
ACATCGTGCCCGACGAGAACTACACCATCAAGGACGGCTTCAACCTGAAGGGCG
CCAACCTGTCCACCAACTTCAACGGCCAGAACACCGAGATCAACTCCCGCAACTT
CACCCGCCTGAAGAACTTCACCGGCCTGTTCGAGTTCTACAAGCTGCTGTGCGTG
CGCGGCATCATCCCCTTCAAGACCAAGTCCCTGGACGAGTAGGGGCCCAT

FIGURE 8B BoNT/E LC (SEQ ID NO: 2)

ATCTCGAGTCGCTAGCATGCCCAAGATCAACTCCTTCAACTACAACGACCCCGTG
AACGACCGCACCATCCTGTACATCAAGCCCGGCGGCTGCCAGGAGTTCTACAAG
TCCTTCAACATCATGAAGAACATCTGGATCATCCCCGAGCGCAACGTGATCGGCA
CCACCCCCCAGGACTTCCACCCCCCCACCTCCCTGAAGAACGGCGACTCCTCCTA
CTACGACCCCAACTACCTGCAGTCCGACGAGGAGAAGGACCGCTTCCTGAAGAT
CGTGACCAAGATCTTCAACCGCATCAACAACAACCTGTCCGGCGGCATCCTGCTG
GAGGAGCTGTCCAAGGCCAACCCCTACCTGGGCAACGACAACACCCCCGACAAC
CAGTTCCACATCGGCGACGCCTCCGCCGTGGAGATCAAGTTCTCCAAC<u>GGATCC</u>
CAGGACATCCTGCTGCCCAACGTGATCATCATGGGCGCCGAGCCCGACCTGTTCG
AGACCAACTCCTCCAACATCTCCCTGCGCAACAACTACATGCCCTCCAACCACGG
CTTCGGCTCCATCGCCATCGTGACCTTCTCCCCCGAGTACTCCTTCCGCTTCAACG
ACAACTCCATGAACGAGTTCATCCAGGACCCCGCCCTGACCCTGATGCACGAGCT
GATCCACTCCCTGCACGGCCTGTACGGCGCCAAGGGCATCACCACCAAGTACAC
CATCACCCAGAAGCAGAACCCCCTGATCACCAACATCCGCGGCACCAACATCGA
GGAGTTCCTGACCTTCGGCGGCACCGACCTGAACATCATCACCTCCGCCCAGTCC
AACGACATCTACACCAACCTGCTGGCCGACTACAAGAAGATCGCCTCCAAGCTG
TCCAAGGTGCAGGTGTCCAACCCCCTGCTGAACCCCTACAAGGACGTGTTCGAGG
CCAAGTACGGCCTGGACAAGGACGCC<u>*TCCGGA*</u>ATCTACTCCGTGAACATCAACA
AGTTCAACGACATCTTCAAGAAGCTGTACTCCTTCACCGAGTTCGACCTGGCCAC
CAAGTTCCAGGTGAAGTGCCGCCAGACCTACATCGGCCAGTACAAGTACTTCAA
GCTGTCCAACCTGCTGAACGACTCCATCTACAACATCTCCGAGGGCTACAACATC
AACAACCTGAAGGTGAACTTCCGCGGCCAGAACGCCAACCTGAACCCCCGCATC
ATCACCCCCATCACCGGCCGCGGCCTGGTGAAGAAGATCATCCGCTTCTGCAAGA
ACATCGTGTCCGTGAAGGGCATCCGCAAGTCCATCTGCATCGAGATCAACAACG
GCGAGCTGTTCTTCGTGGCCTCCGAGAACTCCTACAACGACGACAACATCAACAC
CTAGGGGCCCAT

SEQUENCE LISTING

<160> NUMBER OF SEQ ID NOS: 16

<210> SEQ ID NO 1
<211> LENGTH: 1359
<212> TYPE: DNA
<213> ORGANISM: Clostridium botulinum
<220> FEATURE:
<221> NAME/KEY: CDS
<222> LOCATION: (2)..(1348)

<400> SEQUENCE: 1

```
a tct cga gtc gct agc atg ccc ttc gtg aac aag cag ttc aac tac aag      49
  Ser Arg Val Ala Ser Met Pro Phe Val Asn Lys Gln Phe Asn Tyr Lys
  1               5                  10                  15 gac ccc gtg aac ggc gtg gac atc gcc tac atc aag atc ccc aac gcc        97
Asp Pro Val Asn Gly Val Asp Ile Ala Tyr Ile Lys Ile Pro Asn Ala
             20                  25                  30 ggc cag atg cag ccc gtg aag gcc ttc aag atc cac aac aag atc tgg       145
Gly Gln Met Gln Pro Val Lys Ala Phe Lys Ile His Asn Lys Ile Trp
         35                  40                  45 gtg atc ccc gag cgc gac acc ttc acc aac ccc gag gag ggc gac ctg       193
Val Ile Pro Glu Arg Asp Thr Phe Thr Asn Pro Glu Glu Gly Asp Leu
     50                  55                  60 aac ccc ccc ccc gag gcc aag cag gtg ccc gtg tcc tac tac gac tcc       241
Asn Pro Pro Pro Glu Ala Lys Gln Val Pro Val Ser Tyr Tyr Asp Ser
65                  70                  75                  80 acc tac ctg tcc acc gac aac gag aag gac aac tac ctg aag ggc gtg       289
Thr Tyr Leu Ser Thr Asp Asn Glu Lys Asp Asn Tyr Leu Lys Gly Val
                 85                  90                  95 acc aag ctg ttc gag cgc atc tac tcc acc gac ctg ggc cgc atg ctg       337
Thr Lys Leu Phe Glu Arg Ile Tyr Ser Thr Asp Leu Gly Arg Met Leu
            100                 105                 110 ctg acc tcc atc gtg cgc ggc atc ccc ttc tgg ggc ggc tcc acc atc       385
Leu Thr Ser Ile Val Arg Gly Ile Pro Phe Trp Gly Gly Ser Thr Ile
        115                 120                 125 gac acc gag ctg aag gtg atc gac acc aac tgc atc aac gtg atc cag       433
Asp Thr Glu Leu Lys Val Ile Asp Thr Asn Cys Ile Asn Val Ile Gln
    130                 135                 140 ccc gac gga tcc tac cgc tcc gag gag ctg aac ctg gtg atc atc ggc       481
Pro Asp Gly Ser Tyr Arg Ser Glu Glu Leu Asn Leu Val Ile Ile Gly
145                 150                 155                 160 ccc tcc gcc gac atc atc cag ttc gag tgc aag tcc ttc ggc cac gac       529
Pro Ser Ala Asp Ile Ile Gln Phe Glu Cys Lys Ser Phe Gly His Asp
                165                 170                 175 gtg ctg aac ctg acc cgc aac ggc tac ggc tcc acc cag tac atc cgc       577
Val Leu Asn Leu Thr Arg Asn Gly Tyr Gly Ser Thr Gln Tyr Ile Arg
            180                 185                 190 ttc tcc ccc gac ttc acc ttc ggc ttc gag gag tcc ctg gag gtg gac       625
Phe Ser Pro Asp Phe Thr Phe Gly Phe Glu Glu Ser Leu Glu Val Asp
        195                 200                 205 acc aac ccc ctg ctg ggc gcc ggc aag ttc gcc acc gac ccc gcc gtg       673
Thr Asn Pro Leu Leu Gly Ala Gly Lys Phe Ala Thr Asp Pro Ala Val
    210                 215                 220 acc ctg gcc cac gag ctg atc cac gcc gag cac cgc ctg tac ggc atc       721
Thr Leu Ala His Glu Leu Ile His Ala Glu His Arg Leu Tyr Gly Ile
225                 230                 235                 240 gcc atc aac ccc aac cgc gtg ttc aag gtg aac acc aac gcc tac tac       769
Ala Ile Asn Pro Asn Arg Val Phe Lys Val Asn Thr Asn Ala Tyr Tyr
                245                 250                 255 gag atg tcc ggc ctg gag gtg tcc ttc gag gag ctg cgc acc ttc ggc       817
Glu Met Ser Gly Leu Glu Val Ser Phe Glu Glu Leu Arg Thr Phe Gly
```

```
                                                        -continued

Glu Met Ser Gly Leu Glu Val Ser Phe Glu Leu Arg Thr Phe Gly
            260                 265                 270 ggc cac gac gcc aag ttc atc gac tcc ctg cag gag aac gag ttc cgc     865
Gly His Asp Ala Lys Phe Ile Asp Ser Leu Gln Glu Asn Glu Phe Arg
            275                 280                 285 ctg tac tac tac aac aag ttc aag gac gtg gcc tcc acc ctg aac aag     913
Leu Tyr Tyr Tyr Asn Lys Phe Lys Asp Val Ala Ser Thr Leu Asn Lys
        290                 295                 300 gcc aag tcc atc atc ggc acc acc gcc tcc ctg cag tac atg aag aac     961
Ala Lys Ser Ile Ile Gly Thr Thr Ala Ser Leu Gln Tyr Met Lys Asn
305                 310                 315                 320 gtg ttc aag gag aag tac ctg ctg tcc gag gac acc tcc gga aag ttc    1009
Val Phe Lys Glu Lys Tyr Leu Leu Ser Glu Asp Thr Ser Gly Lys Phe
                325                 330                 335 tcc gtg gac aag ctg aag ttc gac aag ctg tac aag atg ctg acc gag    1057
Ser Val Asp Lys Leu Lys Phe Asp Lys Leu Tyr Lys Met Leu Thr Glu
            340                 345                 350 atc tac acc gag gac aac ttc gtg aac ttc ttc aag gtg atc aac cgc    1105
Ile Tyr Thr Glu Asp Asn Phe Val Asn Phe Phe Lys Val Ile Asn Arg
        355                 360                 365 aag acc tac ctg aac ttc gac aag gcc gtg ttc cgc atc aac atc gtg    1153
Lys Thr Tyr Leu Asn Phe Asp Lys Ala Val Phe Arg Ile Asn Ile Val
    370                 375                 380 ccc gac gag aac tac acc atc aag gac ggc ttc aac ctg aag ggc gcc    1201
Pro Asp Glu Asn Tyr Thr Ile Lys Asp Gly Phe Asn Leu Lys Gly Ala
385                 390                 395                 400 aac ctg tcc acc aac ttc aac ggc cag aac acc gag atc aac tcc cgc    1249
Asn Leu Ser Thr Asn Phe Asn Gly Gln Asn Thr Glu Ile Asn Ser Arg
                405                 410                 415 aac ttc acc cgc ctg aag aac ttc acc ggc ctg ttc gag ttc tac aag    1297
Asn Phe Thr Arg Leu Lys Asn Phe Thr Gly Leu Phe Glu Phe Tyr Lys
            420                 425                 430 ctg ctg tgc gtg cgc ggc atc atc ccc ttc aag acc aag tcc ctg gac    1345
Leu Leu Cys Val Arg Gly Ile Ile Pro Phe Lys Thr Lys Ser Leu Asp
        435                 440                 445 gag tagggccca t                                                    1359
Glu

<210> SEQ ID NO 2
<211> LENGTH: 449
<212> TYPE: PRT
<213> ORGANISM: Clostridium botulinum

<400> SEQUENCE: 2

Ser Arg Val Ala Ser Met Pro Phe Val Asn Lys Gln Phe Asn Tyr Lys
1               5                   10                  15

Asp Pro Val Asn Gly Val Asp Ile Ala Tyr Ile Lys Ile Pro Asn Ala
            20                  25                  30

Gly Gln Met Gln Pro Val Lys Ala Phe Lys Ile His Asn Lys Ile Trp
        35                  40                  45

Val Ile Pro Glu Arg Asp Thr Phe Thr Asn Pro Glu Glu Gly Asp Leu
    50                  55                  60

Asn Pro Pro Pro Glu Ala Lys Gln Val Pro Val Ser Tyr Tyr Asp Ser
65                  70                  75                  80

Thr Tyr Leu Ser Thr Asp Asn Glu Lys Asp Asn Tyr Leu Lys Gly Val
                85                  90                  95

Thr Lys Leu Phe Glu Arg Ile Tyr Ser Thr Asp Leu Gly Arg Met Leu
            100                 105                 110

Leu Thr Ser Ile Val Arg Gly Ile Pro Phe Trp Gly Gly Ser Thr Ile
```

-continued

```
            115                 120                 125
Asp Thr Glu Leu Lys Val Ile Asp Thr Asn Cys Ile Asn Val Ile Gln
130                 135                 140

Pro Asp Gly Ser Tyr Arg Ser Glu Glu Leu Asn Leu Val Ile Ile Gly
145                 150                 155                 160

Pro Ser Ala Asp Ile Ile Gln Phe Glu Cys Lys Ser Phe Gly His Asp
                165                 170                 175

Val Leu Asn Leu Thr Arg Asn Gly Tyr Gly Ser Thr Gln Tyr Ile Arg
                180                 185                 190

Phe Ser Pro Asp Phe Thr Phe Gly Phe Glu Glu Ser Leu Glu Val Asp
            195                 200                 205

Thr Asn Pro Leu Leu Gly Ala Gly Lys Phe Ala Thr Asp Pro Ala Val
210                 215                 220

Thr Leu Ala His Glu Leu Ile His Ala Glu His Arg Leu Tyr Gly Ile
225                 230                 235                 240

Ala Ile Asn Pro Asn Arg Val Phe Lys Val Asn Thr Asn Ala Tyr Tyr
                245                 250                 255

Glu Met Ser Gly Leu Glu Val Ser Phe Glu Glu Leu Arg Thr Phe Gly
                260                 265                 270

Gly His Asp Ala Lys Phe Ile Asp Ser Leu Gln Glu Asn Glu Phe Arg
            275                 280                 285

Leu Tyr Tyr Tyr Asn Lys Phe Lys Asp Val Ala Ser Thr Leu Asn Lys
290                 295                 300

Ala Lys Ser Ile Ile Gly Thr Thr Ala Ser Leu Gln Tyr Met Lys Asn
305                 310                 315                 320

Val Phe Lys Glu Lys Tyr Leu Leu Ser Glu Asp Thr Ser Gly Lys Phe
                325                 330                 335

Ser Val Asp Lys Leu Lys Phe Asp Lys Leu Tyr Lys Met Leu Thr Glu
                340                 345                 350

Ile Tyr Thr Glu Asp Asn Phe Val Asn Phe Phe Lys Val Ile Asn Arg
            355                 360                 365

Lys Thr Tyr Leu Asn Phe Asp Lys Ala Val Phe Arg Ile Asn Ile Val
370                 375                 380

Pro Asp Glu Asn Tyr Thr Ile Lys Asp Gly Phe Asn Leu Lys Gly Ala
385                 390                 395                 400

Asn Leu Ser Thr Asn Phe Asn Gly Gln Asn Thr Glu Ile Asn Ser Arg
                405                 410                 415

Asn Phe Thr Arg Leu Lys Asn Phe Thr Gly Leu Phe Glu Phe Tyr Lys
                420                 425                 430

Leu Leu Cys Val Arg Gly Ile Ile Pro Phe Lys Thr Lys Ser Leu Asp
            435                 440                 445

Glu
```

```
<210> SEQ ID NO 3
<211> LENGTH: 1377
<212> TYPE: DNA
<213> ORGANISM: Clostridium botulinum
<220> FEATURE:
<221> NAME/KEY: CDS
<222> LOCATION: (2)..(1366)

<400> SEQUENCE: 3 a tct cga gtc gct agc atg ccc aag atc aac tcc ttc aac tac aac gac       49
  Ser Arg Val Ala Ser Met Pro Lys Ile Asn Ser Phe Asn Tyr Asn Asp
  1               5                  10                  15 ccc gtg aac gac cgc acc atc ctg tac atc aag ccc ggc ggc tgc cag          97
```

```
                Pro Val Asn Asp Arg Thr Ile Leu Tyr Ile Lys Pro Gly Gly Cys Gln
                                20              25                  30 gag ttc tac aag tcc ttc aac atc atg aag aac atc tgg atc atc ccc           145
Glu Phe Tyr Lys Ser Phe Asn Ile Met Lys Asn Ile Trp Ile Ile Pro
             35                  40                  45 gag cgc aac gtg atc ggc acc acc ccc cag gac ttc cac ccc ccc acc           193
Glu Arg Asn Val Ile Gly Thr Thr Pro Gln Asp Phe His Pro Pro Thr
         50                  55                  60 tcc ctg aag aac ggc gac tcc tcc tac tac gac ccc aac tac ctg cag           241
Ser Leu Lys Asn Gly Asp Ser Ser Tyr Tyr Asp Pro Asn Tyr Leu Gln
65                  70                  75                  80 tcc gac gag gag aag gac cgc ttc ctg aag atc gtg acc aag atc ttc           289
Ser Asp Glu Glu Lys Asp Arg Phe Leu Lys Ile Val Thr Lys Ile Phe
                 85                  90                  95 aac cgc atc aac aac aac ctg tcc ggc ggc atc ctg ctg gag gag ctg           337
Asn Arg Ile Asn Asn Asn Leu Ser Gly Gly Ile Leu Leu Glu Glu Leu
            100                 105                 110 tcc aag gcc aac ccc tac ctg ggc aac gac aac acc ccc gac aac cag           385
Ser Lys Ala Asn Pro Tyr Leu Gly Asn Asp Asn Thr Pro Asp Asn Gln
        115                 120                 125 ttc cac atc ggc gac gcc tcc gcc gtg gag atc aag ttc tcc aac gga           433
Phe His Ile Gly Asp Ala Ser Ala Val Glu Ile Lys Phe Ser Asn Gly
    130                 135                 140 tcc cag gac atc ctg ctg ccc aac gtg atc atc atg ggc gcc gag ccc           481
Ser Gln Asp Ile Leu Leu Pro Asn Val Ile Ile Met Gly Ala Glu Pro
145                 150                 155                 160 gac ctg ttc gag acc aac tcc tcc aac atc tcc ctg cgc aac aac tac           529
Asp Leu Phe Glu Thr Asn Ser Ser Asn Ile Ser Leu Arg Asn Asn Tyr
                165                 170                 175 atg ccc tcc aac cac ggc ttc ggc tcc atc gcc atc gtg acc ttc tcc           577
Met Pro Ser Asn His Gly Phe Gly Ser Ile Ala Ile Val Thr Phe Ser
            180                 185                 190 ccc gag tac tcc ttc cgc ttc aac gac aac tcc atg aac gag ttc atc           625
Pro Glu Tyr Ser Phe Arg Phe Asn Asp Asn Ser Met Asn Glu Phe Ile
        195                 200                 205 cag gac ccc gcc ctg acc ctg atg cac gag ctg atc cac tcc ctg cac           673
Gln Asp Pro Ala Leu Thr Leu Met His Glu Leu Ile His Ser Leu His
    210                 215                 220 ggc ctg tac ggc gcc aag ggc atc acc acc aag tac acc atc acc cag           721
Gly Leu Tyr Gly Ala Lys Gly Ile Thr Thr Lys Tyr Thr Ile Thr Gln
225                 230                 235                 240 aag cag aac ccc ctg atc acc aac atc cgc ggc acc aac atc gag gag           769
Lys Gln Asn Pro Leu Ile Thr Asn Ile Arg Gly Thr Asn Ile Glu Glu
                245                 250                 255 ttc ctg acc ttc ggc ggc acc gac ctg aac atc atc acc tcc gcc cag           817
Phe Leu Thr Phe Gly Gly Thr Asp Leu Asn Ile Ile Thr Ser Ala Gln
            260                 265                 270 tcc aac gac atc tac acc aac ctg ctg gcc gac tac aag aag atc gcc           865
Ser Asn Asp Ile Tyr Thr Asn Leu Leu Ala Asp Tyr Lys Lys Ile Ala
        275                 280                 285 tcc aag ctg tcc aag gtg cag gtg tcc aac ccc ctg ctg aac ccc tac           913
Ser Lys Leu Ser Lys Val Gln Val Ser Asn Pro Leu Leu Asn Pro Tyr
    290                 295                 300 aag gac gtg ttc gag gcc aag tac ggc ctg gac aag gac gcc tcc gga           961
Lys Asp Val Phe Glu Ala Lys Tyr Gly Leu Asp Lys Asp Ala Ser Gly
305                 310                 315                 320 atc tac tcc gtg aac atc aac aag ttc aac gac atc ttc aag aag ctg          1009
Ile Tyr Ser Val Asn Ile Asn Lys Phe Asn Asp Ile Phe Lys Lys Leu
                325                 330                 335 tac tcc ttc acc gag ttc gac ctg gcc acc aag ttc cag gtg aag tgc          1057
```

-continued

```
                Tyr Ser Phe Thr Glu Phe Asp Leu Ala Thr Lys Phe Gln Val Lys Cys
                            340                 345                 350 cgc cag acc tac atc ggc cag tac aag tac ttc aag ctg tcc aac ctg        1105
Arg Gln Thr Tyr Ile Gly Gln Tyr Lys Tyr Phe Lys Leu Ser Asn Leu
            355                 360                 365 ctg aac gac tcc atc tac aac atc tcc gag ggc tac aac atc aac aac        1153
Leu Asn Asp Ser Ile Tyr Asn Ile Ser Glu Gly Tyr Asn Ile Asn Asn
        370                 375                 380 ctg aag gtg aac ttc cgc ggc cag aac gcc aac ctg aac ccc cgc atc        1201
Leu Lys Val Asn Phe Arg Gly Gln Asn Ala Asn Leu Asn Pro Arg Ile
385                 390                 395                 400 atc acc ccc atc acc ggc cgc ggc ctg gtg aag aag atc atc cgc ttc        1249
Ile Thr Pro Ile Thr Gly Arg Gly Leu Val Lys Lys Ile Ile Arg Phe
                405                 410                 415 tgc aag aac atc gtg tcc gtg aag ggc atc cgc aag tcc atc tgc atc        1297
Cys Lys Asn Ile Val Ser Val Lys Gly Ile Arg Lys Ser Ile Cys Ile
            420                 425                 430 gag atc aac aac ggc gag ctg ttc ttc gtg gcc tcc gag aac tcc tac        1345
Glu Ile Asn Asn Gly Glu Leu Phe Phe Val Ala Ser Glu Asn Ser Tyr
        435                 440                 445 aac gac gac aac atc aac acc tagggggccca t                              1377
Asn Asp Asp Asn Ile Asn Thr
    450                 455

<210> SEQ ID NO 4
<211> LENGTH: 455
<212> TYPE: PRT
<213> ORGANISM: Clostridium botulinum

<400> SEQUENCE: 4

Ser Arg Val Ala Ser Met Pro Lys Ile Asn Ser Phe Asn Tyr Asn Asp
1               5                   10                  15

Pro Val Asn Asp Arg Thr Ile Leu Tyr Ile Lys Pro Gly Gly Cys Gln
                20                  25                  30

Glu Phe Tyr Lys Ser Phe Asn Ile Met Lys Asn Ile Trp Ile Ile Pro
            35                  40                  45

Glu Arg Asn Val Ile Gly Thr Thr Pro Gln Asp Phe His Pro Pro Thr
        50                  55                  60

Ser Leu Lys Asn Gly Asp Ser Ser Tyr Tyr Asp Pro Asn Tyr Leu Gln
65                  70                  75                  80

Ser Asp Glu Glu Lys Asp Arg Phe Leu Lys Ile Val Thr Lys Ile Phe
                85                  90                  95

Asn Arg Ile Asn Asn Asn Leu Ser Gly Gly Ile Leu Leu Glu Glu Leu
            100                 105                 110

Ser Lys Ala Asn Pro Tyr Leu Gly Asn Asp Asn Thr Pro Asp Asn Gln
        115                 120                 125

Phe His Ile Gly Asp Ala Ser Ala Val Glu Ile Lys Phe Ser Asn Gly
    130                 135                 140

Ser Gln Asp Ile Leu Leu Pro Asn Val Ile Ile Met Gly Ala Glu Pro
145                 150                 155                 160

Asp Leu Phe Glu Thr Asn Ser Ser Asn Ile Ser Leu Arg Asn Asn Tyr
                165                 170                 175

Met Pro Ser Asn His Gly Phe Gly Ser Ile Ala Ile Val Thr Phe Ser
            180                 185                 190

Pro Glu Tyr Ser Phe Arg Phe Asn Asp Asn Ser Met Asn Glu Phe Ile
        195                 200                 205

Gln Asp Pro Ala Leu Thr Leu Met His Glu Leu Ile His Ser Leu His
    210                 215                 220
```

```
Gly Leu Tyr Gly Ala Lys Gly Ile Thr Thr Lys Tyr Thr Ile Thr Gln
225                 230                 235                 240

Lys Gln Asn Pro Leu Ile Thr Asn Ile Arg Gly Thr Asn Ile Glu Glu
            245                 250                 255

Phe Leu Thr Phe Gly Gly Thr Asp Leu Asn Ile Ile Thr Ser Ala Gln
        260                 265                 270

Ser Asn Asp Ile Tyr Thr Asn Leu Leu Ala Asp Tyr Lys Lys Ile Ala
    275                 280                 285

Ser Lys Leu Ser Lys Val Gln Val Ser Asn Pro Leu Leu Asn Pro Tyr
290                 295                 300

Lys Asp Val Phe Glu Ala Lys Tyr Gly Leu Asp Lys Asp Ala Ser Gly
305                 310                 315                 320

Ile Tyr Ser Val Asn Ile Asn Lys Phe Asn Asp Ile Phe Lys Lys Leu
                325                 330                 335

Tyr Ser Phe Thr Glu Phe Asp Leu Ala Thr Lys Phe Gln Val Lys Cys
            340                 345                 350

Arg Gln Thr Tyr Ile Gly Gln Tyr Lys Tyr Phe Lys Leu Ser Asn Leu
        355                 360                 365

Leu Asn Asp Ser Ile Tyr Asn Ile Ser Glu Gly Tyr Asn Ile Asn Asn
370                 375                 380

Leu Lys Val Asn Phe Arg Gly Gln Asn Ala Asn Leu Asn Pro Arg Ile
385                 390                 395                 400

Ile Thr Pro Ile Thr Gly Arg Gly Leu Val Lys Lys Ile Ile Arg Phe
                405                 410                 415

Cys Lys Asn Ile Val Ser Val Lys Gly Ile Arg Lys Ser Ile Cys Ile
            420                 425                 430

Glu Ile Asn Asn Gly Gly Leu Phe Phe Val Ala Ser Glu Asn Ser Tyr
        435                 440                 445

Asn Asp Asp Asn Ile Asn Thr
    450                 455

<210> SEQ ID NO 5
<211> LENGTH: 2436
<212> TYPE: DNA
<213> ORGANISM: Clostridium botulinum
<220> FEATURE:
<221> NAME/KEY: CDS
<222> LOCATION: (1)..(2436)

<400> SEQUENCE: 5 atg cca atc acc atc aac aac ttc aac tac tca gac cct gtc gac aac        48
Met Pro Ile Thr Ile Asn Asn Phe Asn Tyr Ser Asp Pro Val Asp Asn
1               5                   10                  15 aag aac att ctg tac ctg gac act cac ctg aac acc cta gct aac gag        96
Lys Asn Ile Leu Tyr Leu Asp Thr His Leu Asn Thr Leu Ala Asn Glu
            20                  25                  30 cct gag aag gcc ttt cgg atc acc gga aac atc tgg gtc atc cct gat       144
Pro Glu Lys Ala Phe Arg Ile Thr Gly Asn Ile Trp Val Ile Pro Asp
        35                  40                  45 cgt ttc tcc cgt aac tcc aac ccc aac ctg aac aag cct cct cgg gtc       192
Arg Phe Ser Arg Asn Ser Asn Pro Asn Leu Asn Lys Pro Pro Arg Val
50                  55                  60 acc agc cct aag agt ggt tac tac gac cct aac tac ctg agt acc gac       240
Thr Ser Pro Lys Ser Gly Tyr Tyr Asp Pro Asn Tyr Leu Ser Thr Asp
65                  70                  75                  80 tct gac aag gac acc ttc ctg aag gag atc atc aag ctg ttc aag cgt       288
Ser Asp Lys Asp Thr Phe Leu Lys Glu Ile Ile Lys Leu Phe Lys Arg
                85                  90                  95
```

| | | | | | | | | | | | | | | | | |
|---|---|---|---|---|---|---|---|---|---|---|---|---|---|---|---|---|
| atc | aac | tcc | cgt | gag | atc | gga | gag | gag | ctc | atc | tac | aga | ctt | tcg | acc | 336 |
| Ile | Asn | Ser | Arg | Glu | Ile | Gly | Glu | Glu | Leu | Ile | Tyr | Arg | Leu | Ser | Thr | |
| | | 100 | | | | 105 | | | | 110 | | | | | | |
| gat | atc | ccc | ttc | cct | ggt | aac | aac | aat | act | cca | atc | aac | acc | ttc | gac | 384 |
| Asp | Ile | Pro | Phe | Pro | Gly | Asn | Asn | Asn | Thr | Pro | Ile | Asn | Thr | Phe | Asp | |
| | | | 115 | | | | 120 | | | | 125 | | | | | |
| ttc | gac | gtc | gac | ttc | aac | tcc | gtc | gac | gtc | aag | act | cgg | cag | ggt | aac | 432 |
| Phe | Asp | Val | Asp | Phe | Asn | Ser | Val | Asp | Val | Lys | Thr | Arg | Gln | Gly | Asn | |
| | 130 | | | | | 135 | | | | | 140 | | | | | |
| aac | tgg | gtt | aag | act | ggt | agc | atc | aac | cct | tcc | gtc | atc | atc | act | gga | 480 |
| Asn | Trp | Val | Lys | Thr | Gly | Ser | Ile | Asn | Pro | Ser | Val | Ile | Ile | Thr | Gly | |
| 145 | | | | | 150 | | | | | 155 | | | | | 160 | |
| cct | cgt | gag | aac | atc | atc | gac | cca | gag | act | tcc | acg | ttc | aag | ctg | act | 528 |
| Pro | Arg | Glu | Asn | Ile | Ile | Asp | Pro | Glu | Thr | Ser | Thr | Phe | Lys | Leu | Thr | |
| | | | | 165 | | | | | 170 | | | | | 175 | | |
| aac | aac | acc | ttc | gcg | gct | caa | gaa | gga | ttc | ggt | gct | ctg | tca | atc | atc | 576 |
| Asn | Asn | Thr | Phe | Ala | Ala | Gln | Glu | Gly | Phe | Gly | Ala | Leu | Ser | Ile | Ile | |
| | | | 180 | | | | 185 | | | | 190 | | | | | |
| tcc | atc | tca | cct | cgt | ttc | atg | ctg | acc | tac | tcg | aac | gca | acc | aac | gac | 624 |
| Ser | Ile | Ser | Pro | Arg | Phe | Met | Leu | Thr | Tyr | Ser | Asn | Ala | Thr | Asn | Asp | |
| | | 195 | | | | | 200 | | | | | 205 | | | | |
| gtc | gga | gag | ggt | agg | ttc | tct | aag | tct | gag | ttc | tgc | atg | gac | cca | atc | 672 |
| Val | Gly | Glu | Gly | Arg | Phe | Ser | Lys | Ser | Glu | Phe | Cys | Met | Asp | Pro | Ile | |
| | 210 | | | | | 215 | | | | | 220 | | | | | |
| ctg | atc | ctg | atg | cat | gag | ctg | aac | cat | gca | atg | cac | aac | ctg | tac | gga | 720 |
| Leu | Ile | Leu | Met | His | Glu | Leu | Asn | His | Ala | Met | His | Asn | Leu | Tyr | Gly | |
| 225 | | | | | 230 | | | | | 235 | | | | | 240 | |
| atc | gct | atc | cca | aac | gac | cag | acc | atc | tcc | tcc | gtg | acc | tcc | aac | atc | 768 |
| Ile | Ala | Ile | Pro | Asn | Asp | Gln | Thr | Ile | Ser | Ser | Val | Thr | Ser | Asn | Ile | |
| | | | | 245 | | | | | 250 | | | | | 255 | | |
| ttc | tac | tcc | cag | tac | aac | gtg | aag | ctg | gag | tac | gca | gag | atc | tac | gct | 816 |
| Phe | Tyr | Ser | Gln | Tyr | Asn | Val | Lys | Leu | Glu | Tyr | Ala | Glu | Ile | Tyr | Ala | |
| | | | 260 | | | | | 265 | | | | | 270 | | | |
| ttc | gga | ggt | cca | act | atc | gac | ctt | atc | cct | aag | tcc | gct | agg | aag | tac | 864 |
| Phe | Gly | Gly | Pro | Thr | Ile | Asp | Leu | Ile | Pro | Lys | Ser | Ala | Arg | Lys | Tyr | |
| | | 275 | | | | | 280 | | | | | 285 | | | | |
| ttc | gag | gag | aag | gct | ttg | gat | tac | tac | aga | tcc | atc | gct | aag | aga | ctg | 912 |
| Phe | Glu | Glu | Lys | Ala | Leu | Asp | Tyr | Tyr | Arg | Ser | Ile | Ala | Lys | Arg | Leu | |
| | 290 | | | | | 295 | | | | | 300 | | | | | |
| aac | agt | atc | acc | acc | gca | aac | cct | tcc | agc | ttc | aac | aag | tac | atc | ggt | 960 |
| Asn | Ser | Ile | Thr | Thr | Ala | Asn | Pro | Ser | Ser | Phe | Asn | Lys | Tyr | Ile | Gly | |
| 305 | | | | | 310 | | | | | 315 | | | | | 320 | |
| gag | tac | aag | cag | aag | ctg | atc | aga | aag | tac | cgt | ttc | gtc | gtc | gag | tct | 1008 |
| Glu | Tyr | Lys | Gln | Lys | Leu | Ile | Arg | Lys | Tyr | Arg | Phe | Val | Val | Glu | Ser | |
| | | | | 325 | | | | | 330 | | | | | 335 | | |
| tca | ggt | gag | gtc | aca | gta | aac | cgt | aac | aag | ttc | gtc | gag | ctg | tac | aac | 1056 |
| Ser | Gly | Glu | Val | Thr | Val | Asn | Arg | Asn | Lys | Phe | Val | Glu | Leu | Tyr | Asn | |
| | | | 340 | | | | | 345 | | | | | 350 | | | |
| gag | ctt | acc | cag | atc | ttc | aca | gag | ttc | aac | tac | gct | aag | atc | tac | aac | 1104 |
| Glu | Leu | Thr | Gln | Ile | Phe | Thr | Glu | Phe | Asn | Tyr | Ala | Lys | Ile | Tyr | Asn | |
| | | 355 | | | | | 360 | | | | | 365 | | | | |
| gtc | cag | aac | agg | aag | atc | tac | ctg | tcc | aac | gtg | tac | act | ccg | gtg | acg | 1152 |
| Val | Gln | Asn | Arg | Lys | Ile | Tyr | Leu | Ser | Asn | Val | Tyr | Thr | Pro | Val | Thr | |
| | 370 | | | | | 375 | | | | | 380 | | | | | |
| gcg | aac | atc | ctg | gac | gac | aac | gtc | tac | gac | atc | cag | aac | gga | ttc | aac | 1200 |
| Ala | Asn | Ile | Leu | Asp | Asp | Asn | Val | Tyr | Asp | Ile | Gln | Asn | Gly | Phe | Asn | |
| 385 | | | | | 390 | | | | | 395 | | | | | 400 | |
| atc | cct | aag | tcc | aac | ctg | aac | gta | cta | ttc | atg | ggt | caa | aac | ctg | tct | 1248 |
| Ile | Pro | Lys | Ser | Asn | Leu | Asn | Val | Leu | Phe | Met | Gly | Gln | Asn | Leu | Ser | |
| | | | | 405 | | | | | 410 | | | | | 415 | | |

| | |
|---|---|
| cga aac cca gca ctg cgt aag gtc aac cct gag aac atg ctg tac ctg<br>Arg Asn Pro Ala Leu Arg Lys Val Asn Pro Glu Asn Met Leu Tyr Leu<br>420                            425                      430 | 1296 |
| ttc acc aag ttc tgc tcc ctg tac aac aag acc ctt gac tgt aga gag<br>Phe Thr Lys Phe Cys Ser Leu Tyr Asn Lys Thr Leu Asp Cys Arg Glu<br>           435                      440                      445 | 1344 |
| ctg ctg gtg aag aac act gac ctg cca ttc atc ggt gac atc agt gac<br>Leu Leu Val Lys Asn Thr Asp Leu Pro Phe Ile Gly Asp Ile Ser Asp<br>450                            455                      460 | 1392 |
| gtg aag act gac atc ttc ctg cgt aag gac atc aac gag gag act gag<br>Val Lys Thr Asp Ile Phe Leu Arg Lys Asp Ile Asn Glu Glu Thr Glu<br>465                            470                      475                      480 | 1440 |
| gtg atc tac tac cca gac aac gtg tca gta gac caa gtg atc ctc agt<br>Val Ile Tyr Tyr Pro Asp Asn Val Ser Val Asp Gln Val Ile Leu Ser<br>                      485                      490                      495 | 1488 |
| aag aac acc tcc gag cat gga caa cta gac ctg ctc tac cct agt atc<br>Lys Asn Thr Ser Glu His Gly Gln Leu Asp Leu Leu Tyr Pro Ser Ile<br>500                            505                      510 | 1536 |
| gac agt gag agt gag atc ctg cca ggg gag aat caa gtc ttc tac gac<br>Asp Ser Glu Ser Glu Ile Leu Pro Gly Glu Asn Gln Val Phe Tyr Asp<br>           515                      520                      525 | 1584 |
| aac cgt acc cag aac gtg gac tac ctg aac tcc tac tac cta gag<br>Asn Arg Thr Gln Asn Val Asp Tyr Leu Asn Ser Tyr Tyr Tyr Leu Glu<br>530                            535                      540 | 1632 |
| tct cag aag ctg agt gac aac gtg gag gac ttc act ttc acg cgt tca<br>Ser Gln Lys Leu Ser Asp Asn Val Glu Asp Phe Thr Phe Thr Arg Ser<br>545                            550                      555                      560 | 1680 |
| atc gag gag gct ctg gac aac agt gca aag gtg tac act tac ttc cct<br>Ile Glu Glu Ala Leu Asp Asn Ser Ala Lys Val Tyr Thr Tyr Phe Pro<br>                      565                      570                      575 | 1728 |
| acc ctg gct aac aag gtg aat gcc ggt gtg caa ggt ggt ctg ttc ctg<br>Thr Leu Ala Asn Lys Val Asn Ala Gly Val Gln Gly Gly Leu Phe Leu<br>                    580                      585                      590 | 1776 |
| atg tgg gca aac gac gtg gtt gag gac ttc act acc aac atc ctg cgt<br>Met Trp Ala Asn Asp Val Val Glu Asp Phe Thr Thr Asn Ile Leu Arg<br>           595                      600                      605 | 1824 |
| aag gac aca ctg gac aag atc tca gat gtg tca gct atc atc ccc tac<br>Lys Asp Thr Leu Asp Lys Ile Ser Asp Val Ser Ala Ile Ile Pro Tyr<br>610                            615                      620 | 1872 |
| atc gga ccc gca ctg aac atc tcc aac tct gtg cgt cgt gga aac ttc<br>Ile Gly Pro Ala Leu Asn Ile Ser Asn Ser Val Arg Arg Gly Asn Phe<br>625                            630                      635                      640 | 1920 |
| act gag gca ttc gca gtc act ggt gtc acc atc ctg ctg gag gca ttc<br>Thr Glu Ala Phe Ala Val Thr Gly Val Thr Ile Leu Leu Glu Ala Phe<br>                      645                      650                      655 | 1968 |
| cct gag ttc aca atc cct gct ctg ggt gca ttc gtg atc tac agt aag<br>Pro Glu Phe Thr Ile Pro Ala Leu Gly Ala Phe Val Ile Tyr Ser Lys<br>           660                      665                      670 | 2016 |
| gtc cag gag cga aac gag atc atc aag acc atc gac aac tgt ctg gag<br>Val Gln Glu Arg Asn Glu Ile Ile Lys Thr Ile Asp Asn Cys Leu Glu<br>675                            680                      685 | 2064 |
| cag agg atc aag aga tgg aag gac tcc tac gag tgg atg atg gga acg<br>Gln Arg Ile Lys Arg Trp Lys Asp Ser Tyr Glu Trp Met Met Gly Thr<br>           690                      695                      700 | 2112 |
| tgg ttg tcc agg atc atc acc cag ttc aac aac atc tcc tac cag atg<br>Trp Leu Ser Arg Ile Ile Thr Gln Phe Asn Asn Ile Ser Tyr Gln Met<br>705                            710                      715                      720 | 2160 |
| tac gac tcc ctg aac tac cag gca ggt gca atc aag gct aag atc gac<br>Tyr Asp Ser Leu Asn Tyr Gln Ala Gly Ala Ile Lys Ala Lys Ile Asp<br>                      725                      730                      735 | 2208 |

```
ctg gag tac aag aag tac tcc gga agc gac aag gag aac atc aag agc    2256
Leu Glu Tyr Lys Lys Tyr Ser Gly Ser Asp Lys Glu Asn Ile Lys Ser
        740             745                 750 cag gtt gag aac ctg aag aac agt ctg gac gtc aag atc tcg gag gca    2304
Gln Val Glu Asn Leu Lys Asn Ser Leu Asp Val Lys Ile Ser Glu Ala
            755                 760                 765 atg aac aac atc aac aag ttc atc cga gag tgc tcc gtc acc tac ctg    2352
Met Asn Asn Ile Asn Lys Phe Ile Arg Glu Cys Ser Val Thr Tyr Leu
770                 775                 780 ttc aag aac atg ctg cct aag gtc atc gac gag ctg aac gag ttc gac    2400
Phe Lys Asn Met Leu Pro Lys Val Ile Asp Glu Leu Asn Glu Phe Asp
785                 790                 795                 800 cga aac acc aag gca aag ctg atc aac ctg atc gac                    2436
Arg Asn Thr Lys Ala Lys Leu Ile Asn Leu Ile Asp
                805                 810

<210> SEQ ID NO 6
<211> LENGTH: 812
<212> TYPE: PRT
<213> ORGANISM: Clostridium botulinum

<400> SEQUENCE: 6

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
        35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270
```

-continued

```
Phe Gly Gly Pro Thr Ile Asp Leu Ile Pro Lys Ser Ala Arg Lys Tyr
            275                 280                 285

Phe Glu Glu Lys Ala Leu Asp Tyr Tyr Arg Ser Ile Ala Lys Arg Leu
            290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                    325                 330                 335

Ser Gly Glu Val Thr Val Asn Arg Asn Lys Phe Val Glu Leu Tyr Asn
                340                 345                 350

Glu Leu Thr Gln Ile Phe Thr Glu Phe Asn Tyr Ala Lys Ile Tyr Asn
            355                 360                 365

Val Gln Asn Arg Lys Ile Tyr Leu Ser Asn Val Tyr Thr Pro Val Thr
            370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                    405                 410                 415

Arg Asn Pro Ala Leu Arg Lys Val Asn Pro Glu Asn Met Leu Tyr Leu
                420                 425                 430

Phe Thr Lys Phe Cys Ser Leu Tyr Asn Lys Thr Leu Asp Cys Arg Glu
            435                 440                 445

Leu Leu Val Lys Asn Thr Asp Leu Pro Phe Ile Gly Asp Ile Ser Asp
450                 455                 460

Val Lys Thr Asp Ile Phe Leu Arg Lys Asp Ile Asn Glu Glu Thr Glu
465                 470                 475                 480

Val Ile Tyr Tyr Pro Asp Asn Val Ser Val Asp Gln Val Ile Leu Ser
                    485                 490                 495

Lys Asn Thr Ser Glu His Gly Gln Leu Asp Leu Leu Tyr Pro Ser Ile
                500                 505                 510

Asp Ser Glu Ser Glu Ile Leu Pro Gly Glu Asn Gln Val Phe Tyr Asp
            515                 520                 525

Asn Arg Thr Gln Asn Val Asp Tyr Leu Asn Ser Tyr Tyr Tyr Leu Glu
            530                 535                 540

Ser Gln Lys Leu Ser Asp Asn Val Glu Asp Phe Thr Phe Thr Arg Ser
545                 550                 555                 560

Ile Glu Glu Ala Leu Asp Asn Ser Ala Lys Val Tyr Thr Tyr Phe Pro
                    565                 570                 575

Thr Leu Ala Asn Lys Val Asn Ala Gly Val Gln Gly Gly Leu Phe Leu
                580                 585                 590

Met Trp Ala Asn Asp Val Val Glu Asp Phe Thr Thr Asn Ile Leu Arg
            595                 600                 605

Lys Asp Thr Leu Asp Lys Ile Ser Asp Val Ser Ala Ile Ile Pro Tyr
            610                 615                 620

Ile Gly Pro Ala Leu Asn Ile Ser Asn Ser Val Arg Arg Gly Asn Phe
625                 630                 635                 640

Thr Glu Ala Phe Ala Val Thr Gly Val Thr Ile Leu Leu Glu Ala Phe
                    645                 650                 655

Pro Glu Phe Thr Ile Pro Ala Leu Gly Ala Phe Val Ile Tyr Ser Lys
                660                 665                 670

Val Gln Glu Arg Asn Glu Ile Ile Lys Thr Ile Asp Asn Cys Leu Glu
            675                 680                 685

Gln Arg Ile Lys Arg Trp Lys Asp Ser Tyr Glu Trp Met Met Gly Thr
            690                 695                 700
```

-continued

```
Trp Leu Ser Arg Ile Ile Thr Gln Phe Asn Asn Ile Ser Tyr Gln Met
705                 710                 715                 720

Tyr Asp Ser Leu Asn Tyr Gln Ala Gly Ala Ile Lys Ala Lys Ile Asp
            725                 730                 735

Leu Glu Tyr Lys Lys Tyr Ser Gly Ser Asp Lys Glu Asn Ile Lys Ser
        740                 745                 750

Gln Val Glu Asn Leu Lys Asn Ser Leu Asp Val Lys Ile Ser Glu Ala
    755                 760                 765

Met Asn Asn Ile Asn Lys Phe Ile Arg Glu Cys Ser Val Thr Tyr Leu
770                 775                 780

Phe Lys Asn Met Leu Pro Lys Val Ile Asp Glu Leu Asn Glu Phe Asp
785                 790                 795                 800

Arg Asn Thr Lys Ala Lys Leu Ile Asn Leu Ile Asp
            805                 810
```

<210> SEQ ID NO 7
<211> LENGTH: 2559
<212> TYPE: DNA
<213> ORGANISM: Clostridium botulinum
<220> FEATURE:
<221> NAME/KEY: CDS
<222> LOCATION: (1)..(2559)

<400> SEQUENCE: 7

```
atg cca gtt acc atc aac aac ttc aac tac aac gac cca atc gac aac      48
Met Pro Val Thr Ile Asn Asn Phe Asn Tyr Asn Asp Pro Ile Asp Asn
1               5                   10                  15 aac aac atc att atg atg gag cca cca ttc gct aga ggt acc ggt aga      96
Asn Asn Ile Ile Met Met Glu Pro Pro Phe Ala Arg Gly Thr Gly Arg
            20                  25                  30 tac tac aag gct ttc aag atc acc gac aga att tgg att att cca gag     144
Tyr Tyr Lys Ala Phe Lys Ile Thr Asp Arg Ile Trp Ile Ile Pro Glu
        35                  40                  45 aga tac act ttc ggt tac aag cca gag gac ttc aac aag tct tct ggt     192
Arg Tyr Thr Phe Gly Tyr Lys Pro Glu Asp Phe Asn Lys Ser Ser Gly
    50                  55                  60 att ttc aac aga gac gtc tgc gag tac tac gac cca gac tac ctg aac     240
Ile Phe Asn Arg Asp Val Cys Glu Tyr Tyr Asp Pro Asp Tyr Leu Asn
65                  70                  75                  80 acc aac gac aag aag aac atc ttc ctg cag acc atg atc aag ctg ttc     288
Thr Asn Asp Lys Lys Asn Ile Phe Leu Gln Thr Met Ile Lys Leu Phe
                85                  90                  95 aac aga atc aag tcc aag cca ttg ggt gag aag ctg ctg gag atg atc     336
Asn Arg Ile Lys Ser Lys Pro Leu Gly Glu Lys Leu Leu Glu Met Ile
            100                 105                 110 att aac ggt atc cca tac ctg ggt gac aga aga gtc cca ctg gag gag     384
Ile Asn Gly Ile Pro Tyr Leu Gly Asp Arg Arg Val Pro Leu Glu Glu
        115                 120                 125 ttc aac acc aac atc gcc tcc gtc acc gtc aac aag ctg atc tcc aac     432
Phe Asn Thr Asn Ile Ala Ser Val Thr Val Asn Lys Leu Ile Ser Asn
    130                 135                 140 ccg ggt gag gtc gag cgt aag aag ggc atc ttc gcc aac ctg atc atc     480
Pro Gly Glu Val Glu Arg Lys Lys Gly Ile Phe Ala Asn Leu Ile Ile
145                 150                 155                 160 ttc ggc cca ggt cca gtc ttg aac gag aac gag act att gac att ggc     528
Phe Gly Pro Gly Pro Val Leu Asn Glu Asn Glu Thr Ile Asp Ile Gly
                165                 170                 175 att caa aac cac ttc gcc tcc aga gag ggt ttc ggc ggt atc atg caa     576
Ile Gln Asn His Phe Ala Ser Arg Glu Gly Phe Gly Gly Ile Met Gln
            180                 185                 190
```

-continued

| | | |
|---|---|---|
| atg aag ttc tgt cca gag tac gtc tcc gtt ttc aac aac gtc caa gag<br>Met Lys Phe Cys Pro Glu Tyr Val Ser Val Phe Asn Asn Val Gln Glu<br>           195                  200                  205 | 624 |
| aac aag ggt gcc tcc atc ttc aac aga aga ggc tac ttc tcc gac cca<br>Asn Lys Gly Ala Ser Ile Phe Asn Arg Arg Gly Tyr Phe Ser Asp Pro<br>210                  215                  220 | 672 |
| gcc ttg atc ttg atg cac gag ttg atc cac gtc ttg cac ggt ttg tac<br>Ala Leu Ile Leu Met His Glu Leu Ile His Val Leu His Gly Leu Tyr<br>225                  230                  235                  240 | 720 |
| ggt atc aag gtc gac gac ttg cca att gtc cca aac gag aag aag ttc<br>Gly Ile Lys Val Asp Asp Leu Pro Ile Val Pro Asn Glu Lys Lys Phe<br>           245                  250                  255 | 768 |
| ttc atg cag tcc acc gac gcc atc cag gcc gag gag ctg tac acc ttc<br>Phe Met Gln Ser Thr Asp Ala Ile Gln Ala Glu Glu Leu Tyr Thr Phe<br>260                  265                  270 | 816 |
| ggt ggt cag gac cca tcc atc att acc cca tcc acc gac aag tcc atc<br>Gly Gly Gln Asp Pro Ser Ile Ile Thr Pro Ser Thr Asp Lys Ser Ile<br>           275                  280                  285 | 864 |
| tac gac aag gtc ttg cag aac ttc aga ggt atc gtc gat aga ctg aac<br>Tyr Asp Lys Val Leu Gln Asn Phe Arg Gly Ile Val Asp Arg Leu Asn<br>290                  295                  300 | 912 |
| aag gtc ttg gtc tgc atc tcc gac cca aac atc aac atc aac att tac<br>Lys Val Leu Val Cys Ile Ser Asp Pro Asn Ile Asn Ile Asn Ile Tyr<br>305                  310                  315                  320 | 960 |
| aag aac aag ttc aag gac aag tac aag ttc gtc gag gac tcc gag ggt<br>Lys Asn Lys Phe Lys Asp Lys Tyr Lys Phe Val Glu Asp Ser Glu Gly<br>           325                  330                  335 | 1008 |
| aag tac tcc atc gac gtc gag tcc ttc gac aag ctg tac aag tcc ctg<br>Lys Tyr Ser Ile Asp Val Glu Ser Phe Asp Lys Leu Tyr Lys Ser Leu<br>340                  345                  350 | 1056 |
| atg ttc ggt ttc acc gag acc aac atc gcc gag aac tac aag atc aag<br>Met Phe Gly Phe Thr Glu Thr Asn Ile Ala Glu Asn Tyr Lys Ile Lys<br>           355                  360                  365 | 1104 |
| acc aga gcc tcc tac ttc tcc gac tcc ctg cca cca gtc aag atc aag<br>Thr Arg Ala Ser Tyr Phe Ser Asp Ser Leu Pro Pro Val Lys Ile Lys<br>370                  375                  380 | 1152 |
| aac ttg ttg gac aac gaa atc tac act att gag gag ggt ttc aac att<br>Asn Leu Leu Asp Asn Glu Ile Tyr Thr Ile Glu Glu Gly Phe Asn Ile<br>385                  390                  395                  400 | 1200 |
| tcc gac aag gac atg gag aag gag tac aga ggt caa aac aag gct att<br>Ser Asp Lys Asp Met Glu Lys Glu Tyr Arg Gly Gln Asn Lys Ala Ile<br>           405                  410                  415 | 1248 |
| aac aag caa gct tac gag gag att tct aag gag cac ttg gct gtt tac<br>Asn Lys Gln Ala Tyr Glu Glu Ile Ser Lys Glu His Leu Ala Val Tyr<br>420                  425                  430 | 1296 |
| aag att caa atg tgt aag tct gtt aag gct cca gga atc tgt atc gac<br>Lys Ile Gln Met Cys Lys Ser Val Lys Ala Pro Gly Ile Cys Ile Asp<br>           435                  440                  445 | 1344 |
| gtc gac aac gag gac ttg ttc ttc atc gct gac aag aac tcc ttc tcc<br>Val Asp Asn Glu Asp Leu Phe Phe Ile Ala Asp Lys Asn Ser Phe Ser<br>450                  455                  460 | 1392 |
| gac gac ttg tcc aag aac gag aga atc gag tac aac acc cag tcc aac<br>Asp Asp Leu Ser Lys Asn Glu Arg Ile Glu Tyr Asn Thr Gln Ser Asn<br>465                  470                  475                  480 | 1440 |
| tac atc gag aac gac ttc cca atc aac gag ttg atc ttg gac acc gac<br>Tyr Ile Glu Asn Asp Phe Pro Ile Asn Glu Leu Ile Leu Asp Thr Asp<br>           485                  490                  495 | 1488 |
| ttg atc tcc aag atc gag ttg cca tcc gag aac acc gag tcc ttg act<br>Leu Ile Ser Lys Ile Glu Leu Pro Ser Glu Asn Thr Glu Ser Leu Thr<br>500                  505                  510 | 1536 |

```
gac ttc aac gtc gac gtc cca gtc tac gag aag caa cca gct atc aag    1584
Asp Phe Asn Val Asp Val Pro Val Tyr Glu Lys Gln Pro Ala Ile Lys
        515                 520                 525 aag att ttc acc gac gag aac acc atc ttc caa tac ctg tac tct cag    1632
Lys Ile Phe Thr Asp Glu Asn Thr Ile Phe Gln Tyr Leu Tyr Ser Gln
    530                 535                 540 acc ttc cct ttg gac atc aga gac atc tcc ttg acc tct tcc ttc gac    1680
Thr Phe Pro Leu Asp Ile Arg Asp Ile Ser Leu Thr Ser Ser Phe Asp
545                 550                 555                 560 gac gcc ctg ctg ttc tcc aac aag gtc tac tcc ttc ttc tcc atg gac    1728
Asp Ala Leu Leu Phe Ser Asn Lys Val Tyr Ser Phe Phe Ser Met Asp
            565                 570                 575 tac atc aag act gct aac aag gtc gtc gag gcc ggt ttg ttc gct ggt    1776
Tyr Ile Lys Thr Ala Asn Lys Val Val Glu Ala Gly Leu Phe Ala Gly
        580                 585                 590 tgg gtc aag cag atc gtc aac gat ttc gtc atc gag gct aac aag tcc    1824
Trp Val Lys Gln Ile Val Asn Asp Phe Val Ile Glu Ala Asn Lys Ser
    595                 600                 605 aac acc atg gac aag att gcc gac atc tcc ttg att gtc cca tac atc    1872
Asn Thr Met Asp Lys Ile Ala Asp Ile Ser Leu Ile Val Pro Tyr Ile
610                 615                 620 ggt ttg gcc ttg aac gtc ggt aac gag acc gcc aag ggt aac ttc gag    1920
Gly Leu Ala Leu Asn Val Gly Asn Glu Thr Ala Lys Gly Asn Phe Glu
            630                 635                 640
625 aac gct ttc gag atc gct ggt gcc tcc atc ttg ttg gag ttc atc cca    1968
Asn Ala Phe Glu Ile Ala Gly Ala Ser Ile Leu Leu Glu Phe Ile Pro
        645                 650                 655 gag ttg ttg atc cca gtc gtc ggt gcc ttc ttg ttg gag tcc tac atc    2016
Glu Leu Leu Ile Pro Val Val Gly Ala Phe Leu Leu Glu Ser Tyr Ile
    660                 665                 670 gac aac aag aac aag atc atc aag acc atc gac aac gct ttg acc aag    2064
Asp Asn Lys Asn Lys Ile Ile Lys Thr Ile Asp Asn Ala Leu Thr Lys
675                 680                 685 aga aac gag aag tgg tcc gac atg tac ggt ttg atc gtc gcc caa tgg    2112
Arg Asn Glu Lys Trp Ser Asp Met Tyr Gly Leu Ile Val Ala Gln Trp
            690                 695                 700 ttg tcc acc gtc aac acc caa ttc tac acc atc aag gag ggt atg tac    2160
Leu Ser Thr Val Asn Thr Gln Phe Tyr Thr Ile Lys Glu Gly Met Tyr
705                 710                 715                 720 aag gcc ttg aac tac cag gcc caa gct ttg gag gag atc atc aag tac    2208
Lys Ala Leu Asn Tyr Gln Ala Gln Ala Leu Glu Glu Ile Ile Lys Tyr
            725                 730                 735 aga tac aac atc tac tcc gag aag gag aag tcc aac att aac atc gac    2256
Arg Tyr Asn Ile Tyr Ser Glu Lys Glu Lys Ser Asn Ile Asn Ile Asp
        740                 745                 750 ttc aac gac atc aac tcc aag ctg aac gag ggt att aac cag gcc atc    2304
Phe Asn Asp Ile Asn Ser Lys Leu Asn Glu Gly Ile Asn Gln Ala Ile
    755                 760                 765 gac aac atc aac aac ttc atc aac ggt tgt tcc gtc tcc tac ttg atg    2352
Asp Asn Ile Asn Asn Phe Ile Asn Gly Cys Ser Val Ser Tyr Leu Met
770                 775                 780 aag aag atg att cca ttg gcc gtc gag aag ttg ttg gac ttc gac aac    2400
Lys Lys Met Ile Pro Leu Ala Val Glu Lys Leu Leu Asp Phe Asp Asn
            790                 795                 800
785 acc ctg aag aag aac ttg ttg aac tac atc gac gag aac aag ttg tac    2448
Thr Leu Lys Lys Asn Leu Leu Asn Tyr Ile Asp Glu Asn Lys Leu Tyr
        805                 810                 815 ttg atc ggt tcc gct gag tac gag aag tcc aag gtc aac aag tac ttg    2496
Leu Ile Gly Ser Ala Glu Tyr Glu Lys Ser Lys Val Asn Lys Tyr Leu
    820                 825                 830
```

```
aag acc atc atg cca ttc gac ttg tcc atc tac acc aac gac acc atc    2544
Lys Thr Ile Met Pro Phe Asp Leu Ser Ile Tyr Thr Asn Asp Thr Ile
        835                 840                 845 ttg atc gag atg ttc                                                2559
Leu Ile Glu Met Phe
    850
```

<210> SEQ ID NO 8
<211> LENGTH: 853
<212> TYPE: PRT
<213> ORGANISM: Clostridium botulinum

<400> SEQUENCE: 8

```
Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335
```

-continued

```
Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
            355                 360                 365

Thr Arg Ala Ser Tyr Phe Ser Asp Ser Leu Pro Pro Val Lys Ile Lys
            370                 375                 380

Asn Leu Leu Asp Asn Glu Ile Tyr Thr Ile Glu Gly Phe Asn Ile
385                 390                 395                 400

Ser Asp Lys Asp Met Glu Lys Glu Tyr Arg Gly Gln Asn Lys Ala Ile
                    405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
            435                 440                 445

Val Asp Asn Glu Asp Leu Phe Phe Ile Ala Asp Lys Asn Ser Phe Ser
450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
            515                 520                 525

Lys Ile Phe Thr Asp Glu Asn Thr Ile Phe Gln Tyr Leu Tyr Ser Gln
            530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Ser Met Asp
                    565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
            595                 600                 605

Asn Thr Met Asp Lys Ile Ala Asp Ile Ser Leu Ile Val Pro Tyr Ile
610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
            675                 680                 685

Arg Asn Glu Lys Trp Ser Asp Met Tyr Gly Leu Ile Val Ala Gln Trp
            690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                    725                 730                 735

Arg Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
            755                 760                 765
```

```
Asp Asn Ile Asn Asn Phe Ile Asn Gly Cys Ser Val Ser Tyr Leu Met
    770                 775                 780
Lys Lys Met Ile Pro Leu Ala Val Glu Lys Leu Leu Asp Phe Asp Asn
785                 790                 795                 800
Thr Leu Lys Lys Asn Leu Leu Asn Tyr Ile Asp Glu Asn Lys Leu Tyr
                805                 810                 815
Leu Ile Gly Ser Ala Glu Tyr Glu Lys Ser Lys Val Asn Lys Tyr Leu
            820                 825                 830
Lys Thr Ile Met Pro Phe Asp Leu Ser Ile Tyr Thr Asn Asp Thr Ile
        835                 840                 845
Leu Ile Glu Met Phe
    850

<210> SEQ ID NO 9
<211> LENGTH: 2475
<212> TYPE: DNA
<213> ORGANISM: Clostridium botulinum
<220> FEATURE:
<221> NAME/KEY: CDS
<222> LOCATION: (1)..(2475)

<400> SEQUENCE: 9
```

| | |
|---|---:|
| atg acc tgg cca gtc aag gac ttc aac tac tcc gac cca gtc aac gac<br>Met Thr Trp Pro Val Lys Asp Phe Asn Tyr Ser Asp Pro Val Asn Asp<br>1               5                   10                  15 | 48 |
| aac gac atc ttg tac ttg aga atc cca caa aac aag ttg atc acc acc<br>Asn Asp Ile Leu Tyr Leu Arg Ile Pro Gln Asn Lys Leu Ile Thr Thr<br>            20                  25                  30 | 96 |
| cca gtc aag gct ttc atg atc acc cag aac acc tgg gtt atc cca gag<br>Pro Val Lys Ala Phe Met Ile Thr Gln Asn Thr Trp Val Ile Pro Glu<br>        35                  40                  45 | 144 |
| aga ttc tcc tcc gac acc aac cca tcc ctg tcc aag cca cca aga cca<br>Arg Phe Ser Ser Asp Thr Asn Pro Ser Leu Ser Lys Pro Pro Arg Pro<br>    50                  55                  60 | 192 |
| acc tcc aag tac cag tct tac tac gac cca tct tac ttg tct acc gac<br>Thr Ser Lys Tyr Gln Ser Tyr Tyr Asp Pro Ser Tyr Leu Ser Thr Asp<br>65                  70                  75                  80 | 240 |
| gag caa aag gac acc ttc ttg aag ggt att atc aag ctg ttc aag aga<br>Glu Gln Lys Asp Thr Phe Leu Lys Gly Ile Ile Lys Leu Phe Lys Arg<br>                85                  90                  95 | 288 |
| atc aac gag aga gac atc ggt aag aag ttg atc aac tac ttg gtc gtt<br>Ile Asn Glu Arg Asp Ile Gly Lys Lys Leu Ile Asn Tyr Leu Val Val<br>            100                 105                 110 | 336 |
| ggt tcc cca ttc atg ggt gac tcc tct acc cca gag gac acc ttc gac<br>Gly Ser Pro Phe Met Gly Asp Ser Ser Thr Pro Glu Asp Thr Phe Asp<br>        115                 120                 125 | 384 |
| ttc acc aga cac acc acc aac att gcc gtc gag aag ttc gag aac ggt<br>Phe Thr Arg His Thr Thr Asn Ile Ala Val Glu Lys Phe Glu Asn Gly<br>    130                 135                 140 | 432 |
| tcc tgg aag gtc acc aac atc atc acc cca tct gtt ttg atc ttc ggt<br>Ser Trp Lys Val Thr Asn Ile Ile Thr Pro Ser Val Leu Ile Phe Gly<br>145                 150                 155                 160 | 480 |
| cca ttg cca aac atc ttg gac tac acc gcc tcc ctg acc ttg caa ggt<br>Pro Leu Pro Asn Ile Leu Asp Tyr Thr Ala Ser Leu Thr Leu Gln Gly<br>                165                 170                 175 | 528 |
| cag caa tcc aac cca tcc ttc gag ggt ttc ggt acc ctg tct att ttg<br>Gln Gln Ser Asn Pro Ser Phe Glu Gly Phe Gly Thr Leu Ser Ile Leu<br>            180                 185                 190 | 576 |
| aag gtc gct cca gag ttc ttg ttg acc ttc tcc gac gtc acc tcc aac<br>Lys Val Ala Pro Glu Phe Leu Leu Thr Phe Ser Asp Val Thr Ser Asn | 624 |

```
                195                 200                 205
caa tcc tcc gcc gtc ttg ggt aag tcc atc ttc tgt atg gac cca gtc       672
Gln Ser Ser Ala Val Leu Gly Lys Ser Ile Phe Cys Met Asp Pro Val
    210                 215                 220 atc gct ttg atg cac gag ttg acc cac tcc ctg cac cag ttg tac ggt       720
Ile Ala Leu Met His Glu Leu Thr His Ser Leu His Gln Leu Tyr Gly
225                 230                 235                 240 att aac atc cca tct gac aag aga atc aga cca cag gtc tct gag ggt       768
Ile Asn Ile Pro Ser Asp Lys Arg Ile Arg Pro Gln Val Ser Glu Gly
                245                 250                 255 ttc ttc tcc caa gac ggt cca aac gtt cag ttc gag gag ttg tac acc       816
Phe Phe Ser Gln Asp Gly Pro Asn Val Gln Phe Glu Glu Leu Tyr Thr
            260                 265                 270 ttc ggt ggt ttg gac gtc gag att atc caa att gag aga tcc caa ttg       864
Phe Gly Gly Leu Asp Val Glu Ile Ile Gln Ile Glu Arg Ser Gln Leu
        275                 280                 285 aga gag aag gct ttg ggt cac tac aag gac atc gcc aag aga ctg aac       912
Arg Glu Lys Ala Leu Gly His Tyr Lys Asp Ile Ala Lys Arg Leu Asn
    290                 295                 300 aac atc aac aag acc att cca tct tcc tgg atc tcc aac att gac aag       960
Asn Ile Asn Lys Thr Ile Pro Ser Ser Trp Ile Ser Asn Ile Asp Lys
305                 310                 315                 320 tac aag aag att ttc tcc gag aag tac aac ttc gac aag gac aac acc      1008
Tyr Lys Lys Ile Phe Ser Glu Lys Tyr Asn Phe Asp Lys Asp Asn Thr
                325                 330                 335 ggt aac ttc gtc gtt aac atc gac aag ttc aac tct ttg tac tcc gac      1056
Gly Asn Phe Val Val Asn Ile Asp Lys Phe Asn Ser Leu Tyr Ser Asp
            340                 345                 350 ttg acc aac gtt atg tct gag gtt gtc tac tcc tcc caa tac aac gtc      1104
Leu Thr Asn Val Met Ser Glu Val Val Tyr Ser Ser Gln Tyr Asn Val
        355                 360                 365 aag aac aga acc cac tac ttc tcc aga cac tac ttg cca gtt ttc gct      1152
Lys Asn Arg Thr His Tyr Phe Ser Arg His Tyr Leu Pro Val Phe Ala
    370                 375                 380 aac atc ttg gac gac aac att tac acc atc aga gac ggt ttc aac ttg      1200
Asn Ile Leu Asp Asp Asn Ile Tyr Thr Ile Arg Asp Gly Phe Asn Leu
385                 390                 395                 400 acc aac aag ggt ttc aac atc gag aac tcc ggt caa aac atc gag aga      1248
Thr Asn Lys Gly Phe Asn Ile Glu Asn Ser Gly Gln Asn Ile Glu Arg
                405                 410                 415 aac cca gcc ctg caa aag ctg tcc tcc gag tct gtc gtc gac ttg ttc      1296
Asn Pro Ala Leu Gln Lys Leu Ser Ser Glu Ser Val Val Asp Leu Phe
            420                 425                 430 acc aag gtc tgt ttg aga ttg acc aag aac tcc cgt gac gac tcc acc      1344
Thr Lys Val Cys Leu Arg Leu Thr Lys Asn Ser Arg Asp Asp Ser Thr
        435                 440                 445 tgc atc aag gtc aag aac aac aga ctg cca tac gtt gcc gac aag gac      1392
Cys Ile Lys Val Lys Asn Asn Arg Leu Pro Tyr Val Ala Asp Lys Asp
    450                 455                 460 tcc atc tcc cag gag atc ttc gag aac aag atc atc acc gac gag acc      1440
Ser Ile Ser Gln Glu Ile Phe Glu Asn Lys Ile Ile Thr Asp Glu Thr
465                 470                 475                 480 aac gtt caa aac tac tcc gac aag ttc tct ttg gac gag tcc atc ctg      1488
Asn Val Gln Asn Tyr Ser Asp Lys Phe Ser Leu Asp Glu Ser Ile Leu
                485                 490                 495 gac ggt cag gtc cca atc aac cca gag atc gtc gac cca ctg ttg cca      1536
Asp Gly Gln Val Pro Ile Asn Pro Glu Ile Val Asp Pro Leu Leu Pro
            500                 505                 510 aac gtc aac atg gag cca ttg aac ttg cca ggt gag gag atc gtc ttc      1584
Asn Val Asn Met Glu Pro Leu Asn Leu Pro Gly Glu Glu Ile Val Phe
```

-continued

```
                515                 520                 525
tac gac gac atc acc aag tac gtc gac tac ttg aac tcc tac tac tac    1632
Tyr Asp Asp Ile Thr Lys Tyr Val Asp Tyr Leu Asn Ser Tyr Tyr Tyr
530                 535                 540 ttg gag tct caa aag ttg tct aac aac gtc gag aac atc acc ttg acc    1680
Leu Glu Ser Gln Lys Leu Ser Asn Asn Val Glu Asn Ile Thr Leu Thr
545                 550                 555                 560 acc tcc gtc gag gag gcc ttg ggt tac tct aac aag atc tac acc ttc    1728
Thr Ser Val Glu Glu Ala Leu Gly Tyr Ser Asn Lys Ile Tyr Thr Phe
                        565                 570                 575 ctg cca tcc ttg gct gag aag gtt aac aag ggt gtt caa gct ggt ttg    1776
Leu Pro Ser Leu Ala Glu Lys Val Asn Lys Gly Val Gln Ala Gly Leu
            580                 585                 590 ttc ctg aac tgg gcc aac gag gtc gtc gag gac ttc acc acc aac atc    1824
Phe Leu Asn Trp Ala Asn Glu Val Val Glu Asp Phe Thr Thr Asn Ile
                595                 600                 605 atg aag aag gac acc ctg gac aag atc tcc gac gtc tcc gtc atc atc    1872
Met Lys Lys Asp Thr Leu Asp Lys Ile Ser Asp Val Ser Val Ile Ile
610                 615                 620 cca tac atc ggt cca gcc ttg aac atc ggt aac tcc gcc ctg aga ggt    1920
Pro Tyr Ile Gly Pro Ala Leu Asn Ile Gly Asn Ser Ala Leu Arg Gly
625                 630                 635                 640 aac ttc aac cag gcc ttc gcc acc gcc ggt gtc gcc ttc ctg ctg gag    1968
Asn Phe Asn Gln Ala Phe Ala Thr Ala Gly Val Ala Phe Leu Leu Glu
                        645                 650                 655 ggt ttc cca gag ttc acc atc cca gcc ctg ggt gtc ttc acc ttc tac    2016
Gly Phe Pro Glu Phe Thr Ile Pro Ala Leu Gly Val Phe Thr Phe Tyr
            660                 665                 670 tcc tcc atc cag gag aga gag aag atc atc aag acc atc gag aac tgc    2064
Ser Ser Ile Gln Glu Arg Glu Lys Ile Ile Lys Thr Ile Glu Asn Cys
                675                 680                 685 ttg gag cag aga gtc aag aga tgg aag gac tcc tac cag tgg atg gtt    2112
Leu Glu Gln Arg Val Lys Arg Trp Lys Asp Ser Tyr Gln Trp Met Val
690                 695                 700 tcc aac tgg ctg tcc aga atc acc acc caa ttc aac cac atc aac tac    2160
Ser Asn Trp Leu Ser Arg Ile Thr Thr Gln Phe Asn His Ile Asn Tyr
705                 710                 715                 720 cag atg tac gac tcc ctg tcc tac cag gcc gac gcc atc aag gcc aag    2208
Gln Met Tyr Asp Ser Leu Ser Tyr Gln Ala Asp Ala Ile Lys Ala Lys
                        725                 730                 735 atc gac ctg gag tac aag aag tac tcc ggt tcc gac aag gag aac atc    2256
Ile Asp Leu Glu Tyr Lys Lys Tyr Ser Gly Ser Asp Lys Glu Asn Ile
            740                 745                 750 aag tcc cag gtc gag aac ctg aag aac tcc ttg gac gtc aag atc tcc    2304
Lys Ser Gln Val Glu Asn Leu Lys Asn Ser Leu Asp Val Lys Ile Ser
                755                 760                 765 gag gcc atg aac aac atc aac aag ttc atc cgt gag tgt tcc gtc acc    2352
Glu Ala Met Asn Asn Ile Asn Lys Phe Ile Arg Glu Cys Ser Val Thr
770                 775                 780 tac ctg ttc aag aac atg ctg cca aag gtc atc gac gag ctg aac aag    2400
Tyr Leu Phe Lys Asn Met Leu Pro Lys Val Ile Asp Glu Leu Asn Lys
785                 790                 795                 800 ttc gac ctg aga acc aag acc gag ctg atc aac ctg atc gac tcc cac    2448
Phe Asp Leu Arg Thr Lys Thr Glu Leu Ile Asn Leu Ile Asp Ser His
                        805                 810                 815 aac atc atc ctg gtt ggt gag gtt gac                                2475
Asn Ile Ile Leu Val Gly Glu Val Asp
            820                 825

<210> SEQ ID NO 10
```

-continued

<211> LENGTH: 825
<212> TYPE: PRT
<213> ORGANISM: Clostridium botulinum

<400> SEQUENCE: 10

```
Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Thr Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

Phe Gly Gly Leu Asp Val Glu Ile Ile Gln Ile Glu Arg Ser Gln Leu
        275                 280                 285

Arg Glu Lys Ala Leu Gly His Tyr Lys Asp Ile Ala Lys Arg Leu Asn
    290                 295                 300

Asn Ile Asn Lys Thr Ile Pro Ser Ser Trp Ile Ser Asn Ile Asp Lys
305                 310                 315                 320

Tyr Lys Lys Ile Phe Ser Glu Lys Tyr Asn Phe Asp Lys Asp Asn Thr
                325                 330                 335

Gly Asn Phe Val Val Asn Ile Asp Lys Phe Asn Ser Leu Tyr Ser Asp
            340                 345                 350

Leu Thr Asn Val Met Ser Glu Val Val Tyr Ser Ser Gln Tyr Asn Val
        355                 360                 365

Lys Asn Arg Thr His Tyr Phe Ser Arg His Tyr Leu Pro Val Phe Ala
    370                 375                 380

Asn Ile Leu Asp Asp Asn Ile Tyr Thr Ile Arg Asp Gly Phe Asn Leu
385                 390                 395                 400
```

-continued

Thr Asn Lys Gly Phe Asn Ile Glu Asn Ser Gly Gln Asn Ile Glu Arg
        405                 410                 415
Asn Pro Ala Leu Gln Lys Leu Ser Ser Glu Ser Val Val Asp Leu Phe
        420                 425                 430
Thr Lys Val Cys Leu Arg Leu Thr Lys Asn Ser Arg Asp Asp Ser Thr
        435                 440                 445
Cys Ile Lys Val Lys Asn Asn Arg Leu Pro Tyr Val Ala Asp Lys Asp
        450                 455                 460
Ser Ile Ser Gln Glu Ile Phe Glu Asn Lys Ile Ile Thr Asp Glu Thr
465                 470                 475                 480
Asn Val Gln Asn Tyr Ser Asp Lys Phe Ser Leu Asp Glu Ser Ile Leu
        485                 490                 495
Asp Gly Gln Val Pro Ile Asn Pro Glu Ile Val Asp Pro Leu Leu Pro
        500                 505                 510
Asn Val Asn Met Glu Pro Leu Asn Leu Pro Gly Glu Glu Ile Val Phe
        515                 520                 525
Tyr Asp Asp Ile Thr Lys Tyr Val Asp Tyr Leu Asn Ser Tyr Tyr Tyr
        530                 535                 540
Leu Glu Ser Gln Lys Leu Ser Asn Asn Val Glu Asn Ile Thr Leu Thr
545                 550                 555                 560
Thr Ser Val Glu Glu Ala Leu Gly Tyr Ser Asn Lys Ile Tyr Thr Phe
        565                 570                 575
Leu Pro Ser Leu Ala Glu Lys Val Asn Lys Gly Val Gln Ala Gly Leu
        580                 585                 590
Phe Leu Asn Trp Ala Asn Glu Val Val Glu Asp Phe Thr Thr Asn Ile
        595                 600                 605
Met Lys Lys Asp Thr Leu Asp Lys Ile Ser Asp Val Ser Val Ile Ile
        610                 615                 620
Pro Tyr Ile Gly Pro Ala Leu Asn Ile Gly Asn Ser Ala Leu Arg Gly
625                 630                 635                 640
Asn Phe Asn Gln Ala Phe Ala Thr Ala Gly Val Ala Phe Leu Leu Glu
        645                 650                 655
Gly Phe Pro Glu Phe Thr Ile Pro Ala Leu Gly Val Phe Thr Phe Tyr
        660                 665                 670
Ser Ser Ile Gln Glu Arg Glu Lys Ile Ile Lys Thr Ile Glu Asn Cys
        675                 680                 685
Leu Glu Gln Arg Val Lys Arg Trp Lys Asp Ser Tyr Gln Trp Met Val
        690                 695                 700
Ser Asn Trp Leu Ser Arg Ile Thr Thr Gln Phe Asn His Ile Asn Tyr
705                 710                 715                 720
Gln Met Tyr Asp Ser Leu Ser Tyr Gln Ala Asp Ala Ile Lys Ala Lys
        725                 730                 735
Ile Asp Leu Glu Tyr Lys Lys Tyr Ser Gly Ser Asp Lys Glu Asn Ile
        740                 745                 750
Lys Ser Gln Val Glu Asn Leu Lys Asn Ser Leu Asp Val Lys Ile Ser
        755                 760                 765
Glu Ala Met Asn Asn Ile Asn Lys Phe Ile Arg Glu Cys Ser Val Thr
        770                 775                 780
Tyr Leu Phe Lys Asn Met Leu Pro Lys Val Ile Asp Glu Leu Asn Lys
785                 790                 795                 800
Phe Asp Leu Arg Thr Lys Thr Glu Leu Ile Asn Leu Ile Asp Ser His
        805                 810                 815
Asn Ile Ile Leu Val Gly Glu Val Asp

<210> SEQ ID NO 11
<211> LENGTH: 2577
<212> TYPE: DNA
<213> ORGANISM: Clostridium botulinum
<220> FEATURE:
<221> NAME/KEY: CDS
<222> LOCATION: (1)..(2577)

<400> SEQUENCE: 11

| | | | | | | | | | | | | | | | | |
|---|---|---|---|---|---|---|---|---|---|---|---|---|---|---|---|---|
| cat | atg | ccg | gtt | gtc | atc | aat | tct | ttt | aac | tac | aac | gac | ccg | gtg | aac | 48 |
| His | Met | Pro | Val | Val | Ile | Asn | Ser | Phe | Asn | Tyr | Asn | Asp | Pro | Val | Asn | |
| 1 | | | | 5 | | | | | 10 | | | | | 15 | | |
| gac | gac | acg | att | ctg | tac | atg | caa | atc | cct | tac | gag | gag | aag | tct | aaa | 96 |
| Asp | Asp | Thr | Ile | Leu | Tyr | Met | Gln | Ile | Pro | Tyr | Glu | Glu | Lys | Ser | Lys | |
| | | | 20 | | | | | 25 | | | | | 30 | | | |
| aag | tat | tat | aag | gcg | ttc | gag | atc | atg | cgc | aac | gtg | tgg | atc | atc | ccg | 144 |
| Lys | Tyr | Tyr | Lys | Ala | Phe | Glu | Ile | Met | Arg | Asn | Val | Trp | Ile | Ile | Pro | |
| | | 35 | | | | | 40 | | | | | 45 | | | | |
| gaa | cgc | aac | act | att | ggg | aca | gac | ccg | tcg | gac | ttc | gat | ccg | cct | gcg | 192 |
| Glu | Arg | Asn | Thr | Ile | Gly | Thr | Asp | Pro | Ser | Asp | Phe | Asp | Pro | Pro | Ala | |
| | 50 | | | | | 55 | | | | | 60 | | | | | |
| tcg | ctt | gaa | aac | ggc | tca | tca | gca | tac | tat | gac | cca | aat | tat | ttg | act | 240 |
| Ser | Leu | Glu | Asn | Gly | Ser | Ser | Ala | Tyr | Tyr | Asp | Pro | Asn | Tyr | Leu | Thr | |
| 65 | | | | | 70 | | | | | 75 | | | | | 80 | |
| acg | gac | gcg | gaa | aag | gac | cgt | tat | ctc | aag | acc | aca | atc | aag | ctc | ttc | 288 |
| Thr | Asp | Ala | Glu | Lys | Asp | Arg | Tyr | Leu | Lys | Thr | Thr | Ile | Lys | Leu | Phe | |
| | | | | 85 | | | | | 90 | | | | | 95 | | |
| aag | cgt | att | aac | tcc | aac | ccg | gcg | ggc | gag | gta | ttg | ctt | cag | gag | att | 336 |
| Lys | Arg | Ile | Asn | Ser | Asn | Pro | Ala | Gly | Glu | Val | Leu | Leu | Gln | Glu | Ile | |
| | | | 100 | | | | | 105 | | | | | 110 | | | |
| tcc | tac | gcc | aag | cct | tac | ctc | ggc | aat | gag | cat | act | cct | atc | aac | gag | 384 |
| Ser | Tyr | Ala | Lys | Pro | Tyr | Leu | Gly | Asn | Glu | His | Thr | Pro | Ile | Asn | Glu | |
| | | | 115 | | | | | 120 | | | | | 125 | | | |
| ttc | cac | cct | gtg | acc | cga | acc | acg | tct | gta | aac | att | aag | agt | tcg | acg | 432 |
| Phe | His | Pro | Val | Thr | Arg | Thr | Thr | Ser | Val | Asn | Ile | Lys | Ser | Ser | Thr | |
| | | 130 | | | | | 135 | | | | | 140 | | | | |
| aat | gta | aag | tcg | tca | att | att | ctc | aac | ctc | ttg | gtc | ctt | ggc | gcg | ggg | 480 |
| Asn | Val | Lys | Ser | Ser | Ile | Ile | Leu | Asn | Leu | Leu | Val | Leu | Gly | Ala | Gly | |
| 145 | | | | | 150 | | | | | 155 | | | | | 160 | |
| ccg | gac | atc | ttc | gag | aac | tct | tcc | tac | ccg | gtt | cgc | aag | ctc | atg | gac | 528 |
| Pro | Asp | Ile | Phe | Glu | Asn | Ser | Ser | Tyr | Pro | Val | Arg | Lys | Leu | Met | Asp | |
| | | | | 165 | | | | | 170 | | | | | 175 | | |
| agt | ggg | ggg | gtc | tat | gac | ccg | agc | aac | gac | ggg | ttc | ggt | tcc | atc | aat | 576 |
| Ser | Gly | Gly | Val | Tyr | Asp | Pro | Ser | Asn | Asp | Gly | Phe | Gly | Ser | Ile | Asn | |
| | | | 180 | | | | | 185 | | | | | 190 | | | |
| atc | gtg | acc | ttc | tca | cct | gag | tac | gag | tat | aca | ttt | aac | gac | atc | agc | 624 |
| Ile | Val | Thr | Phe | Ser | Pro | Glu | Tyr | Glu | Tyr | Thr | Phe | Asn | Asp | Ile | Ser | |
| | | | 195 | | | | | 200 | | | | | 205 | | | |
| ggc | ggc | tac | aac | agt | agc | acc | gag | tcc | ttt | atc | gcc | gac | ccg | gcc | atc | 672 |
| Gly | Gly | Tyr | Asn | Ser | Ser | Thr | Glu | Ser | Phe | Ile | Ala | Asp | Pro | Ala | Ile | |
| | | 210 | | | | | 215 | | | | | 220 | | | | |
| agc | ctc | gct | cac | gag | ctc | atc | cac | gcc | ctg | cac | ggg | ctg | tac | ggg | gcc | 720 |
| Ser | Leu | Ala | His | Glu | Leu | Ile | His | Ala | Leu | His | Gly | Leu | Tyr | Gly | Ala | |
| 225 | | | | | 230 | | | | | 235 | | | | | 240 | |
| cgg | ggc | gtt | aca | tat | aag | gag | acc | atc | aaa | gtg | aag | cag | gcg | cca | ctc | 768 |
| Arg | Gly | Val | Thr | Tyr | Lys | Glu | Thr | Ile | Lys | Val | Lys | Gln | Ala | Pro | Leu | |
| | | | | 245 | | | | | 250 | | | | | 255 | | |
| atg | att | gcc | gaa | aag | cca | atc | cga | ttg | gag | gag | ttc | ctg | aca | ttc | ggg | 816 |
| Met | Ile | Ala | Glu | Lys | Pro | Ile | Arg | Leu | Glu | Glu | Phe | Leu | Thr | Phe | Gly | |
| | | | 260 | | | | | 265 | | | | | 270 | | | |

| | | | | | | | | | | | | | | | |
|---|---|---|---|---|---|---|---|---|---|---|---|---|---|---|---|
| ggc | cag | gac | ctg | aat | att | atc | act | agt | gca | atg | aag | gag | aag | att | tat | 864 |
| Gly | Gln | Asp | Leu | Asn | Ile | Ile | Thr | Ser | Ala | Met | Lys | Glu | Lys | Ile | Tyr |
| | | | 275 | | | | 280 | | | | | 285 | | | | aac aac ctg ctc gcg aac tat gag aag atc gcc act cgc tta tcc cgg 912
Asn Asn Leu Leu Ala Asn Tyr Glu Lys Ile Ala Thr Arg Leu Ser Arg
        290                 295                 300 gtg aac tcc gcc cca ccg gag tat gac att aac gag tat aaa gac tac 960
Val Asn Ser Ala Pro Pro Glu Tyr Asp Ile Asn Glu Tyr Lys Asp Tyr
305                 310                 315                 320 ttc cag tgg aag tat gga ctg gat aaa aac gcg gac ggg tct tac acc 1008
Phe Gln Trp Lys Tyr Gly Leu Asp Lys Asn Ala Asp Gly Ser Tyr Thr
            325                 330                 335 gtg aac gag aac aaa ttc aac gag atc tac aag aag ctc tac agc ttc 1056
Val Asn Glu Asn Lys Phe Asn Glu Ile Tyr Lys Lys Leu Tyr Ser Phe
        340                 345                 350 acg gag atc gac ctc gcg aac aag ttc aag gtg aag tgc cgg aac acg 1104
Thr Glu Ile Asp Leu Ala Asn Lys Phe Lys Val Lys Cys Arg Asn Thr
            355                 360                 365 tat ttc atc aag tac ggc ttc tta aag gtg cca aac ctg tta gac gac 1152
Tyr Phe Ile Lys Tyr Gly Phe Leu Lys Val Pro Asn Leu Leu Asp Asp
370                 375                 380 gac att tat acc gta tcg gag ggc ttc aat att ggt aat ctg gcc gtg 1200
Asp Ile Tyr Thr Val Ser Glu Gly Phe Asn Ile Gly Asn Leu Ala Val
385                 390                 395                 400 aac aat cgc ggc cag aat att aaa ctt aac ccg aaa att atc gac tcg 1248
Asn Asn Arg Gly Gln Asn Ile Lys Leu Asn Pro Lys Ile Ile Asp Ser
            405                 410                 415 atc cca gac aag ggg tta gtt gag aag atc gtc aag ttc tgc aag tcg 1296
Ile Pro Asp Lys Gly Leu Val Glu Lys Ile Val Lys Phe Cys Lys Ser
        420                 425                 430 gtc atc cct cgc aag ggg acg aag aat tgc aag tcc gtc atc cca cgt 1344
Val Ile Pro Arg Lys Gly Thr Lys Asn Cys Lys Ser Val Ile Pro Arg
            435                 440                 445 aag ggt acc aag gcc cca cca cgt ctg tgt att aga gtc aac aac tca 1392
Lys Gly Thr Lys Ala Pro Pro Arg Leu Cys Ile Arg Val Asn Asn Ser
450                 455                 460 gaa tta ttc ttt gtc gct tcc gag tca agc tac aac gag aac gat att 1440
Glu Leu Phe Phe Val Ala Ser Glu Ser Ser Tyr Asn Glu Asn Asp Ile
465                 470                 475                 480 aac aca cct aaa gag att gac gat act acc aac cta aac aac aac tac 1488
Asn Thr Pro Lys Glu Ile Asp Asp Thr Thr Asn Leu Asn Asn Asn Tyr
            485                 490                 495 cgg aac aac ttg gat gag gtt att ttg gat tac aac tca cag acc atc 1536
Arg Asn Asn Leu Asp Glu Val Ile Leu Asp Tyr Asn Ser Gln Thr Ile
        500                 505                 510 cct caa att tcc aac cgt acc tta aac act ctt gtc caa gac aac tcc 1584
Pro Gln Ile Ser Asn Arg Thr Leu Asn Thr Leu Val Gln Asp Asn Ser
            515                 520                 525 tac gtt cca aga tac gat tct aac ggt acc tca gag atc gag gag tat 1632
Tyr Val Pro Arg Tyr Asp Ser Asn Gly Thr Ser Glu Ile Glu Glu Tyr
530                 535                 540 gat gtt gtt gac ttt aac gtc ttc ttc tat ttg cat gcc cag aag gtg 1680
Asp Val Val Asp Phe Asn Val Phe Phe Tyr Leu His Ala Gln Lys Val
545                 550                 555                 560 cca gaa ggt gaa acc aac atc tca ttg act tct tcc att gat acc gcc 1728
Pro Glu Gly Glu Thr Asn Ile Ser Leu Thr Ser Ser Ile Asp Thr Ala
            565                 570                 575 ttg ttg gaa gag tcc aag gat atc ttc ttt tct tcg gag ttt atc gat 1776
Leu Leu Glu Glu Ser Lys Asp Ile Phe Phe Ser Ser Glu Phe Ile Asp
        580                 585                 590

| | | | | | | | | | | | | | | | | |
|---|---|---|---|---|---|---|---|---|---|---|---|---|---|---|---|---|
| act | atc | aac | aag | cct | gtc | aac | gcc | gct | ctg | ttc | att | gat | tgg | att | agc | 1824 |
| Thr | Ile | Asn | Lys | Pro | Val | Asn | Ala | Ala | Leu | Phe | Ile | Asp | Trp | Ile | Ser | |
| | | | | 595 | | | | 600 | | | | 605 | | | | |
| aag | gtc | atc | aga | gat | ttt | acc | act | gaa | gct | act | caa | aag | tcc | act | gtt | 1872 |
| Lys | Val | Ile | Arg | Asp | Phe | Thr | Thr | Glu | Ala | Thr | Gln | Lys | Ser | Thr | Val | |
| 610 | | | | | 615 | | | | | 620 | | | | | | |
| gat | aag | att | gct | gac | atc | tct | ttg | att | gtc | ccc | tat | gtc | ggt | ctt | gct | 1920 |
| Asp | Lys | Ile | Ala | Asp | Ile | Ser | Leu | Ile | Val | Pro | Tyr | Val | Gly | Leu | Ala | |
| 625 | | | | | 630 | | | | | 635 | | | | | 640 | |
| ttg | aac | atc | att | att | gag | gca | gaa | aag | ggt | aac | ttt | gag | gag | gct | ttt | 1968 |
| Leu | Asn | Ile | Ile | Ile | Glu | Ala | Glu | Lys | Gly | Asn | Phe | Glu | Glu | Ala | Phe | |
| | | | | 645 | | | | 650 | | | | 655 | | | | |
| gaa | ttg | ttg | gga | gtt | ggt | att | ttg | ttg | gag | ttt | gtt | cca | gaa | ctt | acc | 2016 |
| Glu | Leu | Leu | Gly | Val | Gly | Ile | Leu | Leu | Glu | Phe | Val | Pro | Glu | Leu | Thr | |
| | | 660 | | | | | 665 | | | | | 670 | | | | |
| att | cct | gtc | att | tta | gtt | ttt | acg | atc | aag | tcc | tac | atc | gat | tca | tac | 2064 |
| Ile | Pro | Val | Ile | Leu | Val | Phe | Thr | Ile | Lys | Ser | Tyr | Ile | Asp | Ser | Tyr | |
| | 675 | | | | | 680 | | | | | 685 | | | | | |
| gag | aac | aag | aat | aaa | gca | att | aaa | gct | att | aac | aac | tcc | ttg | atc | gaa | 2112 |
| Glu | Asn | Lys | Asn | Lys | Ala | Ile | Lys | Ala | Ile | Asn | Asn | Ser | Leu | Ile | Glu | |
| 690 | | | | | 695 | | | | | 700 | | | | | | |
| aga | gag | gct | aag | tgg | aag | gaa | atc | tac | tca | tgg | att | gta | tca | aac | tgg | 2160 |
| Arg | Glu | Ala | Lys | Trp | Lys | Glu | Ile | Tyr | Ser | Trp | Ile | Val | Ser | Asn | Trp | |
| 705 | | | | | 710 | | | | | 715 | | | | | 720 | |
| ctt | act | aga | att | aac | act | caa | ttt | aac | aag | aga | aag | gag | caa | atg | tac | 2208 |
| Leu | Thr | Arg | Ile | Asn | Thr | Gln | Phe | Asn | Lys | Arg | Lys | Glu | Gln | Met | Tyr | |
| | | | | 725 | | | | 730 | | | | 735 | | | | |
| cag | gct | ctg | caa | aac | caa | gtc | gat | gct | atc | aag | act | gca | att | gaa | tac | 2256 |
| Gln | Ala | Leu | Gln | Asn | Gln | Val | Asp | Ala | Ile | Lys | Thr | Ala | Ile | Glu | Tyr | |
| | | 740 | | | | | 745 | | | | | 750 | | | | |
| aag | tac | aac | aac | tat | act | tcc | gat | gag | aag | aac | aga | ctt | gaa | tct | gaa | 2304 |
| Lys | Tyr | Asn | Asn | Tyr | Thr | Ser | Asp | Glu | Lys | Asn | Arg | Leu | Glu | Ser | Glu | |
| | 755 | | | | | 760 | | | | | 765 | | | | | |
| tac | aat | atc | aac | aac | att | gaa | gaa | gag | ttg | aac | aag | aaa | gtt | tct | ttg | 2352 |
| Tyr | Asn | Ile | Asn | Asn | Ile | Glu | Glu | Glu | Leu | Asn | Lys | Lys | Val | Ser | Leu | |
| 770 | | | | | 775 | | | | | 780 | | | | | | |
| gct | atg | aag | aat | atc | gaa | aga | ttt | atg | acc | gaa | tcc | tct | atc | tct | tac | 2400 |
| Ala | Met | Lys | Asn | Ile | Glu | Arg | Phe | Met | Thr | Glu | Ser | Ser | Ile | Ser | Tyr | |
| 785 | | | | | 790 | | | | | 795 | | | | | 800 | |
| ttg | atg | aag | ttg | atc | aat | gag | gcc | aag | gtt | ggt | aag | ttg | aag | aag | tac | 2448 |
| Leu | Met | Lys | Leu | Ile | Asn | Glu | Ala | Lys | Val | Gly | Lys | Leu | Lys | Lys | Tyr | |
| | | | 805 | | | | | 810 | | | | | 815 | | | |
| gat | aac | cac | gtt | aag | agc | gat | ctg | ctg | aac | tac | att | ctc | gac | cac | aga | 2496 |
| Asp | Asn | His | Val | Lys | Ser | Asp | Leu | Leu | Asn | Tyr | Ile | Leu | Asp | His | Arg | |
| | | | 820 | | | | | 825 | | | | | 830 | | | |
| tca | atc | ctg | gga | gag | cag | aca | aac | gag | ctg | agt | gat | ttg | gtt | act | tcc | 2544 |
| Ser | Ile | Leu | Gly | Glu | Gln | Thr | Asn | Glu | Leu | Ser | Asp | Leu | Val | Thr | Ser | |
| | | 835 | | | | | 840 | | | | | 845 | | | | |
| act | ttg | aac | tcc | tcc | att | cca | ttt | gag | ctt | tct | | | | | | 2577 |
| Thr | Leu | Asn | Ser | Ser | Ile | Pro | Phe | Glu | Leu | Ser | | | | | | |
| | 850 | | | | | 855 | | | | | | | | | | |

<210> SEQ ID NO 12
<211> LENGTH: 859
<212> TYPE: PRT
<213> ORGANISM: Clostridium botulinum

<400> SEQUENCE: 12

His Met Pro Val Val Ile Asn Ser Phe Asn Tyr Asn Asp Pro Val Asn
1               5                   10                  15

-continued

Asp Asp Thr Ile Leu Tyr Met Gln Ile Pro Tyr Glu Glu Lys Ser Lys
            20                  25                  30

Lys Tyr Tyr Lys Ala Phe Glu Ile Met Arg Asn Val Trp Ile Ile Pro
        35                  40                  45

Glu Arg Asn Thr Ile Gly Thr Asp Pro Ser Asp Phe Asp Pro Pro Ala
50                  55                  60

Ser Leu Glu Asn Gly Ser Ser Ala Tyr Tyr Asp Pro Asn Tyr Leu Thr
65                  70                  75                  80

Thr Asp Ala Glu Lys Asp Arg Tyr Leu Lys Thr Thr Ile Lys Leu Phe
                85                  90                  95

Lys Arg Ile Asn Ser Asn Pro Ala Gly Glu Val Leu Leu Gln Glu Ile
                100                 105                 110

Ser Tyr Ala Lys Pro Tyr Leu Gly Asn Glu His Thr Pro Ile Asn Glu
            115                 120                 125

Phe His Pro Val Thr Arg Thr Thr Ser Val Asn Ile Lys Ser Ser Thr
            130                 135                 140

Asn Val Lys Ser Ser Ile Ile Leu Asn Leu Leu Val Leu Gly Ala Gly
145                 150                 155                 160

Pro Asp Ile Phe Glu Asn Ser Ser Tyr Pro Val Arg Lys Leu Met Asp
                165                 170                 175

Ser Gly Gly Val Tyr Asp Pro Ser Asn Asp Gly Phe Gly Ser Ile Asn
            180                 185                 190

Ile Val Thr Phe Ser Pro Glu Tyr Glu Tyr Thr Phe Asn Asp Ile Ser
            195                 200                 205

Gly Gly Tyr Asn Ser Ser Thr Glu Ser Phe Ile Ala Asp Pro Ala Ile
            210                 215                 220

Ser Leu Ala His Glu Leu Ile His Ala Leu His Gly Leu Tyr Gly Ala
225                 230                 235                 240

Arg Gly Val Thr Tyr Lys Glu Thr Ile Lys Val Lys Gln Ala Pro Leu
                245                 250                 255

Met Ile Ala Glu Lys Pro Ile Arg Leu Glu Glu Phe Leu Thr Phe Gly
                260                 265                 270

Gly Gln Asp Leu Asn Ile Ile Thr Ser Ala Met Lys Glu Lys Ile Tyr
            275                 280                 285

Asn Asn Leu Leu Ala Asn Tyr Glu Lys Ile Ala Thr Arg Leu Ser Arg
            290                 295                 300

Val Asn Ser Ala Pro Pro Glu Tyr Asp Ile Asn Glu Tyr Lys Asp Tyr
305                 310                 315                 320

Phe Gln Trp Lys Tyr Gly Leu Asp Lys Asn Ala Asp Gly Ser Tyr Thr
                325                 330                 335

Val Asn Glu Asn Lys Phe Asn Glu Ile Tyr Lys Lys Leu Tyr Ser Phe
            340                 345                 350

Thr Glu Ile Asp Leu Ala Asn Lys Phe Lys Val Lys Cys Arg Asn Thr
            355                 360                 365

Tyr Phe Ile Lys Tyr Gly Phe Leu Lys Val Pro Asn Leu Leu Asp Asp
            370                 375                 380

Asp Ile Tyr Thr Val Ser Glu Gly Phe Asn Ile Gly Asn Leu Ala Val
385                 390                 395                 400

Asn Asn Arg Gly Gln Asn Ile Lys Leu Asn Pro Lys Ile Ile Asp Ser
                405                 410                 415

Ile Pro Asp Lys Gly Leu Val Glu Lys Ile Val Lys Phe Cys Lys Ser
                420                 425                 430

Val Ile Pro Arg Lys Gly Thr Lys Asn Cys Lys Ser Val Ile Pro Arg
                435                 440                 445

```
Lys Gly Thr Lys Ala Pro Pro Arg Leu Cys Ile Arg Val Asn Asn Ser
    450                 455                 460

Glu Leu Phe Phe Val Ala Ser Glu Ser Ser Tyr Asn Glu Asn Asp Ile
465             470                 475                 480

Asn Thr Pro Lys Glu Ile Asp Asp Thr Thr Asn Leu Asn Asn Asn Tyr
                485                 490                 495

Arg Asn Asn Leu Asp Glu Val Ile Leu Asp Tyr Asn Ser Gln Thr Ile
            500                 505                 510

Pro Gln Ile Ser Asn Arg Thr Leu Asn Thr Leu Val Gln Asp Asn Ser
        515                 520                 525

Tyr Val Pro Arg Tyr Asp Ser Asn Gly Thr Ser Glu Ile Glu Glu Tyr
    530                 535                 540

Asp Val Val Asp Phe Asn Val Phe Phe Tyr Leu His Ala Gln Lys Val
545             550                 555                 560

Pro Glu Gly Glu Thr Asn Ile Ser Leu Thr Ser Ser Ile Asp Thr Ala
                565                 570                 575

Leu Leu Glu Glu Ser Lys Asp Ile Phe Phe Ser Ser Glu Phe Ile Asp
            580                 585                 590

Thr Ile Asn Lys Pro Val Asn Ala Ala Leu Phe Ile Asp Trp Ile Ser
        595                 600                 605

Lys Val Ile Arg Asp Phe Thr Thr Glu Ala Thr Gln Lys Ser Thr Val
    610                 615                 620

Asp Lys Ile Ala Asp Ile Ser Leu Ile Val Pro Tyr Val Gly Leu Ala
625             630                 635                 640

Leu Asn Ile Ile Ile Glu Ala Glu Lys Gly Asn Phe Glu Glu Ala Phe
                645                 650                 655

Glu Leu Leu Gly Val Gly Ile Leu Leu Glu Phe Val Pro Glu Leu Thr
            660                 665                 670

Ile Pro Val Ile Leu Val Phe Thr Ile Lys Ser Tyr Ile Asp Ser Tyr
        675                 680                 685

Glu Asn Lys Asn Lys Ala Ile Lys Ala Ile Asn Asn Ser Leu Ile Glu
    690                 695                 700

Arg Glu Ala Lys Trp Lys Glu Ile Tyr Ser Trp Ile Val Ser Asn Trp
705             710                 715                 720

Leu Thr Arg Ile Asn Thr Gln Phe Asn Lys Arg Lys Glu Gln Met Tyr
                725                 730                 735

Gln Ala Leu Gln Asn Gln Val Asp Ala Ile Lys Thr Ala Ile Glu Tyr
            740                 745                 750

Lys Tyr Asn Asn Tyr Thr Ser Asp Glu Lys Asn Arg Leu Glu Ser Glu
        755                 760                 765

Tyr Asn Ile Asn Asn Ile Glu Glu Glu Leu Asn Lys Lys Val Ser Leu
    770                 775                 780

Ala Met Lys Asn Ile Glu Arg Phe Met Thr Glu Ser Ser Ile Ser Tyr
785             790                 795                 800

Leu Met Lys Leu Ile Asn Glu Ala Lys Val Gly Lys Leu Lys Lys Tyr
                805                 810                 815

Asp Asn His Val Lys Ser Asp Leu Leu Asn Tyr Ile Leu Asp His Arg
            820                 825                 830

Ser Ile Leu Gly Glu Gln Thr Asn Glu Leu Ser Asp Leu Val Thr Ser
        835                 840                 845

Thr Leu Asn Ser Ser Ile Pro Phe Glu Leu Ser
850                 855
```

```
<210> SEQ ID NO 13
<211> LENGTH: 2547
<212> TYPE: DNA
<213> ORGANISM: Clostridium botulinum
<220> FEATURE:
<221> NAME/KEY: CDS
<222> LOCATION: (1)..(2547)

<400> SEQUENCE: 13 cat atg ccg gtc aat att aag aac ttc aat tac aac gac ccg atc aat      48
His Met Pro Val Asn Ile Lys Asn Phe Asn Tyr Asn Asp Pro Ile Asn
1               5                   10                  15 aat gac gat atc att atg atg gag cct ttc aac gac cca ggt cca ggc      96
Asn Asp Asp Ile Ile Met Met Glu Pro Phe Asn Asp Pro Gly Pro Gly
            20                  25                  30 acg tat tac aag gct ttt cgg atc atc gac cgc att tgg atc gtc ccg     144
Thr Tyr Tyr Lys Ala Phe Arg Ile Ile Asp Arg Ile Trp Ile Val Pro
        35                  40                  45 gag cgc ttc acg tac ggc ttc caa cct gac cag ttc aat gca agc aca     192
Glu Arg Phe Thr Tyr Gly Phe Gln Pro Asp Gln Phe Asn Ala Ser Thr
    50                  55                  60 ggg gtt ttc agc aag gac gtc tac gag tac tat gac cca act tac ctg     240
Gly Val Phe Ser Lys Asp Val Tyr Glu Tyr Tyr Asp Pro Thr Tyr Leu
65                  70                  75                  80 aag act gac gcg gag aag gac aaa ttc ctg aag acg atg atc aag ttg     288
Lys Thr Asp Ala Glu Lys Asp Lys Phe Leu Lys Thr Met Ile Lys Leu
                85                  90                  95 ttc aac cgc att aac tcc aag ccg tcc ggc cag cga ctg ctt gat atg     336
Phe Asn Arg Ile Asn Ser Lys Pro Ser Gly Gln Arg Leu Leu Asp Met
            100                 105                 110 att gtg gac gcc atc cct tac ctc gga aac gcc tct acg cca ccg gac     384
Ile Val Asp Ala Ile Pro Tyr Leu Gly Asn Ala Ser Thr Pro Pro Asp
        115                 120                 125 aag ttc gcg gca aac gtt gca aac gtg tcc atc aac aag aaa att att     432
Lys Phe Ala Ala Asn Val Ala Asn Val Ser Ile Asn Lys Lys Ile Ile
    130                 135                 140 cag ccg ggg gcc gag gac cag att aag gga ctt atg act aat ctg atc     480
Gln Pro Gly Ala Glu Asp Gln Ile Lys Gly Leu Met Thr Asn Leu Ile
145                 150                 155                 160 atc ttc ggg ccg ggg cct gta ctc tcg gac aac ttc acg gac agc atg     528
Ile Phe Gly Pro Gly Pro Val Leu Ser Asp Asn Phe Thr Asp Ser Met
                165                 170                 175 att atg aac ggc cat tca ccg atc tca gaa gga ttc ggg gca cgt atg     576
Ile Met Asn Gly His Ser Pro Ile Ser Glu Gly Phe Gly Ala Arg Met
            180                 185                 190 atg atc cgg ttc tgc ccg agt tgc ctc aac gtc ttc aac aac gtc cag     624
Met Ile Arg Phe Cys Pro Ser Cys Leu Asn Val Phe Asn Asn Val Gln
        195                 200                 205 gaa aat aag gat aca tcg atc ttc tcc cgc cgt gcc tac ttc gcg gac     672
Glu Asn Lys Asp Thr Ser Ile Phe Ser Arg Arg Ala Tyr Phe Ala Asp
    210                 215                 220 cca gcg tta acc ctt atg cac gag tta atc cac gta ttg cac ggc ctc     720
Pro Ala Leu Thr Leu Met His Glu Leu Ile His Val Leu His Gly Leu
225                 230                 235                 240 tac ggc att aag atc tcg aac tta cct att acc cca aac acg aaa gag     768
Tyr Gly Ile Lys Ile Ser Asn Leu Pro Ile Thr Pro Asn Thr Lys Glu
                245                 250                 255 ttc ttc atg caa cac agc gac ccg gtt cag gcc gag gaa tta tac acc     816
Phe Phe Met Gln His Ser Asp Pro Val Gln Ala Glu Glu Leu Tyr Thr
            260                 265                 270 ttc ggc ggg cac gac cca agt gtt atc tca ccg tct acc gat atg aat     864
Phe Gly Gly His Asp Pro Ser Val Ile Ser Pro Ser Thr Asp Met Asn
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 275 |     |     |     | 280 |     |     |     | 285 |     |     |     |     |     |      |
| atc | tac | aac | aag | gcc | ctg | caa | aac | ttc | cag | gac | atc | gca | aac | cgg | ctt | 912  |
| Ile | Tyr | Asn | Lys | Ala | Leu | Gln | Asn | Phe | Gln | Asp | Ile | Ala | Asn | Arg | Leu |      |
|     |     | 290 |     |     |     | 295 |     |     |     | 300 |     |     |     |     |     |      |
| aac | att | gtc | tca | tcg | gca | cag | ggg | tct | ggt | atc | gac | atc | tcc | ctg | tat | 960  |
| Asn | Ile | Val | Ser | Ser | Ala | Gln | Gly | Ser | Gly | Ile | Asp | Ile | Ser | Leu | Tyr |      |
| 305 |     |     |     |     | 310 |     |     |     |     | 315 |     |     |     |     | 320 |      |
| aag | cag | atc | tac | aag | aat | aag | tac | gac | ttc | gta | gaa | gac | ccg | aac | ggc | 1008 |
| Lys | Gln | Ile | Tyr | Lys | Asn | Lys | Tyr | Asp | Phe | Val | Glu | Asp | Pro | Asn | Gly |      |
|     |     |     |     | 325 |     |     |     |     | 330 |     |     |     |     | 335 |     |      |
| aag | tac | tcg | gtg | gac | aag | gac | aag | ttt | gac | aaa | ctc | tac | aaa | gct | ctc | 1056 |
| Lys | Tyr | Ser | Val | Asp | Lys | Asp | Lys | Phe | Asp | Lys | Leu | Tyr | Lys | Ala | Leu |      |
|     |     |     | 340 |     |     |     |     | 345 |     |     |     |     | 350 |     |     |      |
| atg | ttc | ggt | ttc | aca | gag | aca | aat | ctt | gcc | gga | gag | tac | ggg | atc | aag | 1104 |
| Met | Phe | Gly | Phe | Thr | Glu | Thr | Asn | Leu | Ala | Gly | Glu | Tyr | Gly | Ile | Lys |      |
|     |     | 355 |     |     |     |     | 360 |     |     |     |     | 365 |     |     |     |      |
| acg | cgg | tac | tcg | tat | ttt | tcc | gag | tac | ctg | ccg | cct | att | aag | acg | gag | 1152 |
| Thr | Arg | Tyr | Ser | Tyr | Phe | Ser | Glu | Tyr | Leu | Pro | Pro | Ile | Lys | Thr | Glu |      |
|     | 370 |     |     |     |     | 375 |     |     |     |     | 380 |     |     |     |     |      |
| aag | ttg | ctc | gat | aac | acc | att | tac | act | cag | aat | gag | ggg | ttc | aac | atc | 1200 |
| Lys | Leu | Leu | Asp | Asn | Thr | Ile | Tyr | Thr | Gln | Asn | Glu | Gly | Phe | Asn | Ile |      |
| 385 |     |     |     |     | 390 |     |     |     |     | 395 |     |     |     |     | 400 |      |
| gcc | tct | aag | aat | ctc | aag | acc | gag | ttc | aat | ggt | cag | aac | aag | gcg | gtg | 1248 |
| Ala | Ser | Lys | Asn | Leu | Lys | Thr | Glu | Phe | Asn | Gly | Gln | Asn | Lys | Ala | Val |      |
|     |     |     |     | 405 |     |     |     |     | 410 |     |     |     |     | 415 |     |      |
| aac | aaa | gag | gcg | tat | gag | gag | att | agt | ctg | gaa | cac | ttg | gtg | atc | tac | 1296 |
| Asn | Lys | Glu | Ala | Tyr | Glu | Glu | Ile | Ser | Leu | Glu | His | Leu | Val | Ile | Tyr |      |
|     |     |     | 420 |     |     |     |     | 425 |     |     |     |     | 430 |     |     |      |
| cga | att | gcg | atg | tgt | aag | cct | gtg | atg | tac | aag | aac | acc | ggt | aag | tcc | 1344 |
| Arg | Ile | Ala | Met | Cys | Lys | Pro | Val | Met | Tyr | Lys | Asn | Thr | Gly | Lys | Ser |      |
|     |     | 435 |     |     |     |     | 440 |     |     |     |     | 445 |     |     |     |      |
| gag | cag | tgt | atc | atc | gtc | aac | aac | gag | gac | ttg | ttc | ttc | atc | gcc | aac | 1392 |
| Glu | Gln | Cys | Ile | Ile | Val | Asn | Asn | Glu | Asp | Leu | Phe | Phe | Ile | Ala | Asn |      |
|     | 450 |     |     |     |     | 455 |     |     |     |     | 460 |     |     |     |     |      |
| aag | gac | tcc | ttc | tcc | aag | gac | ttg | gcc | aag | gct | gag | acc | atc | gcc | tac | 1440 |
| Lys | Asp | Ser | Phe | Ser | Lys | Asp | Leu | Ala | Lys | Ala | Glu | Thr | Ile | Ala | Tyr |      |
| 465 |     |     |     |     | 470 |     |     |     |     | 475 |     |     |     |     | 480 |      |
| aac | acc | cag | aac | aac | acc | atc | gag | aac | aac | ttc | tcc | atc | gac | cag | ctg | 1488 |
| Asn | Thr | Gln | Asn | Asn | Thr | Ile | Glu | Asn | Asn | Phe | Ser | Ile | Asp | Gln | Leu |      |
|     |     |     |     | 485 |     |     |     |     | 490 |     |     |     |     | 495 |     |      |
| atc | ttg | gac | aac | gac | ctg | tcc | tcc | ggt | atc | gac | ctg | cca | aac | gag | aac | 1536 |
| Ile | Leu | Asp | Asn | Asp | Leu | Ser | Ser | Gly | Ile | Asp | Leu | Pro | Asn | Glu | Asn |      |
|     |     |     | 500 |     |     |     |     | 505 |     |     |     |     | 510 |     |     |      |
| acc | gag | cca | ttc | acc | aac | ttc | gac | gac | atc | gac | atc | cca | gtc | tac | atc | 1584 |
| Thr | Glu | Pro | Phe | Thr | Asn | Phe | Asp | Asp | Ile | Asp | Ile | Pro | Val | Tyr | Ile |      |
|     |     | 515 |     |     |     |     | 520 |     |     |     |     | 525 |     |     |     |      |
| aag | cag | tcc | gcc | ctg | aag | aag | atc | ttc | gtc | gac | ggt | gac | tcc | ttg | ttc | 1632 |
| Lys | Gln | Ser | Ala | Leu | Lys | Lys | Ile | Phe | Val | Asp | Gly | Asp | Ser | Leu | Phe |      |
|     | 530 |     |     |     |     | 535 |     |     |     |     | 540 |     |     |     |     |      |
| gag | tac | ctg | cac | gcc | cag | acc | ttc | cca | tcc | aac | atc | gag | aac | cag | ttg | 1680 |
| Glu | Tyr | Leu | His | Ala | Gln | Thr | Phe | Pro | Ser | Asn | Ile | Glu | Asn | Gln | Leu |      |
| 545 |     |     |     |     | 550 |     |     |     |     | 555 |     |     |     |     | 560 |      |
| acc | aac | tcc | ctg | aac | gac | gct | ttg | aga | aac | aac | aac | aag | gtc | tac | acc | 1728 |
| Thr | Asn | Ser | Leu | Asn | Asp | Ala | Leu | Arg | Asn | Asn | Asn | Lys | Val | Tyr | Thr |      |
|     |     |     |     | 565 |     |     |     |     | 570 |     |     |     |     | 575 |     |      |
| ttc | ttc | tcc | act | aac | ttg | gtc | gag | aag | gcc | aac | act | gtc | gtc | ggt | gcc | 1776 |
| Phe | Phe | Ser | Thr | Asn | Leu | Val | Glu | Lys | Ala | Asn | Thr | Val | Val | Gly | Ala |      |
|     |     |     | 580 |     |     |     |     | 585 |     |     |     |     | 590 |     |     |      |
| tcc | ttg | ttc | gtc | aac | tgg | gtc | aag | ggt | gtc | atc | gac | gac | ttc | acc | tcc | 1824 |
| Ser | Leu | Phe | Val | Asn | Trp | Val | Lys | Gly | Val | Ile | Asp | Asp | Phe | Thr | Ser |      |

-continued

| | | |
|---|---|---|
| gag tcc acc caa aag tcc acc atc gac aag gtc tcc gac gtc tcc atc<br>Glu Ser Thr Gln Lys Ser Thr Ile Asp Lys Val Ser Asp Val Ser Ile<br>610                                615                              620 | 1872 |
| atc atc cca tac atc ggt cca gcc ctg aac gtc ggt aac gag acc gct<br>Ile Ile Pro Tyr Ile Gly Pro Ala Leu Asn Val Gly Asn Glu Thr Ala<br>625                                630                              635                            640 | 1920 |
| aag gag aac ttc aag aac gcc ttc gag atc ggt ggt gcc gcc atc ctg<br>Lys Glu Asn Phe Lys Asn Ala Phe Glu Ile Gly Gly Ala Ala Ile Leu<br>                            645                              650                              655 | 1968 |
| atg gag ttc atc cca gag ttg atc gtc cca atc gtc ggt ttc ttc acc<br>Met Glu Phe Ile Pro Glu Leu Ile Val Pro Ile Val Gly Phe Phe Thr<br>660                                665                              670 | 2016 |
| ttg gag tcc tac gtc ggt aac aag ggt cac atc atc atg acc atc tcc<br>Leu Glu Ser Tyr Val Gly Asn Lys Gly His Ile Ile Met Thr Ile Ser<br>                          675                              680                              685 | 2064 |
| aac gcc ctg aag aag aga gac cag aag tgg acc gac atg tac ggt ttg<br>Asn Ala Leu Lys Lys Arg Asp Gln Lys Trp Thr Asp Met Tyr Gly Leu<br>690                                695                              700 | 2112 |
| atc gtc tcc cag tgg ttg tcc acc gtc aac acc cag ttc tac acc atc<br>Ile Val Ser Gln Trp Leu Ser Thr Val Asn Thr Gln Phe Tyr Thr Ile<br>705                                710                              715                            720 | 2160 |
| aag gag aga atg tac aac gcc ttg aac aac cag tcc cag gcc atc gag<br>Lys Glu Arg Met Tyr Asn Ala Leu Asn Asn Gln Ser Gln Ala Ile Glu<br>                          725                              730                              735 | 2208 |
| aag atc atc gag gac cag tac aac cgt tac tcc gag gag gac aag atg<br>Lys Ile Ile Glu Asp Gln Tyr Asn Arg Tyr Ser Glu Glu Asp Lys Met<br>740                                745                              750 | 2256 |
| aac atc aac atc gac ttc aac gac atc gac ttc aag ctg aac cag tcc<br>Asn Ile Asn Ile Asp Phe Asn Asp Ile Asp Phe Lys Leu Asn Gln Ser<br>755                                760                              765 | 2304 |
| atc aac ctg gcc atc aac aac atc gac gac ttc atc aac cag tgt tcc<br>Ile Asn Leu Ala Ile Asn Asn Ile Asp Asp Phe Ile Asn Gln Cys Ser<br>                          770                              775                              780 | 2352 |
| atc tcc tac ctg atg aac cgt atg atc cca ctg gcc gtc aag aag ttg<br>Ile Ser Tyr Leu Met Asn Arg Met Ile Pro Leu Ala Val Lys Lys Leu<br>785                                790                              795                            800 | 2400 |
| aag gac ttc gac gac aac ctg aag cgt gac ctg ctg gag tac atc gac<br>Lys Asp Phe Asp Asp Asn Leu Lys Arg Asp Leu Leu Glu Tyr Ile Asp<br>                          805                              810                              815 | 2448 |
| acc aac gag ttg tac ctg ctg gac gag gtc aac atc ttg aag tcc aag<br>Thr Asn Glu Leu Tyr Leu Leu Asp Glu Val Asn Ile Leu Lys Ser Lys<br>820                                825                              830 | 2496 |
| gtc aac aga cac ttg aag gac tcc atc cca ttc gac ttg tcc ttg tac<br>Val Asn Arg His Leu Lys Asp Ser Ile Pro Phe Asp Leu Ser Leu Tyr<br>835                                840                              845 | 2544 |
| acc<br>Thr | 2547 |

<210> SEQ ID NO 14
<211> LENGTH: 849
<212> TYPE: PRT
<213> ORGANISM: Clostridium botulinum

<400> SEQUENCE: 14

His Met Pro Val Asn Ile Lys Asn Phe Asn Tyr Asn Asp Pro Ile Asn
1                  5                    10                   15

Asn Asp Asp Ile Ile Met Met Glu Pro Phe Asn Asp Pro Gly Pro Gly
                  20                    25                    30

Thr Tyr Tyr Lys Ala Phe Arg Ile Ile Asp Arg Ile Trp Ile Val Pro

-continued

```
                35                  40                  45
Glu Arg Phe Thr Tyr Gly Phe Gln Pro Asp Gln Phe Asn Ala Ser Thr
 50                  55                  60

Gly Val Phe Ser Lys Asp Val Tyr Glu Tyr Tyr Asp Pro Thr Tyr Leu
 65                  70                  75                  80

Lys Thr Asp Ala Glu Lys Asp Lys Phe Leu Lys Thr Met Ile Lys Leu
                 85                  90                  95

Phe Asn Arg Ile Asn Ser Lys Pro Ser Gly Gln Arg Leu Leu Asp Met
                100                 105                 110

Ile Val Asp Ala Ile Pro Tyr Leu Gly Asn Ala Ser Thr Pro Pro Asp
                115                 120                 125

Lys Phe Ala Ala Asn Val Ala Asn Val Ser Ile Asn Lys Lys Ile Ile
130                 135                 140

Gln Pro Gly Ala Glu Asp Gln Ile Lys Gly Leu Met Thr Asn Leu Ile
145                 150                 155                 160

Ile Phe Gly Pro Gly Pro Val Leu Ser Asp Asn Phe Thr Asp Ser Met
                165                 170                 175

Ile Met Asn Gly His Ser Pro Ile Ser Glu Gly Phe Gly Ala Arg Met
                180                 185                 190

Met Ile Arg Phe Cys Pro Ser Cys Leu Asn Val Phe Asn Asn Val Gln
                195                 200                 205

Glu Asn Lys Asp Thr Ser Ile Phe Ser Arg Arg Ala Tyr Phe Ala Asp
                210                 215                 220

Pro Ala Leu Thr Leu Met His Glu Leu Ile His Val Leu His Gly Leu
225                 230                 235                 240

Tyr Gly Ile Lys Ile Ser Asn Leu Pro Ile Thr Pro Asn Thr Lys Glu
                245                 250                 255

Phe Phe Met Gln His Ser Asp Pro Val Gln Ala Glu Glu Leu Tyr Thr
                260                 265                 270

Phe Gly Gly His Asp Pro Ser Val Ile Ser Pro Ser Thr Asp Met Asn
                275                 280                 285

Ile Tyr Asn Lys Ala Leu Gln Asn Phe Gln Asp Ile Ala Asn Arg Leu
                290                 295                 300

Asn Ile Val Ser Ser Ala Gln Gly Ser Gly Ile Asp Ile Ser Leu Tyr
305                 310                 315                 320

Lys Gln Ile Tyr Lys Asn Lys Tyr Asp Phe Val Glu Asp Pro Asn Gly
                325                 330                 335

Lys Tyr Ser Val Asp Lys Asp Lys Phe Asp Lys Leu Tyr Lys Ala Leu
                340                 345                 350

Met Phe Gly Phe Thr Glu Thr Asn Leu Ala Gly Glu Tyr Gly Ile Lys
                355                 360                 365

Thr Arg Tyr Ser Tyr Phe Ser Glu Tyr Leu Pro Pro Ile Lys Thr Glu
370                 375                 380

Lys Leu Leu Asp Asn Thr Ile Tyr Thr Gln Asn Glu Gly Phe Asn Ile
385                 390                 395                 400

Ala Ser Lys Asn Leu Lys Thr Glu Phe Asn Gly Gln Asn Lys Ala Val
                405                 410                 415

Asn Lys Glu Ala Tyr Glu Glu Ile Ser Leu Glu His Leu Val Ile Tyr
                420                 425                 430

Arg Ile Ala Met Cys Lys Pro Val Met Tyr Lys Asn Thr Gly Lys Ser
                435                 440                 445

Glu Gln Cys Ile Ile Val Asn Asn Glu Asp Leu Phe Phe Ile Ala Asn
450                 455                 460
```

```
Lys Asp Ser Phe Ser Lys Asp Leu Ala Lys Ala Glu Thr Ile Ala Tyr
465                 470                 475                 480

Asn Thr Gln Asn Asn Thr Ile Glu Asn Asn Phe Ser Ile Asp Gln Leu
            485                 490                 495

Ile Leu Asp Asn Asp Leu Ser Ser Gly Ile Asp Leu Pro Asn Glu Asn
        500                 505                 510

Thr Glu Pro Phe Thr Asn Phe Asp Asp Ile Asp Ile Pro Val Tyr Ile
    515                 520                 525

Lys Gln Ser Ala Leu Lys Lys Ile Phe Val Asp Gly Asp Ser Leu Phe
530                 535                 540

Glu Tyr Leu His Ala Gln Thr Phe Pro Ser Asn Ile Glu Asn Gln Leu
545                 550                 555                 560

Thr Asn Ser Leu Asn Asp Ala Leu Arg Asn Asn Asn Lys Val Tyr Thr
                565                 570                 575

Phe Phe Ser Thr Asn Leu Val Glu Lys Ala Asn Thr Val Val Gly Ala
            580                 585                 590

Ser Leu Phe Val Asn Trp Val Lys Gly Val Ile Asp Asp Phe Thr Ser
        595                 600                 605

Glu Ser Thr Gln Lys Ser Thr Ile Asp Lys Val Ser Asp Val Ser Ile
610                 615                 620

Ile Ile Pro Tyr Ile Gly Pro Ala Leu Asn Val Gly Asn Glu Thr Ala
625                 630                 635                 640

Lys Glu Asn Phe Lys Asn Ala Phe Glu Ile Gly Gly Ala Ala Ile Leu
                645                 650                 655

Met Glu Phe Ile Pro Glu Leu Ile Val Pro Ile Val Gly Phe Phe Thr
            660                 665                 670

Leu Glu Ser Tyr Val Gly Asn Lys Gly His Ile Ile Met Thr Ile Ser
        675                 680                 685

Asn Ala Leu Lys Lys Arg Asp Gln Lys Trp Thr Asp Met Tyr Gly Leu
690                 695                 700

Ile Val Ser Gln Trp Leu Ser Thr Val Asn Thr Gln Phe Tyr Thr Ile
705                 710                 715                 720

Lys Glu Arg Met Tyr Asn Ala Leu Asn Asn Gln Ser Gln Ala Ile Glu
                725                 730                 735

Lys Ile Ile Glu Asp Gln Tyr Asn Arg Tyr Ser Glu Glu Asp Lys Met
            740                 745                 750

Asn Ile Asn Ile Asp Phe Asn Asp Ile Asp Phe Lys Leu Asn Gln Ser
        755                 760                 765

Ile Asn Leu Ala Ile Asn Asn Ile Asp Asp Phe Ile Asn Gln Cys Ser
770                 775                 780

Ile Ser Tyr Leu Met Asn Arg Met Ile Pro Leu Ala Val Lys Lys Leu
785                 790                 795                 800

Lys Asp Phe Asp Asp Asn Leu Lys Arg Asp Leu Leu Glu Tyr Ile Asp
                805                 810                 815

Thr Asn Glu Leu Tyr Leu Leu Asp Glu Val Asn Ile Leu Lys Ser Lys
            820                 825                 830

Val Asn Arg His Leu Lys Asp Ser Ile Pro Phe Asp Leu Ser Leu Tyr
        835                 840                 845

Thr

<210> SEQ ID NO 15
<211> LENGTH: 603
<212> TYPE: DNA
<213> ORGANISM: Mus musculus
<220> FEATURE:
```

```
<221> NAME/KEY: CDS
<222> LOCATION: (1)..(600)

<400> SEQUENCE: 15 atg cgt aat gaa ctg gag gag atg cag agg agg gct gac cag ctg gct        48
Met Arg Asn Glu Leu Glu Glu Met Gln Arg Arg Ala Asp Gln Leu Ala
1               5                   10                  15 gat gag tcc ctg gaa agc acc cgt cgc atg ctg cag ctg gtc gaa gag        96
Asp Glu Ser Leu Glu Ser Thr Arg Arg Met Leu Gln Leu Val Glu Glu
            20                  25                  30 agt aaa gat gct ggc atc agg act ttg gtt atg ttg gat gag caa ggc       144
Ser Lys Asp Ala Gly Ile Arg Thr Leu Val Met Leu Asp Glu Gln Gly
        35                  40                  45 gaa caa ctg gaa cgc att gag gaa ggg atg gac caa atc aat aag gat       192
Glu Gln Leu Glu Arg Ile Glu Glu Gly Met Asp Gln Ile Asn Lys Asp
    50                  55                  60 atg aaa gaa gca gaa aag aat ttg acg gac cta gga aaa ttc tgc ggg       240
Met Lys Glu Ala Glu Lys Asn Leu Thr Asp Leu Gly Lys Phe Cys Gly
65                  70                  75                  80 ctt tgt gtg tgt ccc tgt aac aag ctt aaa tcc agt gat gct tac aaa       288
Leu Cys Val Cys Pro Cys Asn Lys Leu Lys Ser Ser Asp Ala Tyr Lys
                85                  90                  95 aaa gcc tgg ggc aat aat cag gat gga gta gtg gcc agc cag cct gcc       336
Lys Ala Trp Gly Asn Asn Gln Asp Gly Val Val Ala Ser Gln Pro Ala
            100                 105                 110 cgt gtg gtg gat gaa cgg gag cag atg gcc atc agt ggt ggc ttc atc       384
Arg Val Val Asp Glu Arg Glu Gln Met Ala Ile Ser Gly Gly Phe Ile
        115                 120                 125 cgc agg gta aca aac gat gcc cgg gaa aat gaa atg gat gaa aac cta       432
Arg Arg Val Thr Asn Asp Ala Arg Glu Asn Glu Met Asp Glu Asn Leu
    130                 135                 140 gag cag gtg agc ggc atc atc gga aac ctc cgt cat atg gcc cta gac       480
Glu Gln Val Ser Gly Ile Ile Gly Asn Leu Arg His Met Ala Leu Asp
145                 150                 155                 160 atg ggc aat gag att gac acc cag aat cgc cag att gac agg atc atg       528
Met Gly Asn Glu Ile Asp Thr Gln Asn Arg Gln Ile Asp Arg Ile Met
                165                 170                 175 gag aag gct gac tcc aac aaa acc aga att gat gaa gcc aac caa cgt       576
Glu Lys Ala Asp Ser Asn Lys Thr Arg Ile Asp Glu Ala Asn Gln Arg
            180                 185                 190 gca aca aag atg ctg gga agt ggt taa                                    603
Ala Thr Lys Met Leu Gly Ser Gly
        195                 200

<210> SEQ ID NO 16
<211> LENGTH: 200
<212> TYPE: PRT
<213> ORGANISM: Mus musculus

<400> SEQUENCE: 16

Met Arg Asn Glu Leu Glu Glu Met Gln Arg Arg Ala Asp Gln Leu Ala
1               5                   10                  15

Asp Glu Ser Leu Glu Ser Thr Arg Arg Met Leu Gln Leu Val Glu Glu
            20                  25                  30

Ser Lys Asp Ala Gly Ile Arg Thr Leu Val Met Leu Asp Glu Gln Gly
        35                  40                  45

Glu Gln Leu Glu Arg Ile Glu Glu Gly Met Asp Gln Ile Asn Lys Asp
    50                  55                  60

Met Lys Glu Ala Glu Lys Asn Leu Thr Asp Leu Gly Lys Phe Cys Gly
65                  70                  75                  80
```

-continued

```
Leu Cys Val Cys Pro Cys Asn Lys Leu Lys Ser Ser Asp Ala Tyr Lys
                85                  90                  95

Lys Ala Trp Gly Asn Asn Gln Asp Gly Val Val Ala Ser Gln Pro Ala
            100                 105                 110

Arg Val Val Asp Glu Arg Glu Gln Met Ala Ile Ser Gly Gly Phe Ile
        115                 120                 125

Arg Arg Val Thr Asn Asp Ala Arg Glu Asn Glu Met Asp Glu Asn Leu
    130                 135                 140

Glu Gln Val Ser Gly Ile Ile Gly Asn Leu Arg His Met Ala Leu Asp
145                 150                 155                 160

Met Gly Asn Glu Ile Asp Thr Gln Asn Arg Gln Ile Asp Arg Ile Met
                165                 170                 175

Glu Lys Ala Asp Ser Asn Lys Thr Arg Ile Asp Glu Ala Asn Gln Arg
            180                 185                 190

Ala Thr Lys Met Leu Gly Ser Gly
        195                 200
```

METHODS FOR IDENTIFYING INHIBITORS OF BOTULINUM NEUROTOXINS

This application is a division of and claims priority under 35 U.S.C. §120 and §121 from co-owned U.S. patent application Ser. No. 11/095,055, filed with the United States Patent and Trademark Office Mar. 31, 2005, issued as U.S. Pat. No. 7,632,917B2 on Dec. 15, 2009, which is a continuation of PCT Application No. PCT/US2003/030899 filed Oct. 3, 2003, which, in turn, claims the benefit of U.S. Provisional Application No. 60/415,177 filed Oct. 1, 2002, all of which are incorporated herein by reference in their entirety.

BACKGROUND

1. Field of Invention

This invention relates to a method for identifying inhibitors of botulinum neurotoxins.

2. Background of the Invention

Botulinum neurotoxins (BoNT) and tetanus neurotoxin (TeNT) are bacterial proteins that comprise two polypeptide chains connected via a disulfide linkage. The light chain (~50 kDa) is disulfide linked to a heavy chain (~100 kDa). The anaerobic bacterium *Clostridium botulinum* produces seven immunologically distinct but structurally similar neurotoxins designated BoNT/A, BoNT/B, BoNT/C, BoNT/D, BoNT/E, BoNT/F and BoNT/G (collectively, "BoNTs"). After synthesis, highly active neurotoxin is generated by proteolytic cleavage of the clostridial neurotoxins.

These neurotoxins inhibit neurotransmitter release at distinct synapses, which causes two severe neuroparalytic diseases, tetanus and botulism. Many aspects of the cellular and molecular modes of action of these toxins have been deciphered. After binding to specific membrane acceptors, BoNTs and TeNT are internalized via endocytosis into nerve terminals. Internalization of toxin is a rapid event and the toxin shows persistent catalytic activity within neurons. Subsequently, the light chain of the neurotoxin is translocated into the cytosolic compartment where it cleaves one of three essential proteins involved in the exocytotic machinery: (1) synaptosomal associated protein of 25 kDa (SNAP-25); (2) synaptobrevin, also called vesicle associated membrane protein (VAMP); and (3) syntaxin. Specifically, BoNT/A, BoNT/E and BoNT/C cleave SNAP-25; BoNT/C also cleaves syntaxin. BoNT/B, BoNT/D, BoNT/F, BoNT/G cleave synaptobrevin/VAMP. Tetanus neurotoxin cleaves synaptobrevin/VAMP at the same cleavage site as BoNT/B. See, Schmidt J J, et al., supra; Anne C, et al., Anal Biochem (2001 291:253-61).

The location of the enzymatic subunit of the clostridial neurotoxins has been mapped to the light chain, which has Zn endopeptidase activity. The binding and translocation motifs in a BoNT are located within the heavy (H) chain. All of the BoNT serotypes bind to receptors/acceptors on the presynaptic terminals of motor neurons at the neuromuscular junction. Schiavo G, et al., (1993) FEBS Lett 335:99-103. The binding of the BoNT to the presynaptic terminal is mediated by the C-terminal domain of the heavy chain (HC) of the toxin. Schiavo G, et al., J Biol Chem (1993) 268: 23784-7 and Schiavo G, et al., Nature (1992) 359: 832-5. Binding is followed by endocytosis of the toxin into vesicles at the presynaptic terminal. As the endocytotic vesicle is acidified, the N-terminus of the HC forms a pore in the vesicle membrane. The light chain (LC) disassociates from HC to act as a zinc-dependent protease that cleaves and inactivates SNARE proteins essential for exocytosis of neurotransmitter. Arnon S S, et al., JAMA 2001, 285:1059-70. In the case of BoNT/A (the most potent and persistent of the BoNTs) the substrate is SNAP-25, a SNARE protein which resides on the cytoplasmic surface of the presynaptic membrane. See, Foran P, et al., Biochemistry (1996) 35:2630-6; Lewis J, et al., Nat Med (1999) 5:832-5; and Schmidt J J, et al., Anal Biochem (2001) 296:130-7.

The botulinum neurotoxin cleaves the substrate proteins at highly specific sites. BoNT/A cleaves SNAP-25 at residues 197/198 (amino acids QR). See, Foran P, et al., Biochemistry (1996) 35:2630-6; and Lewis J, et al., (1999) supra. BoNT/E cleaves SNAP-25 at residues 180/181 (amino acids RI).

The unique specificities of BoNT/A and BoNT/E for SNAP-25 was suggested to be directed through the recognition of a nine residue sequence, termed the SNARE motif. The SNARE motif is about 50 amino acids in length and assumes a coiled confirmation. The SNARE motif in SNAP-25 is common to the other two SNARE proteins: VAMP and syntaxin. SNAP-25, VAMP and syntaxin are the only known substrates of the seven clostridial neurotoxins. There are four copies of the SNARE motif present in SNAP-25. Studies on the interaction of SNAP-25 with BoNT/A and BoNT/E showed that a single copy of the motif is sufficient for BoNT/A and BoNT/E to recognize SNAP-25. Washbourne P et al., FEBS Lett. (1997) 418:1-5. The full kinetic activity of BoNT/A and BoNT/E for SNAP-25 requires at least one SNARE motif. Although the copy of the SNARE motif that is proximal to the SNAP-25 cleavage site is clearly involved in recognition with BoNT/A and BoNT/E, in its absence, other more distant copies of the motif are able to support proteolysis. Id.

The proteolytic attack at specific sites in the protein targets for BoNTs and TeNT induces perturbations of the fusogenic SNARE complex dynamics. These alterations can account for the inhibition of spontaneous and evoked quantal neurotransmitter release caused by the neurotoxins.

The botulinum neurotoxins (BoNTs) are some of the most potent and persistent toxins known and can be delivered by an oral or inhalation route. These properties have contributed to attempts by others to use BoNT as a bioweapon. No effective antidote for BoNT intoxication is available. Current therapy consists primarily of long term ventilator support, although early administration of hyperimmune antiserum within the first 12 hours can shorten the duration of paralysis. This therapy currently involves administration of horse serum derived antibodies with the risks of anaphylactic reaction. Human hyperimmune antiserum is used to treat infantile botulism. Human hyperimmune antiserum is too limited a source for use in a bioterrorism attack involving BoNT. Monoclonal IgG antitoxins are being pursued for BoNT therapy, but at least three different monoclonal antibodies are required to inhibit each of the serotypes of botulinum neurotoxin. The cost of producing an oligoclonal treatment consisting of 15-18 monoclonal antibodies is not commercially feasible.

Immunization is currently the major biodefense strategy against BoNT attacks. Although vaccination can clearly protect against the paralytic effects of the toxin, there are clear limitations to this strategy which include: 1) the need to vaccinate a large at risk population to prevent disease in even a small number of exposed individuals; 2) active vaccination must be accomplished well before exposure to the toxin; 3) strains of BoNT can be engineered for bioterrorism, that can evade immune defense or delivered by viral vector overcoming host immunity (See Fishman P S, et al., Nat Toxins 1999, 7:151-6), and; 4) vaccination will interfere with the potential future use of BoNT for medical conditions and deny the current standard of care to immunized patients. Oyler G A, et al., IBRCC (2001).

An alternative strategy to vaccination against BoNT is the development of a clinically useful antidote. Oyler GA, et al., Interagency Botulinum Research Coordinating Committee, 2001. This strategy opens a wide array of possibilities based on the understanding of the molecular pathogenesis of intoxication.

Methods to detect botulinum neurotoxin's catalytic activity have been based on detecting SNARE protein cleavage products in vitro. See, for example, Schmidt U.S. Pat. No. 5,965,699, the contents of which are hereby incorporated by reference in their entirety.

The blocking proteolytic activity of the catalytic light chain is a candidate for treatments to inhibit and terminate the action of the toxin. SNARE protein cleavage is a late event in intoxication.

Rapid replenishment of SNARE proteins normally occurs and could result in early restoration of neuromuscular synaptic function. Inhibitors that are able to reach the site of action in the cytosolic compartment of the pre-synaptic terminal of the neuromuscular junction (unprotected by the blood-brain/nerve-barrier) could decrease the neurotoxin's effect in infected individuals. There is a need for a method to identify a clinically relevant botulinum catalytic inhibitor that penetrates to the intracellular site of action of the toxin and is non-toxic to living cells. Therefore, a need exists for a method for screening inhibitors of botulinum neurotoxin type A (BoNT/A), to identify neurotoxin inhibitors that function both in vitro and in living cells. There is also a need for a method of screening inhibitors of botulinum neurotoxin type E (BoNT/E), type C (BoNT/C), type B (BoNT/B), type D (BoNT/D), type F (BoNT/F) and type G (BoNT/G) that can be used to identify neurotoxin inhibitors that function both in vitro and in living cells. In order to facilitate the identification and development of such botulinum toxin inhibitors, there is a need for a system to rapidly assess botulinum toxin catalytic activity.

BRIEF DESCRIPTION OF THE DRAWINGS

FIGS. 3A and 3B show the results of the in-vitro assay for BoNT catalytic activity. YFP-SNAP-25-Hisx6 immobilized on Nickel resin were incubated with BoNT/A at 37° C. for 4 hours without agitation. The amount of YFP fluorescence released into the supernatant was monitored with a fluorescence plate reader. The assay was sensitive enough to detect 0.1 U/mL and 1.0 U/mL (1.0 ng/mL and 5.0 ng/mL) of BoNT/A.

FIG. 4A shows the results of a assays in which synthetic BoNT/A LC is expressed in mammalian cells and catalytically active. In FIG. 4A, mouse brain extract was incubated with lysates prepared from HEK 293 cells that were transiently transfected with BoNT/A LC. Immunoblots showed that mouse endogenous SNAP-25 was cleaved by the BoNT/A LC expressed in HEK 293 cells. FIG. 4B shows the results of assays employing primary neuronal cultures and HEK 293 cells stably expressing YFP-SNAP-25-Hisx6. Both types of cell cultures were infected with a Sindbis virus overexpressing BoNT/A LC (moi 5) and analyzed for SNAP-25 cleavage by immunoblot. The synthetic BoNT/A LC was efficiently expressed and cleaved both endogenous neuronal SNAP-25 and YFP-SNAP-25-Hisx6.

FIG. 6 shows is a schematic illustration of the cell-based assay for BoNT catalytic activity. HEK 293 cells stably expressing YFP-SNAP-25-Hisx6 are exposed to BoNT and the amount of YFP-SNAP-25-Hisx6 cleavage monitored by the quantity of YFP fluorescence bound to Nickel resin. A high-throughput cell-based assay uses a similar assay platform to that used in the in-vitro assay, to monitor the neurotoxin proteolytic activity on a substrate located in cells.

FIGS. 8A and 8B are the synthetic BoNT/A and BoNT/E sequences, respectively in which the BamHI and AccIII restriction enzymes sites are identified.

DETAILED DESCRIPTION OF THE INVENTION

This present invention is the first system for screening inhibitors of botulinum neurotoxin type A (BoNT/A) for use in both in vitro and in living cells. Such a system can be used to greatly accelerate the search for a clinically useful antidote to botulism.

All references cited herein are hereby incorporated by reference in their entirety.

This is a novel system for monitoring the catalytic activity of a BoNT both in vitro and within living cells. The system is designed to facilitate the identification of clinically useful antidotes for botulinum neurotoxin type A and can be adapted for use as a high throughput screening assay system.

The system of the present invention provides a method for detecting BoNT activity and identifying inhibitors of BoNT activity by monitoring the cleavage of the neurotoxin's endogenous substrate using a novel recombinant protein, referred to as a botulinum neurotoxin substrate complex (or substrate indicator protein). The botulinum neurotoxin substrate complex of the present invention is comprised of: (a) a peptide substrate that is capable of being cleaved at a specific cleavage site by a botulinum neurotoxin; (b) a reporter domain on one side of the peptide substrate; and (c) an immobilization domain on the opposite side of the peptide substrate. The preferred peptide substrates are SNAP-25, a SNAP-25 isoform, syntaxin, a syntaxin isoform, VAMP, a VAMP isoform, and peptides having at least 80% identity to the foregoing as long as the peptide substrate is capable of being cleaved at a specific cleavage site by a botulinum neurotoxin. The more preferred peptide substrates are SNAP-25, syntaxin and VAMP. The most preferred peptide substrate is SNAP-25 because it is the endogenous substrate of BoNT/A and BoNT/E, which are the two serotypes that account for the majority of botulinum infections. The nucleotide and amino acid sequence encoding murine SNAP-25 is shown in SEQ ID No. 15 and SEQ ID No. 16, respectively.

Figure 1:
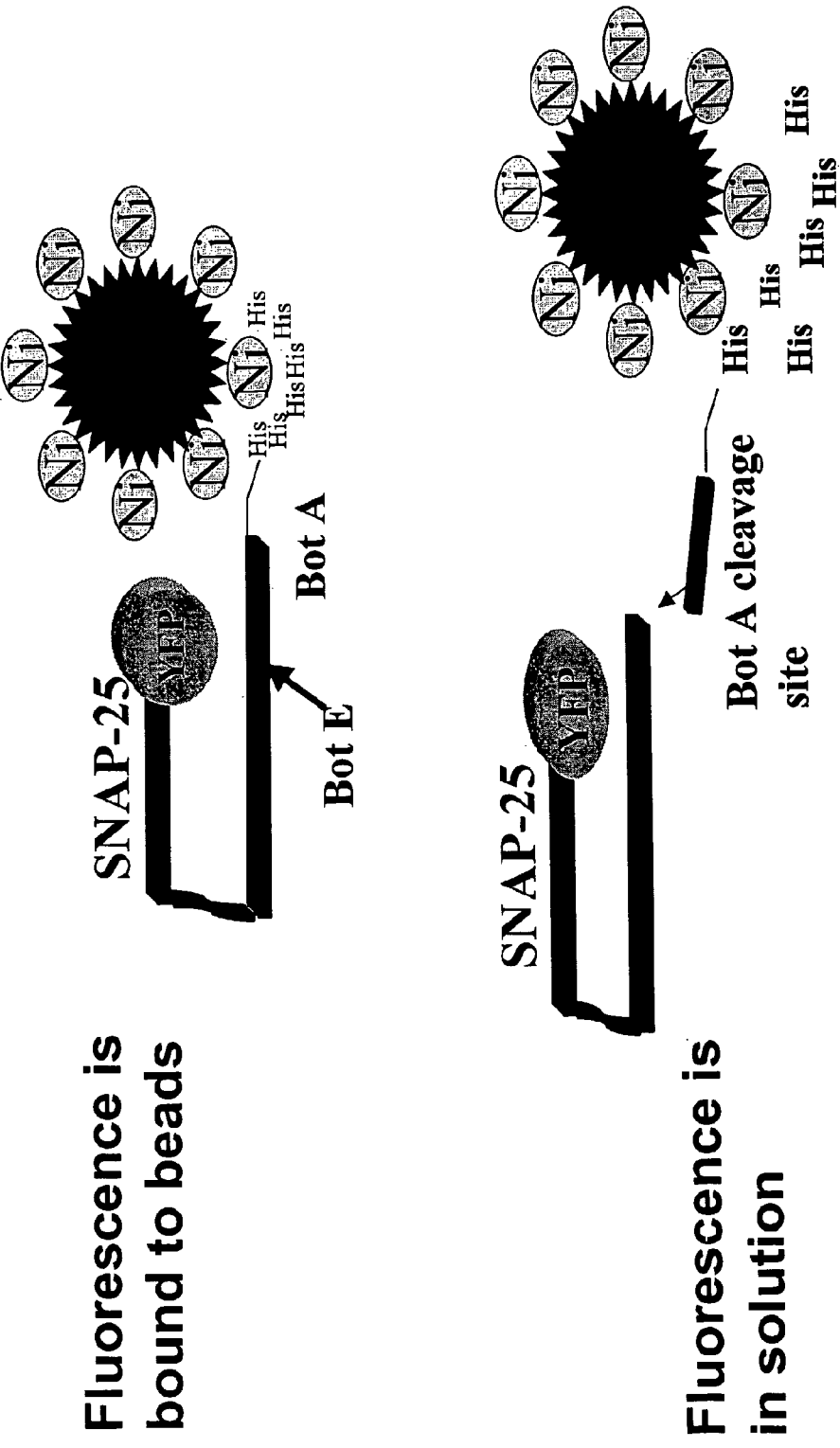
FIG. 1 is a design of an in-vitro assay for BoNT catalytic activity. The in-vitro assay for BoNT activity based on separation of a reporter domain and immobilization domain upon cleavage of SNAP-25 by BoNT. Cleavage of YFP-SNAP-25-Hisx6 immobilized on metal ion resin by BoNT releases yellow fluorescent protein (YFP) into the supernatant, which can be monitored by YFP fluorescence.

The system of the present invention for detecting BoNT/A or BoNT/E activity and identifying inhibitors of BoNT/A or BoNT/E activity is based on methods for monitoring the cleavage of their endogenous substrate SNAP-25. The system of the present invention monitors the proteolytic cleavage of SNAP-25 using a novel recombinant protein, referred to as a botulinum neurotoxin substrate complex. In one embodiment of the SNAP-25 botulinum neurotoxin substrate complex (YFP-SNAP-25-Hisx6), the complex is comprised of the protein substrate SNAP-25, which has a hexahistidine peptide (Hisx6) immobilization domain at its carboxyl terminus and a yellow fluorescent protein (YFP) reporter domain at its amino-terminus. The YFP-SNAP-25-Hisx6 example of a botulinum neurotoxin substrate complex is illustrated graphically in FIG. 1. This YFP-SNAP-25-Hisx6 system can also be used to detect BoNT/C activity and identify inhibitors of BoNT/C.

The YFP-SNAP-25-Hisx6 complex is capable of binding to nickel resin beads through its C-terminal Hisx6 immobilization domain of the complex. Nickel resin coated 96 well microtiter plates are suitable for high throughput screening and are commercially available (Pierce). The YFP-SNAP-25-Hisx6 complex is bound to the nickel resin in the wells of the plate. In the presence of BoNT/A, BoNT/C, or BoNT/E, the complex is cleaved to produce a cleaved complex, liberating the fluorescent indicator YFP reporter domain into the supernatant and leaving the immobilized domain bound to the Nickel. The remaining intact complex (containing the reporter domain) present on the plates and/or the reporter domain released into the supernatant can be monitored; the YFP reporter is monitored by YFP fluorescence. There is an inverse correlation between toxin concentration in the well and YFP fluorescence bound to plate. In other words, the greater the concentration of BoNT, the lower the concentration of YFP-SNAP-25-Hisx6 complex bound to the plate because the toxin releases the YFP reporter domain from the plate.

This approach confers a substantial advantage over other BoNT assays by capturing the "free" (proteolytically-liberated) portion containing fluorescence, enzyme activity or other detection signature. This strategy improves assay sensitivity and reduces background, thus permitting even very low amounts of the (proteolyzed) product to be measured. The complex is immobilized on a nickel surface through a C-terminal hexahistadine immobilization domain. This approach effectively removes unwanted background materials from the test sample and permits the reduction in bound reporter domain in the immobilized complex to be measured.

The system of the present invention further provides methods adapted for cell based screening to monitor the catalytic activity of a BoNT in living cells and to identify molecules that inhibit the catalytic activity of a BoNT in living cells. The present invention provides novel stable cell lines that express the botulinum toxin substrate complex (e.g., YFP-SNAP25-Hisx6 or GST-SNAP25-Hisx6). In one embodiment of the present invention, a viral vector capable of efficiently expressing an active light chain of BoNT within mammalian cells is provided.

Both the botulinum toxin substrate complex component and the BoNT expressing viral vector component of the system are suitable for use in high throughput methods. Commercially available multi-titer plates coated with nickel resin are capable of binding to the substrate indicator protein (i.e., the neurotoxin substrate complex) of the present invention. Stable YFP-SNAP-25-Hisx6 expressing cell lines will grow consistently within multi-titer plates as well. Plates of such cell lines allow for simultaneous, consistent infection with Sindbis virus expressing the synthetic BoNT LC in all wells. These dually expressing cells create multiple replicates per plate, where each well is available as a test vessel for a putative BoNT inhibitor. Also, lysates from such cells can be incubated and washed in the resin coated wells and the plates can be assessed for bound YFP fluorescence using a multi-well fluourimeter. Libraries of compounds, having established or potential inhibitory properties for metal protease, can be screened for their potency as a BoNT inhibitor. A compound identified as a BoNT inhibitor can be developed for use as a BoNT antidote.

EXAMPLE 1

Construction and Expression of YFP-SNAP-25-Hisx6

To construct YFP-SNAP25-Hisx6, PCR is used to generate Hisx6 tag (histidine tag) at the carboxyl terminus of mouse SNAP-25 (shown in SEQ ID No. 16) and ligated into EYFP-C1 vector (Clontech). Similar constructs can be made with GST reporter domain encoding vectors. For bacterial expression, PCR is used to generate YFP-SNAP25-Hisx6 with appropriate restriction sites and cloned into pGEX4T3 vector (Amersham Pharmacia Biotech). The protein is expressed in BL21(DE3) (Stratagene) bacteria and purified with glutathione sepharose 4B (AP Biotech) and the GST motif removed with thrombin cleavage. YFP-SNAP-25-Hisx6 is also cloned into pET vector (Novagen), expressed in BL21 (DE3) bacteria and purified by nickel affinity chromatography. The in-vitro assay described below uses the protein purified from pGEX vector.

EXAMPLE 2

Generation of YFP-SNAP-25-Hisx6 Cell-Lines

HEK 293 cells were cultured in Minimum Essential Medium (GIBCO) supplemented with 10% fetal bovine serum, L-glutamine (10%) and pen/strep antibiotics (1%). HEK 293 cells were transfected with YFP-SNAP-25-Hisx6 plasmid and cultured in media containing G418 until isolated foci emerged. Isolated foci were selected for expansion and screened by immunoblots to obtain clonal cell-lines stably expressing YFP-SNAP-25-Hisx6.

EXAMPLE 3

Viral RNA Transcription, Transfection and Plaque Assays

Purified plasmid DNAs were linearized by digestion with XhoI and transcribed using SP6 polymerase in the presence of cap analog. Transcription reactions were used for transfection of BHK-21 cells using standard methods. BHK-21 cells (ATCC) were cultured in Dubelco's Minimum Essential Medium (GIBCO) supplemented with 10% fetal bovine serum, L-glutamine (10%) and pen/strep antibiotics (1%). Plaque formation was assayed using BHK-21 monolayers.

EXAMPLE 4

In Vitro Assay for BoNT Catalytic Activity

The catalytic activity of BoNT/A was assayed using YFP-SNAP-25-Hisx6 immobilized on Nickel resin in 96-well plates. Purified YFP-SNAP-25-Hisx6 protein was immobilized on the resin and washed extensively in PBS. BoNT/A was added in the range of 1-100 U/mL PBS. The plates were incubated at 37° C. without agitation. The reaction was quenched with EDTA and the supernatant monitored for YFP fluorescence in a fluorescence plate reader.

The basis for the detection of BoNT A or E activity is the cleavage of SNAP-25. Cleavage is monitored with a novel recombinant protein where SNAP-25 has a hexahistidine peptide ("Hisx6" or "histadine tag") fused to its carboxyl terminus and the yellow fluorescent protein (YFP) fused to its amino-terminus (YFP-SNAP-25-Hisx6, FIG. 1). The histadine tag molecule binds to nickel resin beads through its C-terminal Hisx6. Such nickel resin is bound to 96 well microtiter plates, which are commercially available (Pierce) and suitable for high throughput screening. In the presence of BoNT A, C, or E, the bound YFP-SNAP-25-Hisx6 is cleaved, liberating the fluorescent indicator YFP domain. There is an inverse correlation between toxin concentration in the well and YFP fluorescence bound to plate. In other words, the greater the concentration of toxin, the lower the concentration of YFP-SNAP-25 bound to the plate because the toxin releases the YFP reporter/signal from the plate.

The YFP-SNAP-25-Hisx6 immobilized on metal ion resin is cleaved by BoNT, which separates the reporter domain from the immobilization domain and releases the YFP reporter domain into the supernatant (leaving the immobilization domain attached to the metal ion resin). The YFP reporter can be monitored by YFP fluorescence.

FIGS. 2A, 2B, 2C, 2D, 2E, and 2F show the results of experiments conducted to determine if the YFP or GST added to the N-terminus of SNAP-25 and the charged hexahistidine group at the C-terminus of SNAP-25 effects the sensitivity of SNAP-25 to BoNT cleavage. BoNT/A cleaves SNAP-25 only 7 amino-acids from its C-terminus. Each of GST-SNAP-25, GST-SNAP-25-Hisx6 and YFP-SNAP-25-Hisx6 were purified from bacterial expression.

Figure 2:
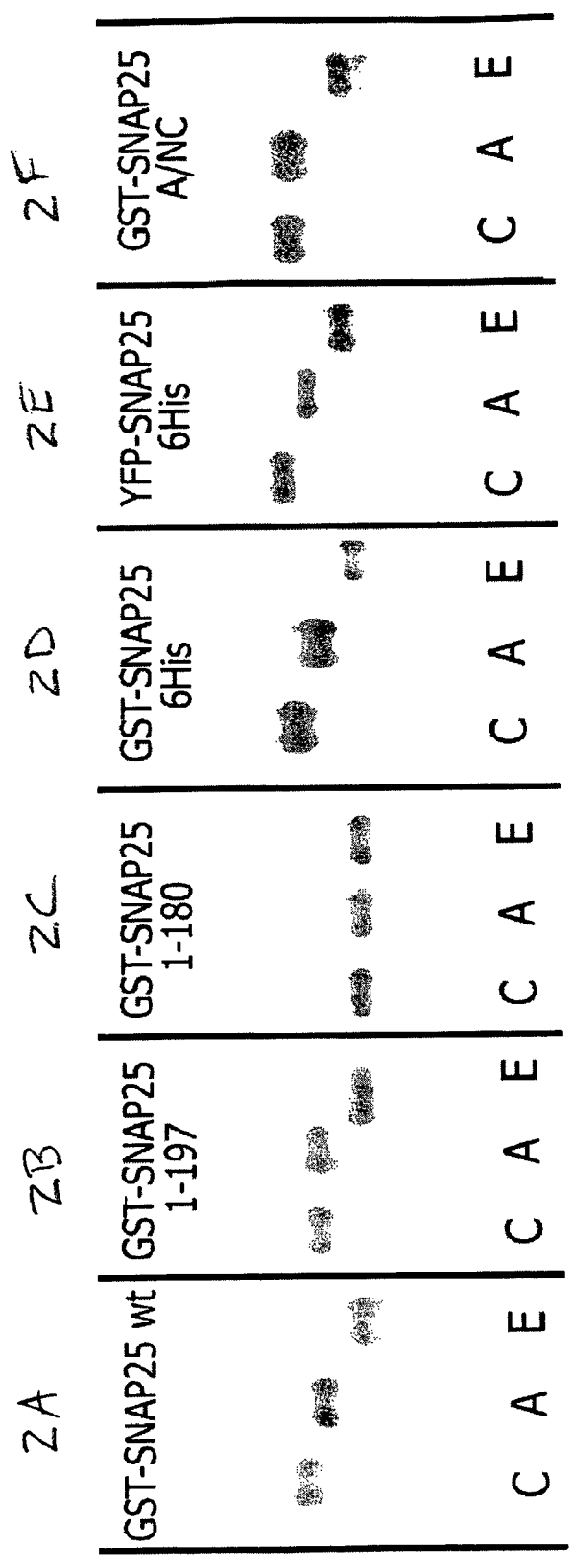
FIG. 2 is comprised of FIGS. 2A, 2B, 2C, 2D, 2E, and 2F. Cleavage of YFP-SNAP-25-Hisx6 by BoNT/A and E, compared to a Control (C) is shown in FIG. 2E. GST-SNAP-25, GST-SNAP-25-Hisx6 and YFP-SNAP-25-Hisx6 were efficiently cleaved by BoNT/A and E in vitro (FIGS. 2A and 2D, respectively). GST-SNAP-25 (1-197) and GST-SNAP-25 (1-180) are recombinant proteins corresponding to the cleaved fragments from BoNT/A and E cleavage, respectively (FIGS. 2B and 2C). GST-SNAP-25 A/NC, which harbors a single point mutation (R198T) that renders it BoNT/A resistant, was cleaved only by BoNT/E in this assay (FIG. 2F).

We first demonstrated that BoNT/A and BoNT/E efficiently cleave each of GST-SNAP-25, GST-SNAP-25-Hisx6 and YFP-SNAP-25-Hisx6 in-vitro, as shown in FIGS. 2A, 2D and 2E, respectively. Cleavage of YFP-SNAP-25-Hisx6 by BoNT/A and E is shown in FIG. 2A, and FIGS. 2D-2F. GST-SNAP-25, GST-SNAP-25-Hisx6 and YFP-SNAP-25-Hisx6 were efficiently cleaved by BoNT/A and E in vitro. GST-SNAP-25 (1-197) and GST-SNAP-25 (1-180) are recombinant proteins corresponding to the cleaved fragments from BoNT/A and E cleavage respectively. GST-SNAP-25 A/NC, which harbors a single point mutation (R198T), renders it BoNT/A resistant, was cleaved only by BoNT/E in this assay. GST-SNAP-25 (1-197) is the cleavage fragment from BoNT/A cleavage of the recombinant protein GST-SNAP-25. GST-SNAP-25 (1-180) is the cleavage fragment from BoNT/E cleavage of the recombinant protein GST-SNAP-25.

A single point mutation in SNAP-25 (R198T) renders SNAP-25 resistant to BoNT/A, but sensitive to cleavage by BoNT/E. In this assay, GST-SNAP-25 A/NC is resistant to BoNT/A cleavage, yet sensitive to cleavage by BoNT/E.

A single point mutation in SNAP-25 (D179K) renders SNAP-25 resistant to BoNT/E, but sensitive to cleavage by BoNT/A. An assay employing GST-SNAP-25 (D179K) can be tested to determine if the fusion protein is resistant to BoNT/E cleavage while remaining sensitive to BoNT/A.

A double point mutation in SNAP-25 (D179K and R198T) renders SNAP-25 resistant to both BoNT/A and BoNT/E.

To evaluate the sensitivity of an in-vitro assay based on cleavage of YFP-SNAP-25-Hisx6, we incubated 96-well plates coated with YFP-SNAP-25-Hisx6 with 1-100 U/mL BoNT/A and measured the amount of fluorescence released into the supernatant. At 4 hours, YFP fluorescence released into the supernatant increases almost 10 fold over background in the treated wells. Control wells containing no toxin or varying quantities from 0.1 U/mL to 100 U/mL (i.e., 1.0 ng/ml to 100.0 ng/ml) of BoNT/A pre-inactivated by boiling for 5 min show minimal release of YFP fluorescence (FIGS. 3A and 3B). FIGS. 3A and 3B show the in-vitro assay for BoNT catalytic activity. YFP-SNAP-25-Hisx6 immobilized on Nickel resin were incubated with BoNT/A at 37° C. for 4 hours without agitation. The amount of YFP fluorescence released into the supernatant was monitored with a fluorescence plate reader. The pilot assay format was sensitive enough to detect 0.1 U/mL of BoNT/A. The assay therefore exhibits sensitivity down to 0.1 U/mL of BoNT/A.

High-throughput screening of inhibitors of BoNT can be achieved by incubating YFP-SNAP-25-Hisx6 coated plates with BoNT and a putative toxin inhibitor. Efficacy of any inhibitor of the catalytic activity of BoNT for SNAP-25 cleavage would be proportional to the increase of bound fluorescence toward that seen in control wells without toxin. This approach confers a substantial advantage over other BoNT assays by capturing the "free" (proteolytically-liberated) portion containing fluorescence, enzyme activity or other detection signature. This strategy improves assay sensitivity and reduces background, thus permitting even very low amounts of the (proteolyzed) product to be measured.

In one embodiment, intact target protein is immobilized on a nickel surface through a C-terminal 6× his tag. This approach effectively removes unwanted background materials from the test sample by measuring the reduction in bound activity in the immobilized complex. The method of the present invention can measure both the loss of fluorescence from the beads as the substrate is cleaved and the increase in free fluorescence in solution. There is also a measurable loss of fluorescence from beads. In one embodiment of the high throughput assay method of the present invention, Nickel beads are incubated with a solution containing excess GST-YFP-SNAP25-6×His before the beads are washed in order to load the beads to maximum capacity. The fluorescence of the loaded beads is measured before they are incubated with Bo/NT and the fluorescence is measured again. The amount of loss of fluorescence is proportional to the amount of Bo/NT added. Also the fluorescence liberated into solution is measure to determine the increase in fluorescence released into solution.

EXAMPLE 5

Cell-Based Assay for BoNT Catalytic Activity

HEK 293 cells stably expressing YFP-SNAP-25-Hisx6 were infected with Sindbis virus overexpressing catalytic BoNT/A LC at multiplicity of infection of 5. At the termination of such a test run, the cells were lysed in a lysis buffer containing 20 mM Tris (pH 7.5), 150 mM NaCl, 0.1% NP-40 and protease inhibitors. The lysate was applied to Nickel resin followed by extensive washes in Tris-buffered saline. YFP fluorescence in the flow through or bound to the resin was measured using a fluorescence plate reader. This assay can be performed in multi-well plates and the lysis buffer is added to the wells after the YFP-SNAP-25-Hisx6 expressing cells are infected with the BoNT/A expressing Sindbis virus. The lysated is withdrawn, and applied to a replicate resin coated plate.

Although Sindbis virus is cytopathic, there is a window of at least 24 hours from the time of Sindbis virus infection where the stably transfected HEK 293 express both the recombinant YFP-SNAP-25-Hisx6 and BoNT/A can be used to test moieties or compounds for their ability to inhibit the toxin's catalytic activity in the cells. In another embodiment of the present invention, non-cytopathic forms of the Sindbis virus can be used to improve cell viability. In yet another embodiment of the present invention, inducible cell-lines that express YFP-SNAP-25-Hisx6 and conditionally express the recombinant BoNT LC (in the presence of an inducer) can be developed and used in the cell-based assays of the present invention.

Figure 4:
FIG. 4 is comprised of FIGS. 4A and 4B.

The recombinant BoNT/A light chain is efficiently expressed and catalytically active. To verify that the synthetic BoNT/A light chain LC is catalytically active, HEK 293 cells were transiently transfected using a mammalian expression vector containing BoNT/A LC. Incubation of mouse brain extract with lysates from the transfected cells resulted in cleavage of mouse SNAP-25, as monitored by immunoblots (FIG. 4A). FIGS. 4A and 4B show that synthetic BoNT/A LC is expressed in mammalian cells and catalytically active. FIG. 4A shows the results from an assay in which mouse brain extract was incubated with lysates prepared from HEK 293 cells transiently transfected with BoNT/A LC. Immunoblots showed that mouse endogenous SNAP-25 was cleaved by BoNT/A LC expressed in HEK 293 cells. (B) Primary neuronal cell cultures and HEK 293 cells stably expressing YFP-SNAP-25-Hisx6 were infected with a Sindbis virus overexpressing BoNT/A LC (moi 5) and analyzed for SNAP-25 cleavage by immunoblot. The synthetic BoNT/A LC was efficiently expressed and cleaved both endogenous neuronal SNAP-25 and YFP-SNAP-25-Hisx6.

Infection of primary neuronal cultures with a Sindbis virus overexpressing the synthetic BoNT/A LC also resulted in efficient cleavage of SNAP-25 in these neurons (FIG. 4B).

Cell-Based Assay for BoNT Catalytic Activity

Figure 5:
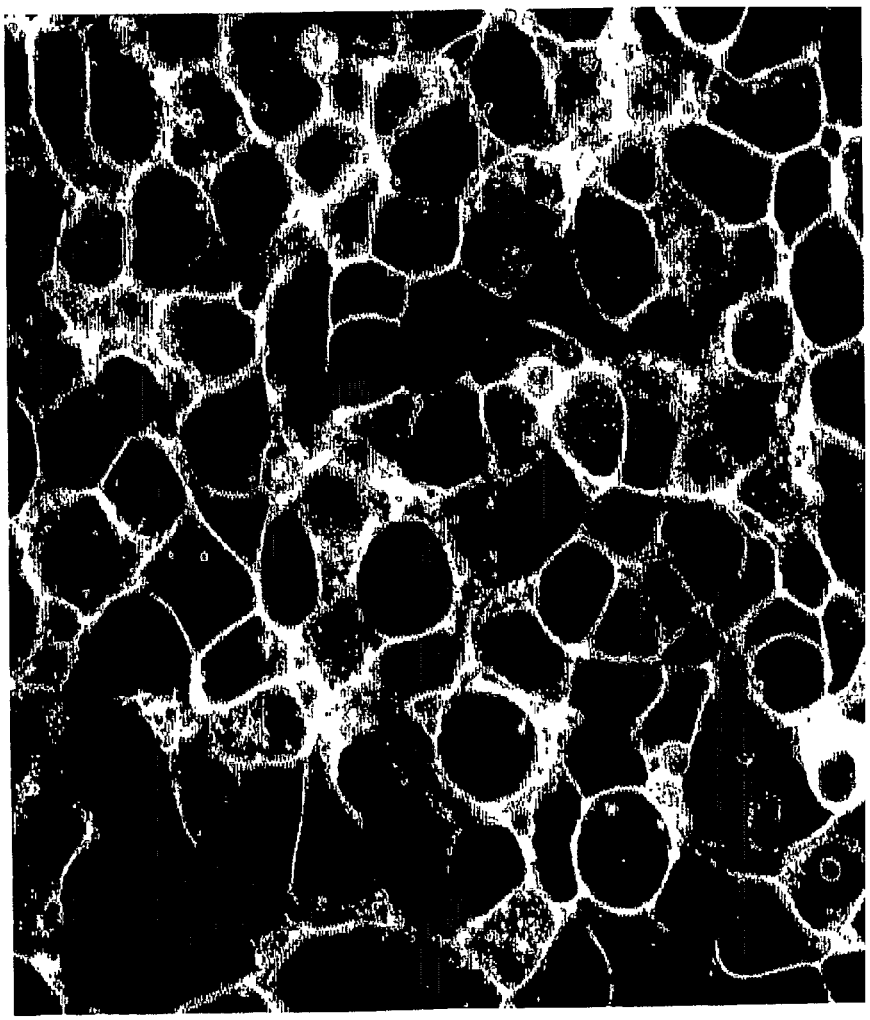
FIG. 5 is a photomicrograph of HEK 293 cells stably expressing YFP-SNAP-25-Hisx6. Cells were imaged for YFP fluorescence which showed the proper localization of YFP-SNAP-25-Hisx6 at the cell membranes.

Any inhibitor of the proteolytic activity of BoNT must have both low cytotoxicity and high intracellular penetration to be considered as a potential clinical antidote. Toward the goals of identifying clinically useful agents we have developed a cell based system to monitor the proteolytic activity of BoNT/A and BoNT/E. Two different clonal lines of human embryonic kidney cells (HEK293) were produced by transfecting the HEK293 cells so that they express high levels of YFP-SNAP25-Hisx6. These two cells lines are identified as YSH5b and YSH12b. HEK 29 cells stably expressing YFP-SNAP-5-Hisx6 are shown in FIG. 5, imaged for YFP fluorescence showing proper localization of YFP-SNAP-25-Hisx6 to the cell membranes. SNAP-25 is normally associated with cell membranes in neurons. Although HEK 293 cells do not express SNAP-25 endogenously, YFP-SNAP-25-Hisx6 expressed in these cells was properly localized to the cell membranes. Since HEK 293 cells do not express receptors for BoNT, a novel route is required to intoxicate these cells. We achieve this using a Sindbis virus vector engineered to express a catalytically active form of the light chain of BoNT (SV-LC).

Both lines of the YFP-SNAP25-Hisx6 expressing HEK 293 cells (i.e., YSH5b and YSH12b) as well as primary dissociated neurons show cleavage of SNAP-25 when infected with SV-LC (FIG. 4B). Immunoblot analysis of cell lysates reveals that all SNAP-25 associated protein (YFP-SNAP25-6His in HEK293 and native SNAP-25 in neurons) from transfected cells has a molecular weight consistent with BoNT/A cleavage.

The cleavage of YFP-SNAP-25-Hisx6 in the YSH5b and YSH12b cells by expression of BoNT LC can be monitored quantitatively using the assay system that is similar to the in-vitro methods is illustrated in FIG. 6. FIG. 6 illustrates one embodiment of the cell-based assay for BoNT catalytic activity. HEK 293 cells stably expressing YFP-SNAP-25-Hisx6 are exposed to BoNT and the amount of YFP-SNAP-25-Hisx6 cleavage is monitored by the YFP fluorescence bound to Nickel resin. This allow for high-throughput cell-based assay using similar assay platform as the in-vitro assay.

Figure 7:
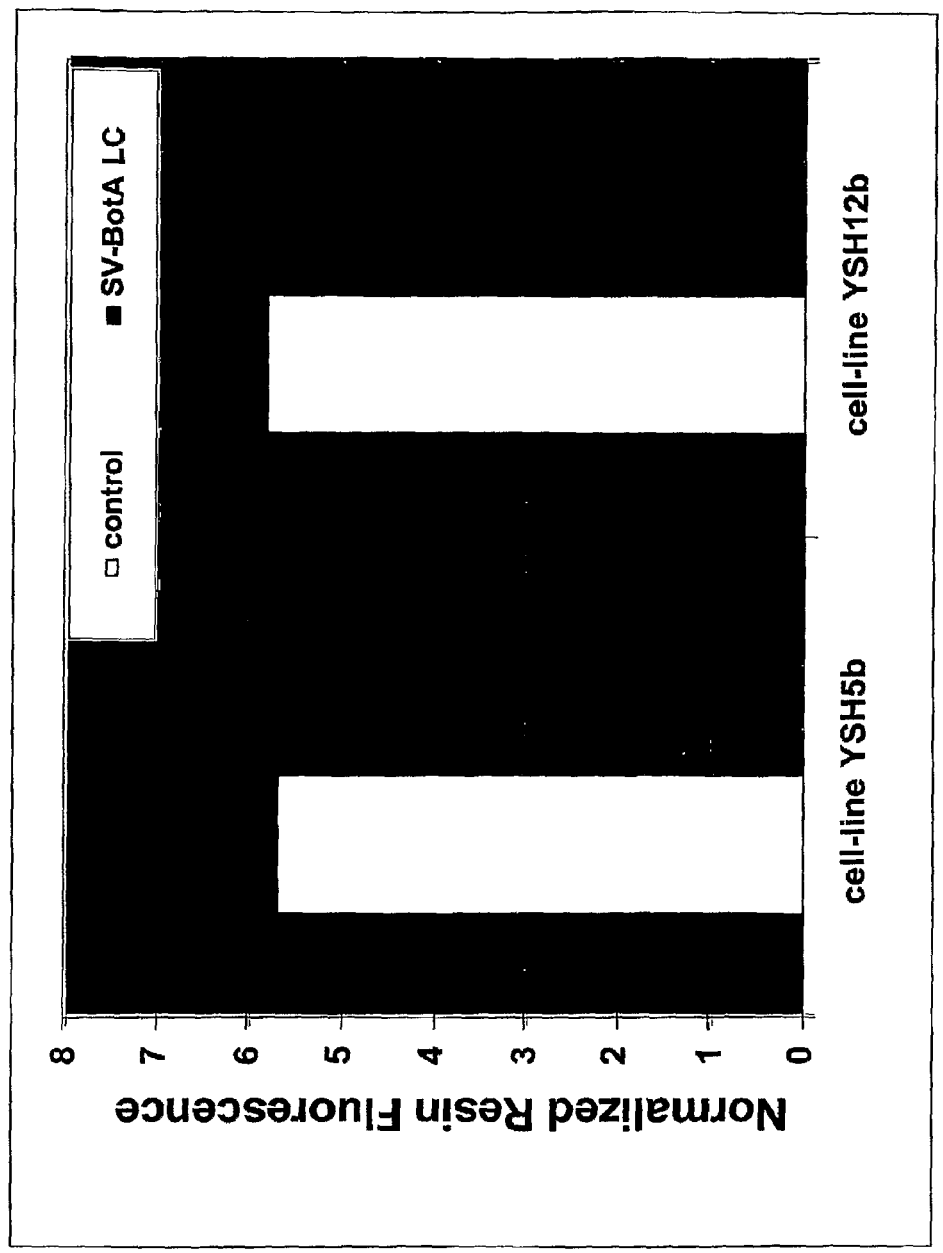
FIG. 7 shows the results of a cell-based assay for BoNT catalytic activity in which HEK 293 cell-lines YSH5b and YSH12b were infected with Sindbis virus over-expressing recombinant BoNT/A LC. The expressed BoNT/A LC efficiently cleaves YFP-SNAP-25-Hisx6 in these cells, resulting in a decrease in YFP fluorescence reporter signal bound a Nickel column.

Cleavage of the recombinant YFP-SNAP-25-6His by BoNT LC produces cell lysates containing YFP-SNAP-25 devoid of the His tag, which therefore results in a reduced quantity of fluorescence bound to nickel resin wells (FIG. 7). FIG. 7 shows the results from a cell-based assay for BoNT catalytic activity. HEK 293 cell-lines YSH5b and YSH12b were infected with Sindbis virus over-expressing recombinant BoNT/A LC. The expressed BoNT/A LC efficiently cleaves YFP-SNAP-25-Hisx6 in these cells resulting in a decrease in YFP fluorescence bound the Nickel column. If a molecule can enter the cells and inhibit activity of the BoNT light chain, resin bound fluorescence will be restored to control (non-SVLC infected) levels.

EXAMPLE 6

Construction of Type A and Type E BoNT Light Chains

Clostridial genes are aberrantly A/T rich and poorly translated in eukaryotic cells. To achieve efficient expression of the BoNT LC, we reconstructed codon-substituted BoNT/A and BoNT/E LC with these criteria: (1) preferred codon usage in *E. coli* and eukaryotic cells, (2) divide the LC into interchangeable domains to facilitate the design of chimeric BoNT LC, (3) insert restriction sites compatible with several types of expression systems. BoNT/A and /E LC are constructed in PCR reactions by overlap extension of oligonucleotides as building blocks. The synthetic LC are subcloned into appropriate mammalian expression vector and Sindbis virus vector.

Based on these criteria, synthetic BoNT/A and BoNT/E LCs were designed, introducing internal BaM H1 and Acc III sites into the gene to create modules "1", "2", and "3" (5' to 3'). The synthetic genes were engineered to include tandem Xho I, Nhe I, and Sph I sites at their 5" ends and Apa I on the 3' end. The sequence of the synthetic BoNT/A LC gene (SEQ ID No. 1) is shown in FIG. 8A and sequence of the synthetic BoNT/E LC gene (SEQ ID No. 2) is shown in FIG. 8B. FIG. 8A shows the nucleotide sequence (SEQ ID NO: 1) encoding BoNT/A LC optimized for expression in eukaryotic cells in which a BamHI (bold and underlined) and AccIII (italics+ double underlined) restriction enzyme sites have been engineered. FIG. 8B shows the nucleotide sequence (SEQ ID NO: 2) encoding BoNT/E LC optimized for expression in eukaryotic cells in which a BamHI (bold and underlined) and AccIII (italics+double underlined) restriction enzyme sites have been engineered.

Oligonucleotides of 50-60 nt were designed in pairs to introduce overlapping regions of 12 nt at their opposing ends. The oligos were optimized for preferred codon usage in *E. coli* and eukaryotic cells. These pairs were extended and amplified by using PCR to create fragments of ~100 nt, which were then utilized as building blocks in successive rounds of PCR with oligos having 12 nt overlaps with the ends of the prior PCR amplification. This type of "overlapping PCR" gene synthesis was utilized to create the entire synthetic gene. To monitor the fidelity of the gene construction process, PCR fragments were cloned into TA TOPO cloning vectors (Invitrogen) at regular intervals and sequenced to obtain template lacking mutations in coding sequence or restrictions sites.

The light chain sequences for BoNT/A and BoNT/E were divided into three sections by creating the internal restriction sites, BamHI (GGATCC (underlined in the sequences above) and AccIII (TCCGGA (double underlined in the sequences above) sites, without changing the amino acid sequence of the light chains (silent mutagenesis). For each serotype, Fragment One is from the ATC codon to the BamHI site (underlined). Fragment Two is from the BamHI site to the AccIII site (double underlined). Fragment Three is from the AccIII site to the final CAT codon.

Synthetic genes for the BoNT/A and BoNT/E LCs were subcloned into appropriate expression systems for biological applications. For those transient recombinant protein expression applications requiring plasmid the completed recombinant genes were transferred to pcDNA 3.1, using unique NheI and ApaI restriction sites in the expression plasmid in the following manner: (a) Fragment One is excised using SpeI/BamHI and ligated into NheI/BamHI sites of pcDNA3.1(+); (b) Fragment Three is cut with SpeI/ApaI and ligated into the XbaI/ApaI sites of pcDNA3.1(+)/Fragment 1; (c) finally, Fragment Two is cloned in using BamHI/AccIII to get the complete light chain sequence. After verification by DNA sequencing of the insert ligation sites, preparative amounts of plasmid were purified.

EXAMPLE 7

Construction of YFP-BoNT/A and YFP-BoNT/E Expressing Vectors

For recombinant protein expression applications requiring introduction of mammalian virus the genes were transferred to pSindREP 5 (Invitrogen), using unique Xba I and Apa I sites in the viral DNA vector (note: Xba I and Nhe I restriction sites have compatible ends for ligation) (NheI/ApaI sites for the insert). pVSindREP5 can be used to make viral replicons (ie. replication-deficient virus). After verification by DNA sequencing of the insert ligation sites, preparative amounts of the DNAs were purified for later expression studies. For studies of expression using fluorescent fusion proteins, the BoNT/A and BoNT/E LC genes were transferred to a plasmid containing the coding sequence for yellow fluorescent protein (YFP) pEYFP (EYFP-C1 from Clontech), using unique Xho I and Apa I sites. After verification by DNA sequencing of the insert ligation sites, preparative amounts of plasmid were purified.

YFP-BoNT/A and YFP-BoNT/E expression vectors are also constructed by ligating the synthetic light chains into the EYFP-C1 vector (Clontech) using XhoI/ApaI sites to facilitate tracking the light chains in separate experiments.

EXAMPLE 8

Construction of Sinbis Viral Vector for Expressing BoNT Light Chains

For recombinant protein expression applications requiring introduction of mammalian virus, the genes are transferred to Sindbis virus vector pVSind 1 using XbaI/NotI sites in the vector (NheI/NotI in the insert). pVSind 1 vector is modified from the TE12Q strain of Sindbis described by Lewis J, et al., Nat Med (1999) 5:832-5, which is hereby incorporated by reference in its entirety. This construct is used to make replication-competent Sindbis virus.

EXAMPLE 9

Construction of pGEX6P2 vector for Expressing BoNT Light Chains

The BoNT/A is also cloned into pGEX6P2 vector (Amersham Pharmacia Biotech) to express in bacteria as a source of BoNT/A light chain for antibody production and in-vitro assays, so that the risk associated with using the holotoxin can be minimized.

EXAMPLE 10

Construction of Chimeric BoNT/A and BoNT/E LCs

The addition of the unique restriction sites within the BoNT/A and BoNT/E light chains described herein also allows for convenient swapping of domains from BoNT/A and E light chains for creation of chimeric light chains in order to produce light chains having novel properties for use in identifying inhibitors of BoNTs and for use themselves as therapeutic products.

The intermediate constructs are cloned into TA TOPO cloning vectors (Invitrogen) to check for PCR fidelity by sequencing. The completed fragments of the sequence are then ligated using the internal restriction sites in pcDNA3.1 (Neo+): (a) Fragment One is excised using SpeI/BamHI and ligated into NheI/BamHI sites of pcDNA3.1(+); (b) Fragment Three is cut with SpeI/ApaI and ligated into the XbaI/ApaI sites of pcDNA3.1(+)/Fragment 1; (c) finally, Fragment Two is cloned in using BamHI/AccIII to product a complete chimeric light chain sequence. The chimeric light chains are constructed by the same procedure with different combinations of Fragments One, Two, Three of BoNT/A and BoNT/E. After each assembly step, verification of correct ligation was carried out by DNA sequencing. The following chimeric LCs were transferred to pcDNA 3.1, using the unique Nhe I and Apa I sites in the expression plasmid: 1) A1-A2-E3, 2) A1-E2-E3, 3) A1-E2-A3, 4) E1-A2-A3, 5) E1-A2-E3, 6) E1-E2-A3. These same chimeric LCs were transferred to the replication-competent Sindbis expression vector pVSind1, using unique Xba 1 and Not 1 sites, the latter derived from the TA vector. In addition to the chimeras, the full-length BoNT/A and BoNT/E LC genes were transferred to the pVSind1 vector to enable comparison with the chimeric forms.

Alternative Embodiments

One can easily use green fluorescent protein (GFP) instead of yellow fluorescent protein (YFP). Furthermore, reporter moieties other than fluorescent markets can be used. For example, colorimetric substrate reactions such as beta-galactosidase, alkaline phosphatase, or glutathione-S-transferase (GST) or other enzymes along with the appropriate substrate or antibody (for an immunoassay) can be used. An absorption assay can be used to detect inhibitors of BoNT activity. Some examples of other enzymes and substrates can be found in U.S. Pat. No. 6,197,534. Any reporter compound which can be detected in an immunoassay, absorption assay, or substrate assay can be used.

A preferred embodiment is described as an indicator for BoNT/A and as an indicator for BoNT/E. The present invention can also be easily adapted by those of skill in the art for monitoring syntaxin cleaving by BoNT/C or VAMP/synaptobrevin cleaving by BoNT/B, BoNT/D, BoNT/F, and BoNT/G.

The nucleic acid and amino acid sequences referenced in the instant specification can be found in the corresponding SEQ ID Numbers, which are identified in Table 1 below, the sequence listing of each of which is hereby incorporated by reference in its entirety.

TABLE 1

| SEQ ID No. | Type of Sequence and Protein Encoded |
| --- | --- |
| 1 | BoNT/A nucleic acid |
| 2 | BoNT/E nucleic acid |
| 3 | BoNT/A amino acid |
| 4 | BoNT/E amino acid |
| 5 | BoNT/C nucleic acid |
| 6 | BoNT/C amino acid |
| 7 | BoNT/B nucleic acid |
| 8 | BoNT/B amino acid |
| 9 | BoNT/D nucleic acid |
| 10 | BoNT/D amino acid |
| 11 | BoNT/F nucleic acid |
| 12 | BoNT/F amino acid |
| 13 | BoNT/G nucleic acid |
| 14 | BoNT/G amino acid |
| 15 | Murine SNAP-25 nucleic acid |
| 16 | Murine SNAP-25 amino acid |

In describing representative embodiments of the invention, the specification may have presented the method and/or process of the invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. In addition, the claims directed to the method and/or process of the invention should not be limited to the performance of their steps in the order written, to the extent that the method or process does not rely on the particular order of steps, and one skilled in the art can readily appreciate that the sequences may be varied and still remain within the spirit and scope of the invention.

The foregoing disclosure of the embodiments of the invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

REFERENCES

1. Adler M., et al., Pharmacological countermeasures for Botulinum intoxication. (Chapter 12) Advances in low dose exposure to chemical and biological weapons. CRC Press. 2001. pp 373-387.
2. Arnon S S, et al., Working group on Civilian Biodefense. Botulinum toxin as a biological weapon: medical and public health management. JAMA 2001, 285:1059-70.
3. Marks J D. Advances in monoclonal antibody treatment of BoNT intoxication. Interagency Botulinum Research Coordinating Committee. October 2001. Abstract.
4. Cohen J, et al., Bioterrorism. Vaccines for biodefense: a system in distress. Science 2001, 294:498-501.
5. Oyler G A, et al., Development of a cell-based high-throughput screening system for inhibitors of Botulinum toxin. Interagency Botulinum Research Coordinating Committee, October 2001.
6. Simpson L L. Botulinum toxin and tetanus toxin recognize similar membrane determinants. Brain Res 1984, 305: 177-80.
7. Lalli G, et al., Functional characterization of tetanus and Botulinum neurotoxins binding domains. J Cell Sci 1999, 112: 2715-24.
8. Oyler G A, et al., The identification of a novel synaptosomal-associated protein, SNAP-25, differentially expressed by neuronal subpopulations. J Cell Biol 1989, 109:3039-52.
9. Blasi J, et al., Botulinum neurotoxin A selectively cleaves the synaptic protein SNAP-25. Nature 1993, 365: 160-3.
10. Schiavo G, et al., Botulinum neurotoxins serotypes A and E cleave SNAP-25 at distinct COOH-terminal peptide bonds. FEBS Lett 1993, 335:99-103.
11. Schiavo G, et al., Identification of the nerve terminal targets of Botulinum neurotoxin serotypes A, D and E. J Biol Chem 1993: 268: 23784-7.
12. Schiavo G, et al., Tetanus and Botulinum-B neurotoxins block neurotransmitter release by proteolytic cleavage of synaptobrevin. Nature 1992, 359: 832-5.
13. Schiavo G, et al., C. Botulinum neurotoxin serotype F is a zinc endopeptidase specific for VAMP/synaptobrevin. J Biol Chem 1993, 268: 11516-9.
14. Yamasaki S, et al., Botulinum neurotoxin serptype G proteolyses the Ala81-Ala82 bond of rat synaptobrevin 2. Biochem Biophys Res Comm 1994, 200: 829-35.
15. Lewis J, et al., Inhibition of virus-induced neuronal apoptosis by Bax. Nat. Med 1999, 5:832-5.
16. Schmidt J J, et al., High-throughput assays for botulinum neurotoxin proteolytic activity: serotypes A, B, D, and F. Anal Biochem 2001 Sep. 1; 296(1):130-7.
17. Anne C, et al., High-throughput fluorogenic assay for determination of Botulinum type B neurotoxin protease activity. Anal Biochem 2001, 291: 253-61.
18. Agapov E V, et al., Noncytopathic Sindbis virus RNA vectors for heterologous gene expression. Proc Natl Acad Sci USA 1998 Oct. 27, 95(22):12989-94.

We claim:

1. A cell line expressing a botulinum neurotoxin substrate complex, wherein said complex comprises:
   (a) a peptide substrate selected from the group consisting of synaptosomal associated protein of 25 kD (SNAP-25), a SNAP-25 isoform, syntaxin, a syntaxin isoform, vesicle-associated membrane protein (VAMP), a VAMP isoform, and peptides having at least 80% identity to the foregoing, wherein said peptide substrate comprises a motif of soluble NSF (N-ethylmaleimide-sensitive fusion protein) attachment protein receptor (a SNARE motif);
   (b) a reporter domain comprising a fluorescent protein covalently attached to one side of said peptide substrate; and
   (c) an immobilization domain covalently attached to an opposite side of said peptide substrate.

2. The cell line of claim 1, wherein said reporter domain is on an amino terminal side of said peptide substrate and said immobilization domain is on a carboxy terminal side of said peptide substrate.

3. The cell line of claim 1, wherein the fluorescent protein is selected from the group consisting of yellow fluorescent protein (YFP), blue fluorescent protein (BFP), green fluorescent protein (GFP), red fluorescent protein (RFP) and fluorescing mutants thereof 4. The cell line of claim 1, wherein said immobilization domain is selected from the group consisting of a polyhistidine, Protein A and a maltose binding protein.

5. The cell line of claim 4, wherein said polyhistidine is hexashistidine.

6. The cell line of claim 1, wherein the SNAP-25 peptide substrate comprises the amino acid sequence of SEQ ID NO: 16.

7. The cell line of claim 1, wherein said substrate complex is a recombinant product wherein said peptide is encoded by the nucleic acid sequence shown in SEQ ID NO:15.

8. The cell line of claim 1, wherein the peptide substrate is SNAP-25 and the botulinum neurotoxin is selected from the group consisting of BoNT/A, BoNT/E, and BoNT/C.

9. The cell line of claim 1, wherein the peptide substrate is syntaxin and the botulinum neurotoxin is BoNT/C.

10. The cell line of claim 1, wherein the peptide substrate is VAMP and the botulinum neurotoxin is selected from the group consisting of BoNT/B, BoNT/D, BoNT/F and BoNT/G.

11. A method for identifying a botulinum neurotoxin inhibitor comprising the steps of:
   (i) exposing botulinum neurotoxin substrate complex expressing cells to a botulinum neurotoxin, in the presence and absence of a test molecule, wherein said botulinum neurotoxin substrate complex comprises:
      (a) a peptide substrate selected from the group consisting of synaptosomal associated protein of 25 kD (SNAP-25), a SNAP-25 isoform, syntaxin, a syntaxin isoform, vesicle-associated membrane protein (VAMP), a VAMP isoform, and peptides having at least 80% identity to the foregoing, wherein said peptide substrate comprises a motif of soluble NSF (N-ethylmaleimide-sensitive fusion protein) attachment protein receptor (a SNARE motif);
      (b) a reporter domain comprising a fluorescent protein covalently attached to one side of said peptide substrate; and
      (c) an immobilization domain covalently attached to an opposite side of said peptide substrate,
   wherein said complex is cleaved to produce a cleaved complex in the absence of said test molecule;
   (ii) lysing said cells and collecting cell lysate from said cells;
   (iii) immobilizing the substrate complex on a solid support;
   (iv) comparing the effect of the presence of said test molecule on the amount of said cleaved complex to the amount of said cleaved complex in the absence of said test molecule; and
   (v) identifying the test molecule as a botulinum neurotoxin inhibitor if the presence of said test molecule decreases the relative amount of cleaved complex produced in said cells as compared to the amount of cleaved complex produced in said cells in the absence of said test molecule.

12. The method of claim 11, wherein said immobilization step comprises:
   exposing said cell lysate to a solid support comprised of a binding partner for said immobilization domain so that said substrate complex and the cleaved complex comprising the immobilized domain bind to the solid support; and
   washing the solid support to remove any unbound molecules.

13. The method of claim 11, wherein said reporter domain is capable of being detected in a manner to quantitatively measure the quantity of substrate complex bound to a solid support or the quantity of the cleaved complex released from a solid support.

14. The method of claim 11, wherein the amount of cleaved complex is determined by measuring the fluorescence of said reporter domain in the cleaved complex.

15. The method of claim 11, wherein said reporter domain is on an amino terminal side of said peptide substrate and said immobilization domain is on a carboxy terminal side of said peptide substrate.

16. The method of claim 11, wherein the fluorescent protein is selected from the group consisting of yellow fluorescent protein (YFP), blue fluorescent protein (BFP), green fluorescent protein (GFP), red fluorescent protein (RFP) and fluorescing mutants thereof.

17. The method of claim 11, wherein said immobilization domain is selected from the group consisting of a polyhistidine, Protein A and a maltose binding protein.

18. The method of claim 17, wherein said polyhistidine is hexahistidine.

19. The method of claim 11, wherein the SNAP-25 peptide substrate comprises the amino acid sequence of SEQ ID NO: 16.

20. The method claim 11, wherein said substrate complex is a recombinant product wherein said peptide is encoded by the nucleic acid sequence shown in SEQ ID NO:15.

21. The method of claim 11, wherein the peptide substrate is SNAP-25 and the botulinum neurotoxin is selected from the group consisting of BoNT/A, BoNT/E, and BoNT/C.

22. The method of claim 11, wherein the peptide substrate is syntaxin and the botulinum neurotoxin is BoNT/C.

23. The method of claim 11, wherein the peptide substrate is VAMP and the botulinum neurotoxin is selected from the group consisting of BoNT/B, BoNT/D, BoNT/F and BoNT/G.

24. The method of claim 11, wherein said botulinum neurotoxin in step (i) is delivered to said cells by means selected from administering a botulinum neurotoxin to said cells and expressing said botulinum neurotoxin in said cells by a recombinant vector.

25. The method of claim 11, wherein said test molecule is one of a plurality of compounds having established inhibitory properties for metalloprotease or potential inhibitory properties for metalloprotease.

26. The method of claim 11, wherein said test molecule is one of a plurality of small molecules in a combinatorial library selected from the group consisting of small molecule combinatorial library and peptide combinatorial library.

* * * * *